US012596094B2

(12) United States Patent
Sikora et al.

(10) Patent No.: US 12,596,094 B2
(45) **Date of Patent: \*Apr. 7, 2026**

(54) METHODS, SYSTEMS, AND COMPUTER READABLE MEDIA FOR MAKING BASE CALLS IN NUCLEIC ACID SEQUENCING

(71) Applicant: LIFE TECHNOLOGIES CORPORATION, Carlsbad, CA (US)

(72) Inventors: Marcin Sikora, Burlingame, CA (US); Melville Davey, Westbrook, CT (US); Christian Koller, San Francisco, CA (US); Simon Cawley, Oakland, CA (US); Alan Williams, Albany, CA (US); David Kulp, Shelburne Falls, MA (US)

(73) Assignee: Life Technologies Corporation, Carlsbad, CA (US)

( * ) Notice: Subject to any disclaimer, the term of this patent is extended or adjusted under 35 U.S.C. 154(b) by 774 days.

This patent is subject to a terminal disclaimer.

(21) Appl. No.: 17/937,797

(22) Filed: Oct. 4, 2022

(65) Prior Publication Data

US 2023/0194464 A1    Jun. 22, 2023

Related U.S. Application Data

(63) Continuation of application No. 16/196,502, filed on Nov. 20, 2018, now Pat. No. 11,474,070, which is a continuation of application No. 13/588,408, filed on Aug. 17, 2012, now abandoned, which is a continuation-in-part of application No. PCT/US2011/067959, filed on Dec. 29, 2011, and a continuation-in-part of application No. 13/340,490, filed on Dec. 29, 2011, now Pat. No. 10,241,075.

(60) Provisional application No. 61/525,073, filed on Aug. 18, 2011, provisional application No. 61/428,733, filed on Dec. 30, 2010.

(51) Int. Cl.

| | |
|---|---|
| *G01N 27/414* | (2006.01) |
| *C12Q 1/6869* | (2018.01) |
| *G16B 30/00* | (2019.01) |
| *G16B 30/10* | (2019.01) |
| *G01N 27/27* | (2006.01) |
| *G16B 30/20* | (2019.01) |

(52) U.S. Cl.

CPC ....... *G01N 27/4145* (2013.01); *C12Q 1/6869* (2013.01); *G16B 30/00* (2019.02); *G16B 30/10* (2019.02); *C12Q 2535/122* (2013.01); *C12Q 2565/607* (2013.01); *G01N 27/27* (2013.01); *G16B 30/20* (2019.02)

(58) Field of Classification Search

CPC .... G01N 27/4145; G16B 30/10; G16B 30/00; C12Q 1/6869

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 5,210,015 | A | 5/1993 | Gelfand et al. |
| 5,399,491 | A | 3/1995 | Kacian et al. |
| 5,587,128 | A | 12/1996 | Wilding et al. |
| 5,750,341 | A | 5/1998 | Macevicz |
| 5,854,033 | A | 12/1998 | Lizardi |
| 6,033,546 | A | 3/2000 | Ramsey |
| 6,054,034 | A | 4/2000 | Soane et al. |
| 6,174,670 | B1 | 1/2001 | Wittwer et al. |
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,399,952 | B1 | 6/2002 | Maher et al. |
| 6,404,907 | B1 | 6/2002 | Gilchrist et al. |
| 6,554,987 | B1 | 4/2003 | Gilchrist et al. |
| 6,613,525 | B2 | 9/2003 | Nelson et al. |
| 6,780,591 | B2 | 8/2004 | Williams et al. |
| 6,828,100 | B1 | 12/2004 | Ronaghi |
| 6,833,246 | B2 | 12/2004 | Balasubramanian |

(Continued)

FOREIGN PATENT DOCUMENTS

| | | |
|---|---|---|
| GB | 2461127 A | 12/2009 |
| JP | H04262799 A | 9/1992 |

(Continued)

OTHER PUBLICATIONS

U.S. Appl. No. 13/339,753, "Time-Warped Background Signal for Sequencing-by-Synthesis Operations", US Application filed Dec. 29, 2011.

(Continued)

*Primary Examiner* — Jerry Lin

(57) ABSTRACT

A method for nucleic acid sequencing includes receiving a plurality of observed or measured signals indicative of a parameter observed or measured for a plurality of defined spaces; determining, for at least some of the defined spaces, whether the defined space comprises one or more sample nucleic acids; processing, for at least some of the defined spaces, the observed or measured signal to improve a quality of the observed or measured signal; generating, for at least some of the defined spaces, a set of candidate sequences of bases for the defined space using one or more metrics adapted to associate a score or penalty to the candidate sequences of bases; and selecting the candidate sequence leading to a highest score or a lowest penalty as corresponding to the correct sequence for the one or more sample nucleic acids in the defined space.

20 Claims, 27 Drawing Sheets

Specification includes a Sequence Listing.

(56)  References Cited

U.S. PATENT DOCUMENTS

| | | | |
|---|---|---|---|
| 6,911,327 B2 | 6/2005 | McMillan et al. |
| 6,960,437 B2 | 11/2005 | Enzelberger et al. |
| 7,037,687 B2 | 5/2006 | Williams et al. |
| 7,049,645 B2 | 5/2006 | Sawada et al. |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,535,232 B2 | 5/2009 | Barbaro et al. |
| 7,575,865 B2 | 8/2009 | Leamon et al. |
| 7,645,596 B2 | 1/2010 | Williams et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,875,440 B2 | 1/2011 | Williams et al. |
| 7,948,015 B2 | 5/2011 | Rothberg et al. |
| 8,594,951 B2 | 11/2013 | Homer |
| 9,388,462 B1 | 7/2016 | Eltoukhy |
| 2003/0219797 A1 | 11/2003 | Zhao et al. |
| 2004/0018506 A1 | 1/2004 | Koehler et al. |
| 2004/0197793 A1 | 10/2004 | Hassibi et al. |
| 2004/0197845 A1 | 10/2004 | Hassibi et al. |
| 2005/0084851 A1 | 4/2005 | Ronaghi et al. |
| 2006/0040297 A1 | 2/2006 | Leamon et al. |
| 2006/0147935 A1 | 7/2006 | Linnarsson |
| 2006/0147983 A1 | 7/2006 | O'Uchi |
| 2007/0059733 A1 | 3/2007 | Sundararajan et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2010/0035252 A1 | 2/2010 | Rothberg et al. |
| 2010/0075327 A1 | 3/2010 | Maxham et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0159461 A1 | 6/2010 | Toumazou et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0183320 A1 | 7/2011 | Flusberg et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0256631 A1 | 10/2011 | Tomaney et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0197623 A1 | 8/2012 | Homer |
| 2013/0060482 A1 | 3/2013 | Sikora et al. |
| 2013/0090860 A1 | 4/2013 | Sikora et al. |
| 2014/0220558 A1 | 8/2014 | Homer et al. |

FOREIGN PATENT DOCUMENTS

| | | | |
|---|---|---|---|
| WO | WO-1999019717 A1 | 4/1999 |
| WO | WO-9957321 A1 | 11/1999 |
| WO | WO-0220837 A2 | 3/2002 |
| WO | WO-2002024322 A2 | 3/2002 |
| WO | WO-03020895 A2 | 3/2003 |
| WO | WO-2004001015 A2 | 12/2003 |
| WO | WO-2005040425 A2 | 5/2005 |
| WO | WO-2007098049 A2 | 8/2007 |
| WO | WO-2008076406 A2 | 6/2008 |
| WO | WO-2008092150 A1 | 7/2008 |
| WO | WO-2008092155 A2 | 7/2008 |
| WO | WO-2009117119 A1 | 9/2009 |
| WO | WO-2009158006 A2 | 12/2009 |
| WO | WO-2010047804 A1 | 4/2010 |
| WO | WO-2010077859 A2 | 7/2010 |
| WO | WO-2010117804 A2 | 10/2010 |
| WO | WO-2010138182 A2 | 12/2010 |
| WO | WO-2011120964 A1 | 10/2011 |
| WO | WO-2011156707 A2 | 12/2011 |
| WO | WO-2012058459 A2 | 5/2012 |
| WO | WO-2012092515 A2 | 7/2012 |

OTHER PUBLICATIONS

U.S. Appl. No. 13/339,846, "Models for Analyzing Data From Sequencing-by-Synthesis Operations", US Application filed Dec. 29, 2011.

U.S. Appl. No. 13/588,408, "Methods, Systems, and Computer Readable Media for Making Base Calls in Nucleic Acid Sequencing" US Application filed Aug. 17, 2012.

"454 Sequencing System Software Manual Version 2.6," Part B : GS Run Processor, GS Reporter, GS Run Browser, GS Support Tool, May 2011,112 pages, retrieved at http://genepool.bio.ed.ac.uk/Gene_Pool/454_software/Manuals/454SeqSys_SWManualv2.6 PartB May2011 .pdf, last visited Aug. 31, 2012.

Ahmadian A., et al., "Pyrosequencing: History, Biochemistry And Future," Clinica Chimica Acta, Jan. 2006, vol. 363, pp. 3-94.

Anderson E.P., et al., "A System For Multiplexed Direct Electrical Detection Of DNA Synthesis," Sensors and actuators. B, Chemical, Jan. 2008, vol. 129, No. 1, pp. 79-86.

Appendix to the Specification of U.S. Appl. No. 61/198,222, filed Nov. 4, 2008, 50 pages.

Baldi P., et al., "Machine-Learning Foundations: The Probabilistic Framework," Chapter 2, Bioinformatics: The Machine Learning Approach, Second Edition, The MIT Press, 2001, pp. 47-65.

Balzer S., et al., "Characteristics Of 454 Pyrosequencing Data-enabling Realistic Simulation With Flowsim," Bioinformatics, Sep. 15, 2010, vol. 26, No. 18, pp. i420-I425.

Barbaro M., et al., "Fully Electronic DNA Hybridization Detection by a Standard CMOS Biochip," Sensors and Actuators B: Chemical, 2006, vol. 118, pp. 41-46.

Brockman W., et al., "Quality Scores And Snp Detection In Sequencing-by-synthesis Systems," Genome Research, May 2008, vol. 18, No. 5, pp. 763-770.

Eltoukhy H., et al., "Modeling and Base-Calling for DNA Sequencing-By-Synthesis," IEEE International Conference on Acoustics, Speech, and Signal Processing, May 2006, vol. 2, pp. II-1032-II-1035.

(56)　　　　　References Cited

OTHER PUBLICATIONS

EP12823719.5, Extended European Search Report mailed Sep. 25, 2015, 12 pp.

EP12823719.5, Partial European Search Report mailed May 12, 2015, 3 pages.

EP19181402.9, Extended Search Report, Feb. 19, 2020, 8 pages.

Finotello F., et al., "Comparative Analysis Of Algorithms For Whole-Genome Assembly Of Pyrosequencing Data," Briefings in Bioinformatics Advance Access, Oct. 21, 2011, pp. 1-12.

Hammond P.A., et al., "Design of a Single-Chip pH Sensor Using a Conventional 0.6-μm CMOS Process," IEEE Sensors Journal, Dec. 2004, vol. 4, No. 6, pp. 706-712.

Heer F., et al., "Single-chip Microelectronic System To Interface With Living Cells," Biosensors and Bioelectronics, May 15, 2007, vol. 22, No. 11, pp. 2546-2553.

Hert D.G., et aL, "Advantages And Limitations Of Next-generation Sequencing Technologies: A Comparison Of Electrophoresis And Non-electrophoresis Methods," Electroghoresis, Dec. 2008, vol. 29, No. 23, pp. 4618-4626.

Hizawa T., et aL, "Fabrication Of a Two-dimensional pH Image Sensor Using A Charge Transfer Technique," Sensors and Actuators B: Chemical, Oct. 2006, vol. 117, No. 2, pp. 509-515.

Hughes R.C., et al., "Chemical Microsensors," Science, Oct. 4, 1991, vol. 254, pp. 74-80.

Huse S.M., et aL, "Accuracy and Quality of Massively Parallel DNA Pyrosequencing," Genome Biology, 2007, vol. 8 (7), Article R143, pp. R143.1-R143.9.

Ji Y., et aL, "BM-BC: A Bayesian Method of base Calling for Solexa Sequence Data," Department of Biostatistics, The University of Texas M. D. Anderson Cancer Center, Houston, Texas, U.S.A, 2010, pp. 1-27, URL: http://odin.mdacc.tmc.edu/-ylii/BMBC/bmbc-ie2.pdf.

Kao W.-C., et al., "BayesCall: A Model-Based Base-Calling Algorithm for High-Throughput Short-Read Sequencing," Genome Research, Oct. 2009, vol. 19, No. 10, pp. 1884-1895.

Langaee T., et al., "Genetic Variation Analyses By Pyrosequencing," Mutation Research, Jun. 3, 2005, vol. 573, pp. 96-102.

Leamon J.H., et al., "Cramming More Sequencing Reactions onto Microreactor Chips," Chemical Reviews, Aug. 2007, vol. 107, No. 8, pp. 3367-3376.

Ledergerber C., et al., "Base-calling For Next-generation Sequencing Platforms," Briefings in Bioinformatics Advance Access, Jan. 18, 2011, vol. 12, No. 5, pp. 489-497.

Li, Heng et al., "Fast and accurate long-read alignment with Burrows-Wheeler transform", Bioinformatics, vol. 26 No. 5, 2010, 589-595.

Li, Heng et al., "Fast and accurate short read alignment with Burrows-Wheeler transform", Bioinformatics, vol. 25 No. 14, 2009, 1754-1760.

Li, Heng "Exploring single-sample SNP and INDEL calling with whole-genome de novo assembly", Bioinformatics, 28, 14:May 7, 2012, pp. 1838-1844.

Lysholm F., et aL, "FAAST: Flow-Space Assisted Alignment Search Tool," BMC Bioinformatics, Jul. 19, 2011, vol. 12, 7 Pages, Retrieved from the Internet: URL: http://www. biomedcentral.com/1471-2105/12/293.

Margulies et al., "Supplemental Materials, Genome Sequencing in Microfabricated High-Density Picolitre Reactors", Nature, vol. 437, No. 15, 2005, pp. 1-34.

Margulies M., et al., "Genome Sequencing in Microfabricated High-Density Picolitre Reactors," Nature, 2005, vol. 437, No. 7057, pp. 376-380.

Martinoia S., et al., "Development of ISFET Array-Based Microsystems for Bioelectrochemical Measurements of Cell Populations," Biosensors & Bioelectronics, Dec. 2001, vol. 16, Nos. 9-12, pp. 1043-1050.

Massingham T., et al., "All Your Base: A Fast And Accurate Probabilistic Approach to Base Calling," Euroclean Bioinformatics Institute, Wellcome Trust Genome Cam12us, Hinxton, Cambridgeshire, UK, Oct. 26, 2011, pp. 1-26, Retrieved from the Internet: URL: http://www.ebi.ac.uk/goldman-srv/AYB/references/ayb_revised.pdf.

Metzker M.L., "Emerging Technologies In DNA Sequencing," Genome Research, Dec. 2005, vol. 15, pp. 1767-1776.

Milgrew M. J., et aL, "The Development of Scalable Sensor Arrays Using Standard CMOS Technology," Sensors and Actuators B: Chemical, Sep. 2004, vol. 103, Nos. 1-2, pp. 37-42.

MilgrewM.J., et al., "A Large Transistor-based Sensor Array Chip for Direct Extracellular Imaging," Sensors and Actuators B: Chemical, 2005, vol. 111-112, pp. 347-353.

Mir M., et al., "Integrated Electrochemical DNA Biosensors For Lab-on-a-chip Devices," Electrophoresis, Oct. 2009, vol. 30, No. 19, pp. 3386-3397.

Ning, Zemin et al., "SSAHA: A Fast Search Method for Large DNA Databases", Genome Res., 11:, 2001, 1725-1729.

PCT/US2011/067959, International Search Report and Written Opinion mailed on Nov. 16, 2012.

PCT/US2012/051361, International Preliminary Report on Patentability mailed Feb. 27, 14, 10 pages.

PCT/US2012/051361, International Search Report and Written Opinion mailed on Oct. 23, 2012.

Pourmand N., et aL, "Direct Electrical Detection of DNA Synthesis," Proceedings of the National Academy of Sciences, Apr. 25, 2006, vol. 103, No. 17, pp. 6466-6470.

Ronaghi M., et aL, "A Sequencing Method Based on Real-Time Pyrophosphate," Science, Jul. 17, 1998, vol. 281, pp. 363-365.

Ronaghi M., et al., "Pyrosequencing Sheds Light on DNA Sequencing," Genome Research, Jan. 2001, vol. 11, pp. 3-11.

Smith, T. F. et al., "Identification of Common Molecular Subsequences", Journal of Molecular Biology, 147, 10:, 1981, 195-197.

Specification & Drawings of U.S. Appl. No. 61/198,222, filed Nov. 4, 2008.

Svantesson A., et aL, "A Mathematical Model Of The Pyrosequencing Reaction System," Biophysical Chemistry, Jul. 1, 2004, vol. 100, pp. 129-145.

Trojanowicz M., et al., "Recent Developments In Electrochemical Flow Detections—a Review: Part I. Flow Analysis And Capillary Electrophoresis," Analytica Chimica Acta, Oct. 19, 2009, vol. 653, No. 1, pp. 36-58.

U.S. Appl. No. 13/588,408, Non-Final Office Action mailed May 7, 2015, 14 pages.

U.S. Appl. No. 13/645,058, Non-Final Office Action mailed Jun. 4, 2015, 7 pages.

Xu X., et al., "Integration Of Electrochemistry In Micro-total Analysis Systems For Biochemical Assays: Recent Developments," Talanta, Nov. 15, 2009, vol. 80, No. 1, pp. 8-18.

Yeowt.C.W., et al., "A Very Large Integrated pH-ISFET Sensor Array Chip Compatible with Standard CMOS Processes," Sensor and Actuators B: Chemical, Oct. 1997, vol. 44, Nos. 1-3, pp. 434-440.

Drain (222)     Source (221)

Reagent 2 (230)     Reagent 1 (232)

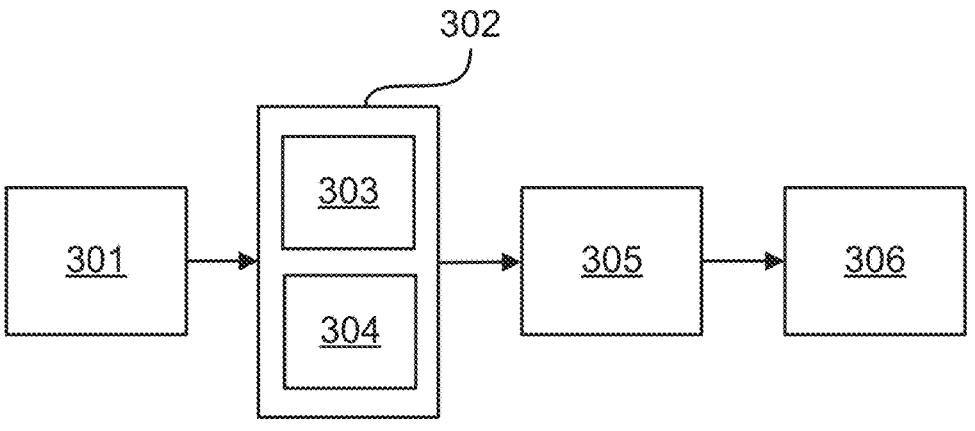

Fig. 3

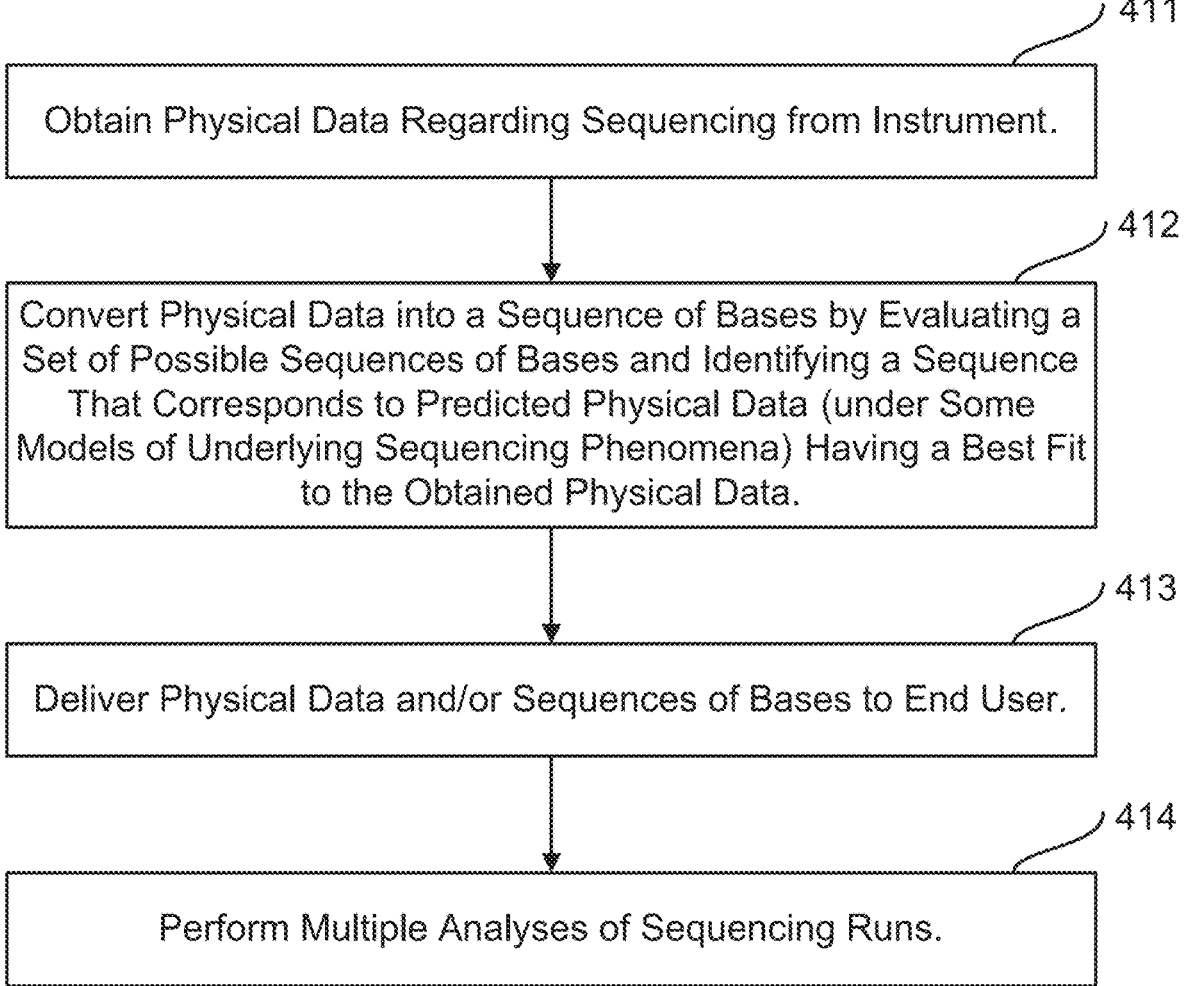

411

Obtain Physical Data Regarding Sequencing from Instrument.

412

Convert Physical Data into a Sequence of Bases by Evaluating a Set of Possible Sequences of Bases and Identifying a Sequence That Corresponds to Predicted Physical Data (under Some Models of Underlying Sequencing Phenomena) Having a Best Fit to the Obtained Physical Data.

413

Deliver Physical Data and/or Sequences of Bases to End User.

414

Perform Multiple Analyses of Sequencing Runs.

Select & Read
Raw Output Signal, RSi(j),
Of Microwell Mi

662

Neighbor
Definition

664

Read Neighboring
Raw Output Signals
RNk(j) k=1, 2, ... r

666

Compute An Average, A(j),
Of Neighboring
Raw Output Signals

668

Compute Output Signal
Si(j)=RSi(j)-A(j)

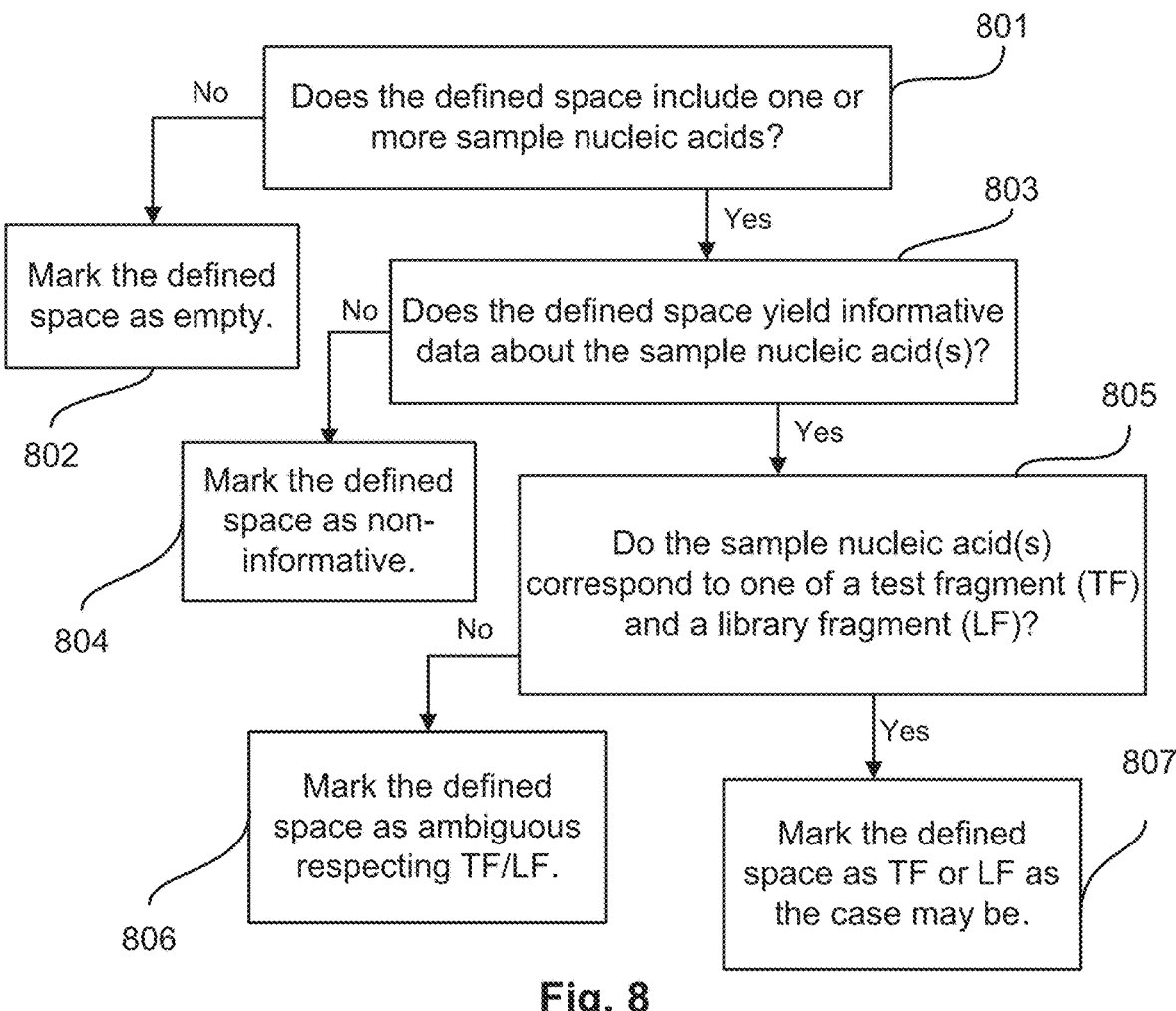

801

Does the defined space include one or more sample nucleic acids?

No

Mark the defined space as empty.

802

Yes

803

Does the defined space yield informative data about the sample nucleic acid(s)?

No

Mark the defined space as non-informative.

804

Yes

805

Do the sample nucleic acid(s) correspond to one of a test fragment (TF) and a library fragment (LF)?

No

Mark the defined space as ambiguous respecting TF/LF.

806

Yes

807

Mark the defined space as TF or LF as the case may be.

Fig. 8

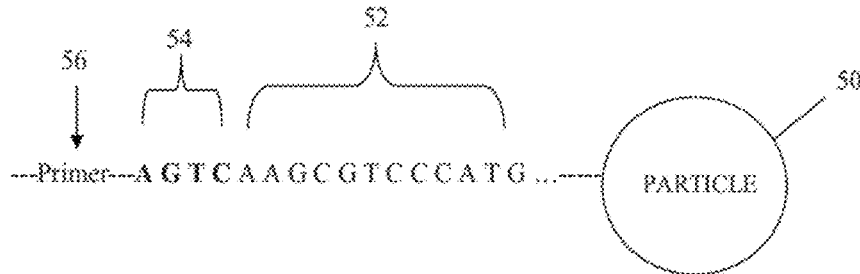

56     54     52     50

---Primer---A G T C A A G C G T C C A T G ...---     PARTICLE

Fig. 9

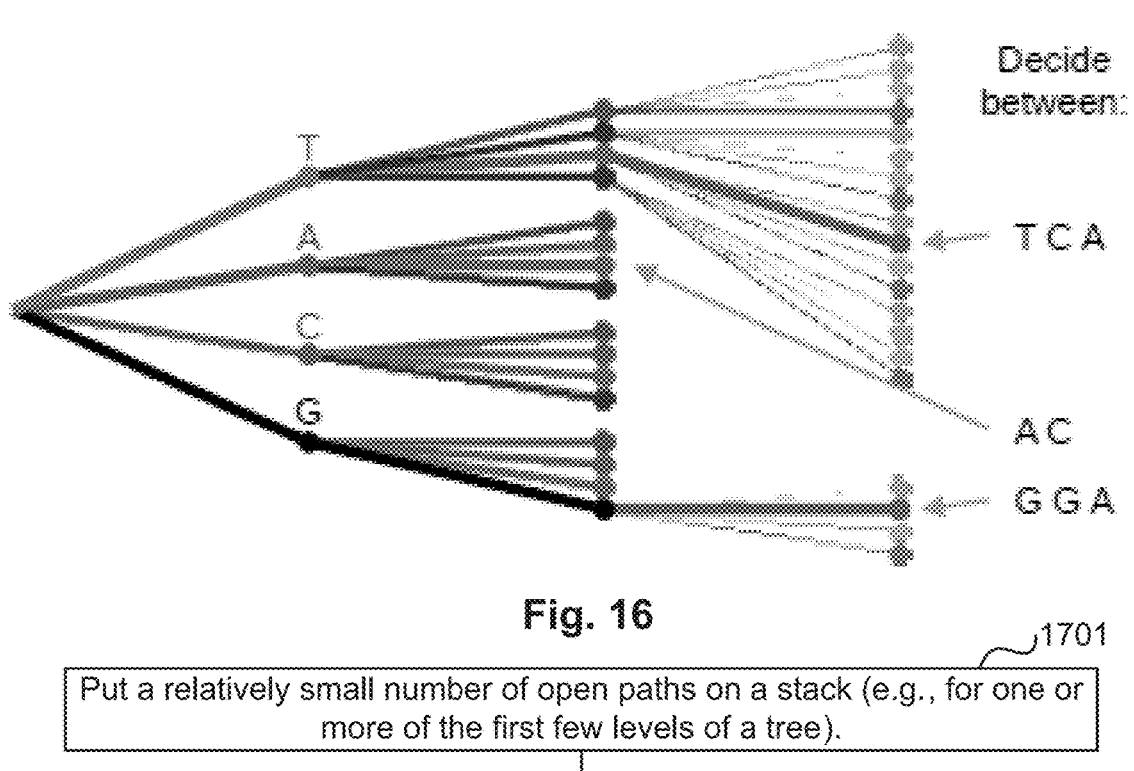

| Put a relatively small number of open paths on a stack (e.g., for one or more of the first few levels of a tree). |

1702

For every open path on the stack:

(1) calculate a set of predicted values (e.g., a predicted ionogram) for the four possible next path extensions from that path, (2) evaluate, for each of the four possible next path extensions and under some appropriate criterion, how good a fit there is between the set of predicted values and corresponding measured values, and (3) identify which of the four possible next path extensions has a best fit and, if the fit is good enough under some appropriate threshold, end that path and determine whether it is the best fitting path so far.

1703

Abandon the least promising paths on the stack to maintain a relatively small number of open paths in order to prevent overfitting and limit complexity.

Fig. 17

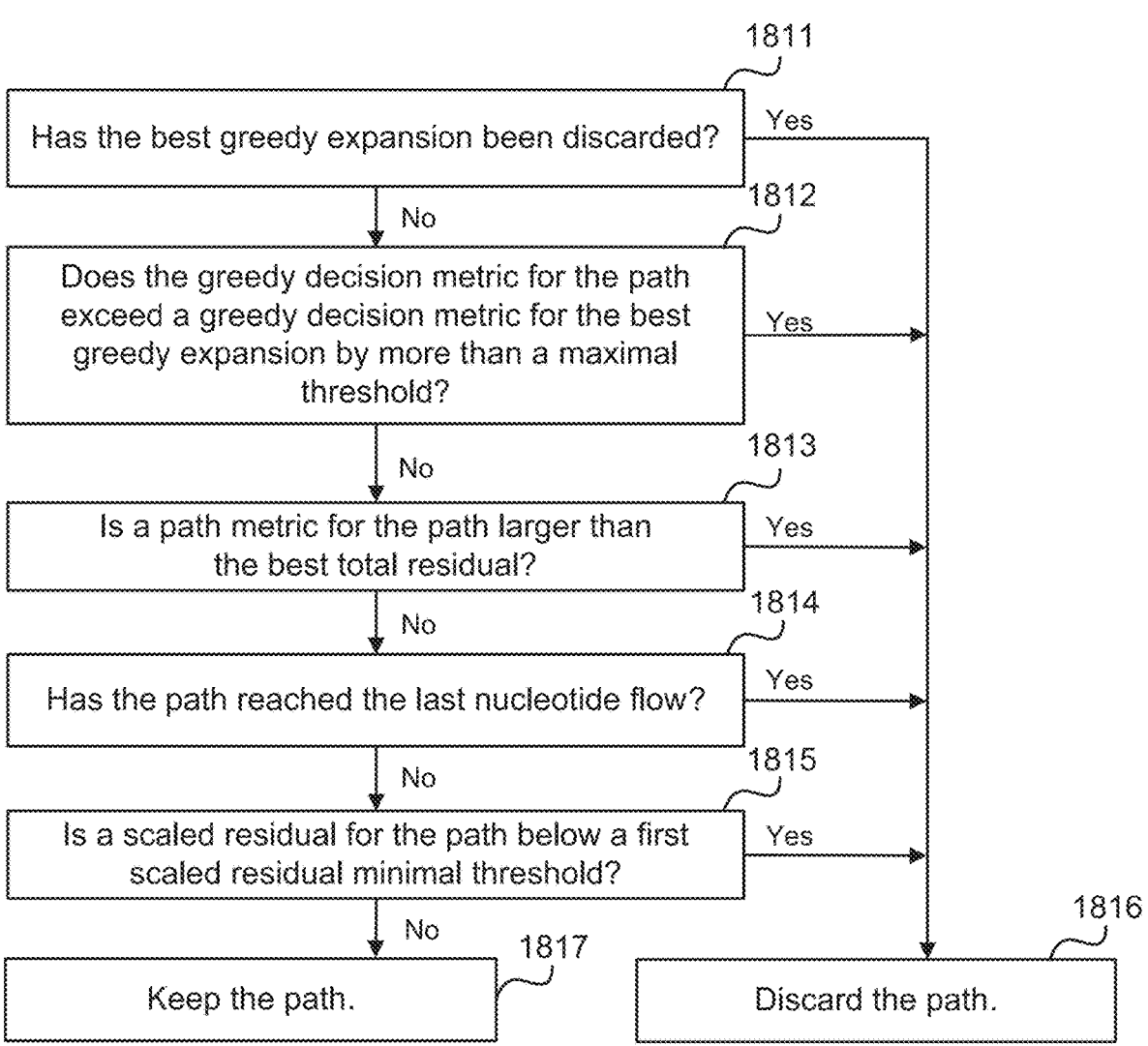

1811

Has the best greedy expansion been discarded?    Yes

No

1812

Does the greedy decision metric for the path exceed a greedy decision metric for the best greedy expansion by more than a maximal threshold?    Yes No

1813

Is a path metric for the path larger than the best total residual?    Yes

No

1814

Has the path reached the last nucleotide flow?    Yes

No

1815

Is a scaled residual for the path below a first scaled residual minimal threshold?    Yes No

1817

Keep the path.

1816

Discard the path.

Fig. 18B

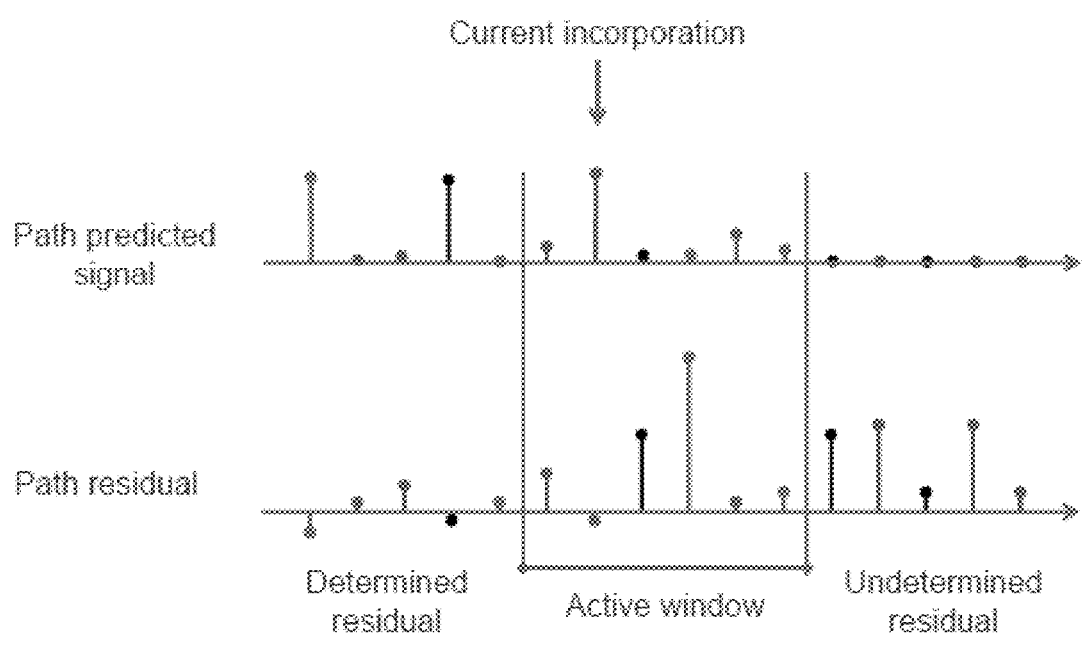
Fig. 19
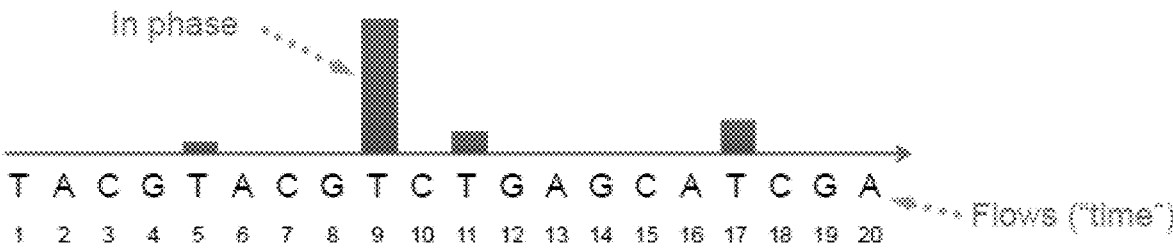
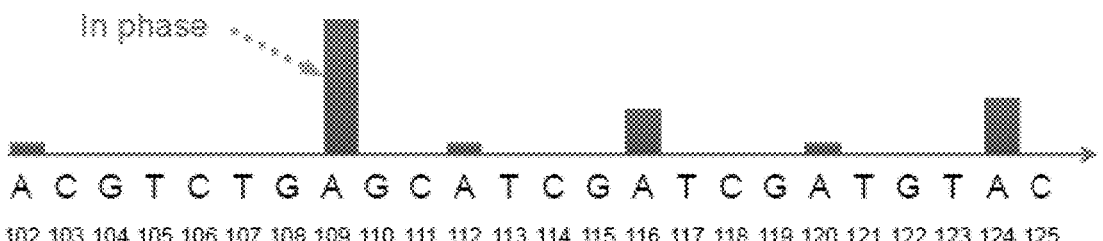
Fig. 20

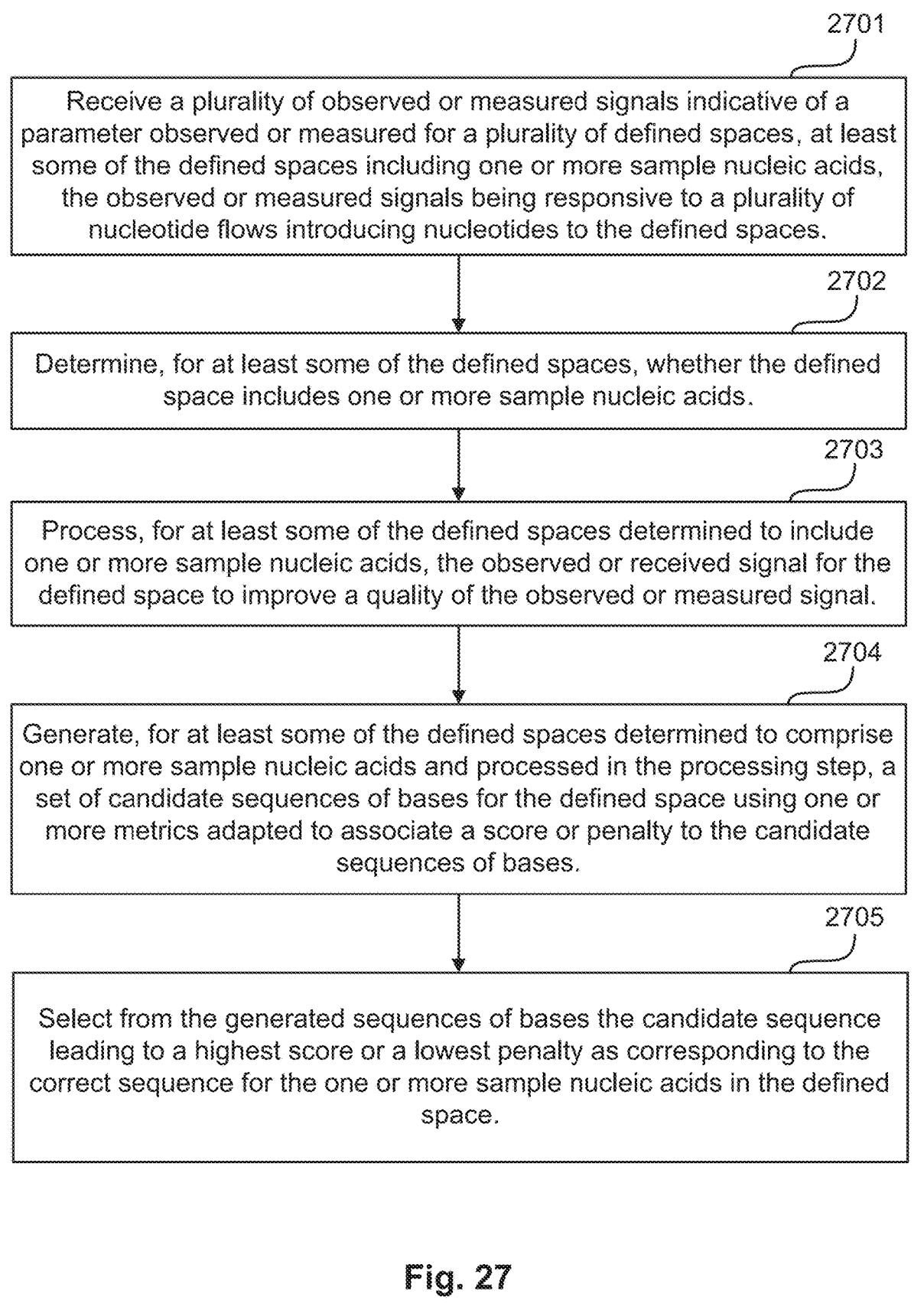

2701

Receive a plurality of observed or measured signals indicative of a parameter observed or measured for a plurality of defined spaces, at least some of the defined spaces including one or more sample nucleic acids, the observed or measured signals being responsive to a plurality of nucleotide flows introducing nucleotides to the defined spaces.

2702

Determine, for at least some of the defined spaces, whether the defined space includes one or more sample nucleic acids.

2703

Process, for at least some of the defined spaces determined to include one or more sample nucleic acids, the observed or received signal for the defined space to improve a quality of the observed or measured signal.

2704

Generate, for at least some of the defined spaces determined to comprise one or more sample nucleic acids and processed in the processing step, a set of candidate sequences of bases for the defined space using one or more metrics adapted to associate a score or penalty to the candidate sequences of bases.

2705

Select from the generated sequences of bases the candidate sequence leading to a highest score or a lowest penalty as corresponding to the correct sequence for the one or more sample nucleic acids in the defined space.

Fig. 27

Empirical vs Predicted Quality Score

METHODS, SYSTEMS, AND COMPUTER READABLE MEDIA FOR MAKING BASE CALLS IN NUCLEIC ACID SEQUENCING

CROSS-REFERENCE TO RELATED APPLICATIONS

This application is a continuation of U.S. application Ser. No. 16/196,502 filed Nov. 20, 2018, which is a continuation of U.S. application Ser. No. 13/588,408 filed Aug. 17, 2012, which is a continuation-in-part of both U.S. application Ser. No. 13/340,490 filed Dec. 29, 2011, and International application no. PCT/US2011/067959 filed Dec. 29, 2011, both of which claim priority to U.S. application No. 61/428,733 filed Dec. 30, 2010, all of which disclosures are herein incorporated by reference in their entirety. The U.S. application Ser. No. 13/588,408 also claims priority to U.S. application No. 61/525,073, filed Aug. 18, 2011, which is incorporated by reference herein in its entirety.

SEQUENCE LISTING

The instant application contains a Sequence Listing which has been submitted electronically in XML format and is hereby incorporated by reference in its entirety. Said XML copy, created on Nov. 16, 2022, is named TP103642USCON5_SL.xml and is 3,205 bytes in size.

FIELD

This application generally relates to methods, systems, and computer readable media for nucleic acid sequencing and, more specifically, to methods, systems, and computer readable media for making base calls using nucleic acid sequencing data and/or signals.

BACKGROUND

Various instruments, apparatuses, and/or systems for sequencing nucleic acids generate large volumes of sequencing data including, for example, the Genome Analyzer/HiSeq/MiSeq platforms (Illumina, Inc.: see. e.g., U.S. Pat. Nos. 6,833,246 and 5,750,341); the GS FLX, GS FLX Titanium, and GS Junior platforms (Roche/454 Life Sciences: see. e.g., Ronaghi et al., SCIENCE, 281:363-365 (1998), and Margulies et al., NATURE, 437:376-380 (2005)); and the Ion Personal Genome Machine (PGM™) (Life Technologies Corp./Ion Torrent: see. e.g., U.S. Pat. No. 7,948,015 and U.S. Pat. Appl. Publ. Nos. 2010/0137143, 2009/0026082, and 2010/0282617, which are all incorporated by reference herein in their entirety). In order to increase an overall throughput and base call accuracy of nucleic acid sequencing, among other objectives, there is a need for new methods, systems, and computer readable media that allow increases in accuracy, speed, and/or efficiency of processing and/or analyzing of large volumes of nucleic acid sequencing data and/or signals, especially in presence of effects capable of causing sequencing errors (such as, e.g., phasing effects).

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIG. 3 illustrates a system for evaluating sample nucleic acids including making base calls by processing and/or analyzing nucleic acid sequencing data.

FIG. 4 illustrates a method for evaluating sample nucleic acids including making base calls by processing and/or analyzing nucleic acid sequencing data.

FIG. 8 illustrates a method for classifying a content of a defined space.

FIG. 9 illustrates a particle associated with a sample nucleic acid template, a primer, and a sequencing key. FIG. 9 discloses SEQ ID NO: 1.

FIG. 12 discloses SEQ ID NO: 2.

FIG. 16 illustrates a decision point between various exemplary paths in a solver for making base calls.

FIG. 17 illustrates a method for stepwise progression through partial sequence paths in a base calling solver.

FIG. 18B illustrates a base calling pruning method including absolute pruning for another expansion than a best greedy expansion.

FIG. 19 illustrates a path predicted signal and a path residual.

FIG. 20 illustrates schematically a temporal model for modeling times at which a polymerase incorporates a nucleotide.

FIG. 27 illustrates a method of nucleic acid sequencing.

EXEMPLARY EMBODIMENTS

Figure 1:
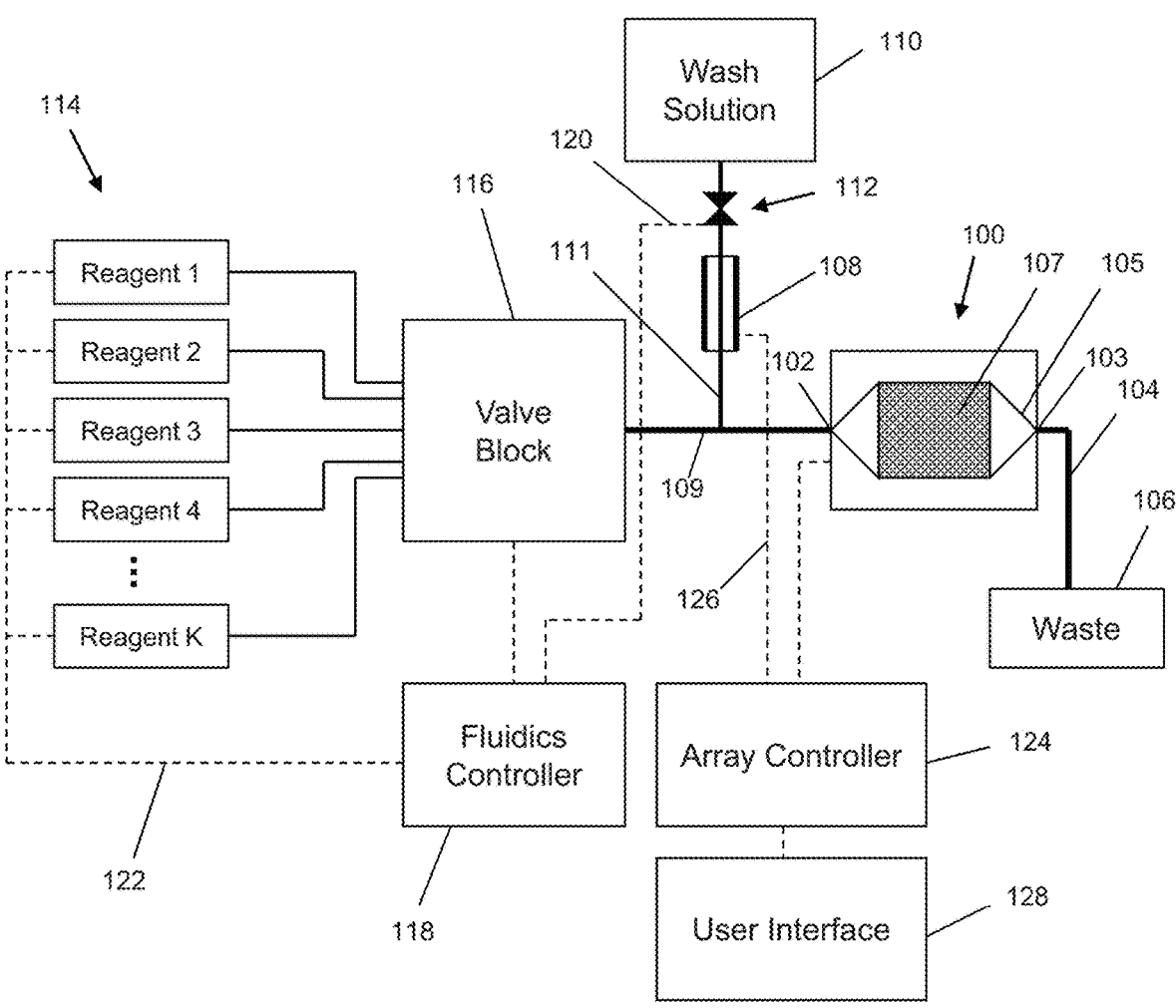
FIG. 1 illustrates components of a system for nucleic acid sequencing.

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

In accordance with the teachings and principles embodied in this application, new methods, systems, and computer readable media for making base calls by processing and/or analyzing data and/or signals that allow high-throughput sequencing of nucleic acid sequences with increased accuracy, speed, and/or efficiency, especially in presence of effects capable of causing sequencing errors (such as, e.g., phasing effects), are provided.

In this application, "amplifying" generally refers to performing an amplification reaction. In this application, "amplicon" generally refers to a product of a polynucleotide amplification reaction, which includes a clonal population of polynucleotides, which may be single stranded or double stranded and which may be replicated from one or more starting sequences. The one or more starting sequences may be one or more copies of the same sequence, or they may be a mixture of different sequences that contain a common region that is amplified such as, for example, a specific exon sequence present in a mixture of DNA fragments extracted from a sample. Preferably, amplicons may be formed by the amplification of a single starting sequence. Amplicons may be produced by a variety of amplification reactions whose products comprise replicates of one or more starting, or target, nucleic acids. Amplification reactions producing amplicons may be "template-driven" in that base pairing of reactants, either nucleotides or oligonucleotides, have complements in a template polynucleotide that are required for the creation of reaction products. Template-driven reactions may be primer extensions with a nucleic acid polymerase or oligonucleotide ligations with a nucleic acid ligase. Such reactions include, for example, polymerase chain reactions (PCRs), linear polymerase reactions, nucleic acid sequence-based amplifications (NASBAs), rolling circle amplifications, for example, including such reactions disclosed in the following references, which are all incorporated by reference herein in their entirety; Gelfand et al., U.S. Pat. No. 5,210,015: Kacian et al., U.S. Pat. No. 5,399, 491: Mullis, U.S. Pat. No. 4,683,202: Mullis et al., U.S. Pat. Nos. 4,683,195; 4,965,188; and 4,800,159; Lizardi, U.S. Pat. No. 5,854,033; and Wittwer et al., U.S. Pat. No. 6,174,670. In an exemplary embodiment, amplicons may be produced by PCRs. Amplicons may also be generated using rolling circle amplification to form a single body that may exclusively occupy a microwell as disclosed in Drmanac et al., U.S. Pat. Appl. Publ. No. 2009/0137404, which is incorporated by reference herein in its entirety.

In this application, "solid phase amplicon" generally refers to a solid phase support, such as a particle or bead, to which is attached a clonal population of nucleic acid sequences, which may have been produced by a process such as emulsion PCR, for example.

In this application, "analyte" generally refers to a molecule or biological cell that can directly affect an electronic sensor in a region (such as a defined space or reaction confinement region or microwell, for example) or that can indirectly affect such an electronic sensor by a by-product from a reaction involving such molecule or biological cell located in such region. In an exemplary embodiment, an analyte may be a sample or template nucleic acid, which may be subjected to a sequencing reaction, which may, in turn, generate a reaction by-product, such as one or more hydrogen ions, that can affect an electronic sensor. The term "analyte" also comprehends multiple copies of analytes, such as proteins, peptides, nucleic acids, for example, attached to solid supports, such as beads or particles, for example. In an exemplary embodiment, an analyte may be a nucleic acid amplicon or a solid phase amplicon. A sample nucleic acid template may be associated with a surface via covalent bonding or a specific binding or coupling reaction, and may be derived from, for example, a shot-gun fragmented DNA or amplicon library (which are examples of library fragments further discussed herein), or a sample emulsion PCR process creating clonally-amplified sample nucleic acid templates on particles such as IonSphere™ particles. An analyte may include particles having attached thereto clonal populations of DNA fragments, e.g., genomic DNA fragments, cDNA fragments, for example.

In this application, "primer" generally refers to an oligonucleotide, either natural or synthetic, that is capable, upon forming a duplex with a polynucleotide template, of acting as a point of initiation of nucleic acid synthesis and being extended from its 3' end along the template so that an extended duplex may be formed. Extension of a primer may be carried out with a nucleic acid polymerase, such as a DNA or RNA polymerase. The sequence of nucleotides added in the extension process may be determined by the sequence of the template polynucleotide. Primers may have a length in the range of from 14 to 40 nucleotides, or in the range of from 18 to 36 nucleotides, for example, or from N to M nucleotides where N is an integer larger than 18 and M is an integer larger than N and smaller than 36, for example. Other lengths are of course possible.

In this application, "oligonucleotide" generally refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, for example. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, for example. In an exemplary embodiment, oligonucleotide may refer to smaller polynucleotides, for example, having 5-40 monomeric units. Polynucleotides may include the natural deoxyribonucleosides (e.g., deoxyadenosine, deoxycytidine, deoxyguanosine, and deoxythymidine for DNA or their ribose counterparts for RNA) linked by phosphodiester linkages. However, they may also include non-natural nucleotide analogs, e.g., including modified bases, sugars, or internucleosidic linkages. In an exemplary embodiment, a polynucleotide may be represented by a sequence of letters (upper or lower case), such as "ATGCCTG," and it will be understood that the nucleotides are in 5'->3' order from left to right and that "A" denotes deoxyadenosine, "C" denotes deoxycytidine, "G" denotes deoxyguanosine, and "T" denotes deoxythymidine, and that "I" denotes deoxyinosine, and "U" denotes deoxyuridine, unless otherwise indicated or obvious from context.

In this application. "defined space" (or "reaction space," which may be used interchangeably with "defined space") generally refers to any space (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip. The area or volume may also be determined based on an amount of fluid or solid, for example, deposited on an area or in a volume otherwise defining a space. For example, isolated hydrophobic areas on a generally hydrophobic surface may provide defined spaces. In an exemplary embodiment, a defined space may be a reaction chamber, such as a well or a microwell, which may be in a chip. In an exemplary embodiment, a defined space may be a substantially flat area on a substrate without wells, for example. A defined space may contain or be exposed to enzymes and reagents used in nucleotide incorporation.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a substrate can permit the localization of a reaction of interest, and a discrete region of a surface of a substrate that has an affinity for or can specifically bind an analyte of interest (such as a discrete region with oligonucleotides or antibodies covalently linked to such surface), for example. Reaction confinement regions may have many configurations, for example, they may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may also be substantially flat areas on a substrate without wells, for example.

Defined spaces or reaction confinement regions may be arranged as an array, which may be a substantially planar one-dimensional or two-dimensional arrangement of elements such as sensors or wells. The number of columns (or rows) of a two-dimensional array may or may not be the same. Preferably, the array comprises at least 100,000 defined spaces or reaction confinement regions. Preferably, each space or region may be configured with a horizontal width and a vertical depth that has an aspect ratio of about 1:1 or less. For applications in which many thousands or more reactions are to be analyzed, the pitch between the reaction chambers may be configured to be no more than about 10 microns. In such applications, each reaction chamber may have a volume no greater than 0.34 pL, and more preferably no greater than 0.096 pL or even 0.012 pL in volume. Microwells may have any polygonal cross sections, including square, rectangular, or octagonal cross sections, for example, and may be arranged as a rectilinear array on a surface. Microwells may have hexagonal cross sections and be arranged as a hexagonal array, which permits a higher density of microwells per unit area than rectilinear arrays. An array of defined spaces or reaction confinement regions may be an array of discrete areas on a substantially flat substrate without wells.

A plurality of defined spaces or reaction confinement regions may be arranged in an array, and each defined space or reaction confinement regions may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal. The structure and/or design of sensors for use with the present teachings may vary widely and may include one or more features of the following references, which are all incorporated by reference herein in their entirety: Barbaro et al., U.S. Pat. No. 7,535,232: Esfandyarpour et al., U.S. Pat. Appl. Publ. No. 2008/0166727: Kamahori et al., U.S. Pat. Appl. Publ. No. 2007/0059741: Miyahara et al., U.S. Pat. Appl. Publ. Nos. 2008/0286767 and 2008/0286762: O'uchi, U.S. Pat. Appl. Publ. No. 2006/0147983: Osaka et al., U.S. Pat. Appl. Publ. No. 2007/0207471: Rothberg et al., U.S. Pat. Appl.

Publ. No. 2009/0127589; Rothberg et al., U.K. Pat. Appl. No. GB 2461127; and Sawada et al., U.S. Pat. No. 7,049, 645.

In this application, "reaction mixture" generally refers to a solution containing any necessary reactants for performing a reaction, which may include, for example, buffering agents to maintain pH at a selected level during a reaction, salts, enzymes, co-factors, scavengers, etc., for example.

In this application, "microfluidics device" generally refers to an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, etc. Microfluidics devices may further include valves, pumps, and specialized functional coatings on interior walls, e.g., to prevent adsorption of sample components or reactants, facilitate reagent movement by electroosmosis, etc. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device may have cross-sectional dimensions of less than a few hundred square micrometers, for example, and passages may have capillary dimensions, e.g., having maximal cross-sectional dimensions of from about 500 μm to about 0.1 μm, for example. Microfluidics devices may have volume capacities in the range of from 1 μL to a few nL, e.g., 10-100 nL, for example.

In various exemplary embodiments, there are provided methods, systems, and computer readable media for evaluating sample nucleic acid sequences including making base calls by processing and/or analyzing data and/or signals that allow high-throughput sequencing of nucleic acid sequences with increased accuracy, speed, and/or efficiency, especially in presence of effects capable of causing sequencing errors (such as, e.g., phasing effects). The methods, systems, and computer readable media may include steps and/or structural elements for receiving raw data and/or signals, processing the raw data and/or signals using various protocols and modules, and outputting or storing any results in various formats. In an exemplary embodiment, the results may be further processed or analyzed by other methods, systems, and computer readable media.

In various exemplary embodiments, the methods, systems, and computer readable media described herein may advantageously be used to process and/or analyze data and signals obtained from electronic or charged-based nucleic acid sequencing. In electronic or charged-based sequencing (such as, e.g., pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured signals indicative of ion concentration during each nucleotide flow, the identity of the type, sequence and number of nucleotide(s) associated with a sample nucleic acid present in a reaction chamber can be determined.

FIG. 1 illustrates components of a system for nucleic acid sequencing according to an exemplary embodiment. The components include a flow cell and sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a microwell array 107, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100. The fluidics controller 118 may control driving forces for the reagents 114 and the operation of valve 112 and valve block 116 with suitable software. The microwell array 107 may include an array of defined spaces or reaction confinement regions, such as microwells, for example, that is operationally associated with a sensor array so that, for example, each microwell has a sensor suitable for detecting an analyte or reaction property of interest. The microwell array 107 may preferably be integrated with the sensor array as a single device or chip. The flow cell may have a variety of designs for controlling the path and flow rate of reagents over the microwell array 107, and may be a microfluidics device. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls.

In an exemplary embodiment, such a system may deliver reagents to the flow cell and sensor array 100 in a predetermined sequence, for predetermined durations, at predetermined flow rates, and may measure physical and/or chemical parameters providing information about the status of one or more reactions taking place in defined spaces or reaction confinement regions, such as, for example, microwells (or in the case of empty microwells, information about the physical and/or chemical environment therein). In an exemplary embodiment, the system may also control a temperature of the flow cell and sensor array 100 so that reactions take place and measurements are made at a known, and preferably, a predetermined temperature.

In an exemplary embodiment, such a system may be configured to let a single fluid or reagent contact the reference electrode 108 throughout an entire multi-step reaction. The valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

Figures 2A, 2B:
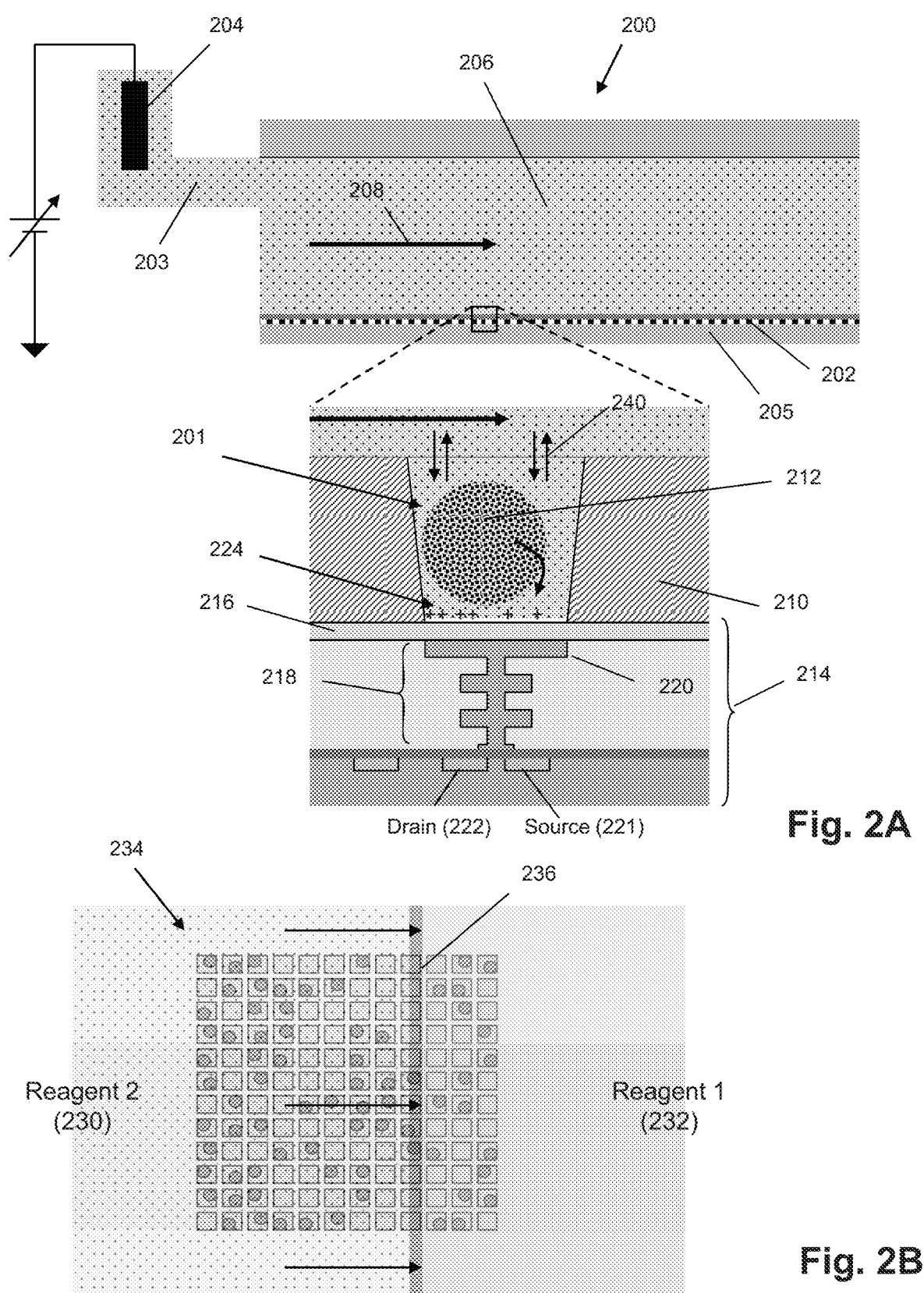
FIG. 2A illustrates cross-sectional and expanded views of a flow cell for nucleic acid sequencing.
FIG. 2B illustrates a uniform flow front between successive reagents moving across a section of a microwell array.

FIG. 2A illustrates cross-sectional and expanded views of a flow cell 200 for nucleic acid sequencing according to an exemplary embodiment. The flow cell 200 includes a microwell array 202, a sensor array 205, and a flow chamber 206 in which a reagent flow: 208 may move across a surface of the microwell array 202, over open ends of microwells in the microwell array 202. A microwell 201 in the microwell array 202 may have any suitable volume, shape, and aspect ratio, which may be selected depending on one or more of any reagents, by-products, and labeling techniques used, and the microwell 201 may be formed in layer 210, for example, using any suitable microfabrication technique. A sensor 214 in the sensor array 205 may be an ion sensitive (ISFET) or a chemical sensitive (chemFET) sensor with a floating gate 218 having a sensor plate 220 separated from the microwell interior by a passivation layer 216, and may be predominantly responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into microwells primarily by diffusion 240. One or more analytical reactions to identify or determine characteristics or properties of an analyte of interest may be carried out in one or more microwells of the microwell array 202. Such reactions may generate directly or indirectly by-products that affect the amount of charge 224 adjacent to the sensor plate 220.

In an exemplary embodiment, a reference electrode 204 may be fluidly connected to the flow chamber 206 via a flow passage 203. In an exemplary embodiment, the microwell array 202 and the sensor array 205 may together form an integrated unit forming a bottom wall or floor of the flow cell 200. In an exemplary embodiment, one or more copies of an analyte may be attached to a solid phase support 212, which may include microparticles, nanoparticles, beads, gels, and may be solid and porous, for example. The analyte may include a nucleic acid analyte, including a single copy and multiple copies, and may be made, for example, by rolling circle amplification (RCA), exponential RCA, or other suitable techniques to produce an amplicon without the need of a solid support.

FIG. 2B illustrates a uniform flow front between successive reagents moving across a section 234 of a microwell array according to an exemplary embodiment. A "uniform flow front" between first reagent 232 and second reagent 230 generally refers to the reagents undergoing little or no mixing as they move, thereby keeping a boundary 236 between them narrow. The boundary may be linear for flow cells having inlets and outlets at opposite ends of their flow chambers, or it may be curvilinear for flow cells having central inlets (or outlets) and peripheral outlets (or inlets). In an embodiment, the flow cell design and reagent flow rate may be selected so that each new reagent flow with a uniform flow front as it transits the flow chamber during a switch from one reagent to another.

Figure 2C:
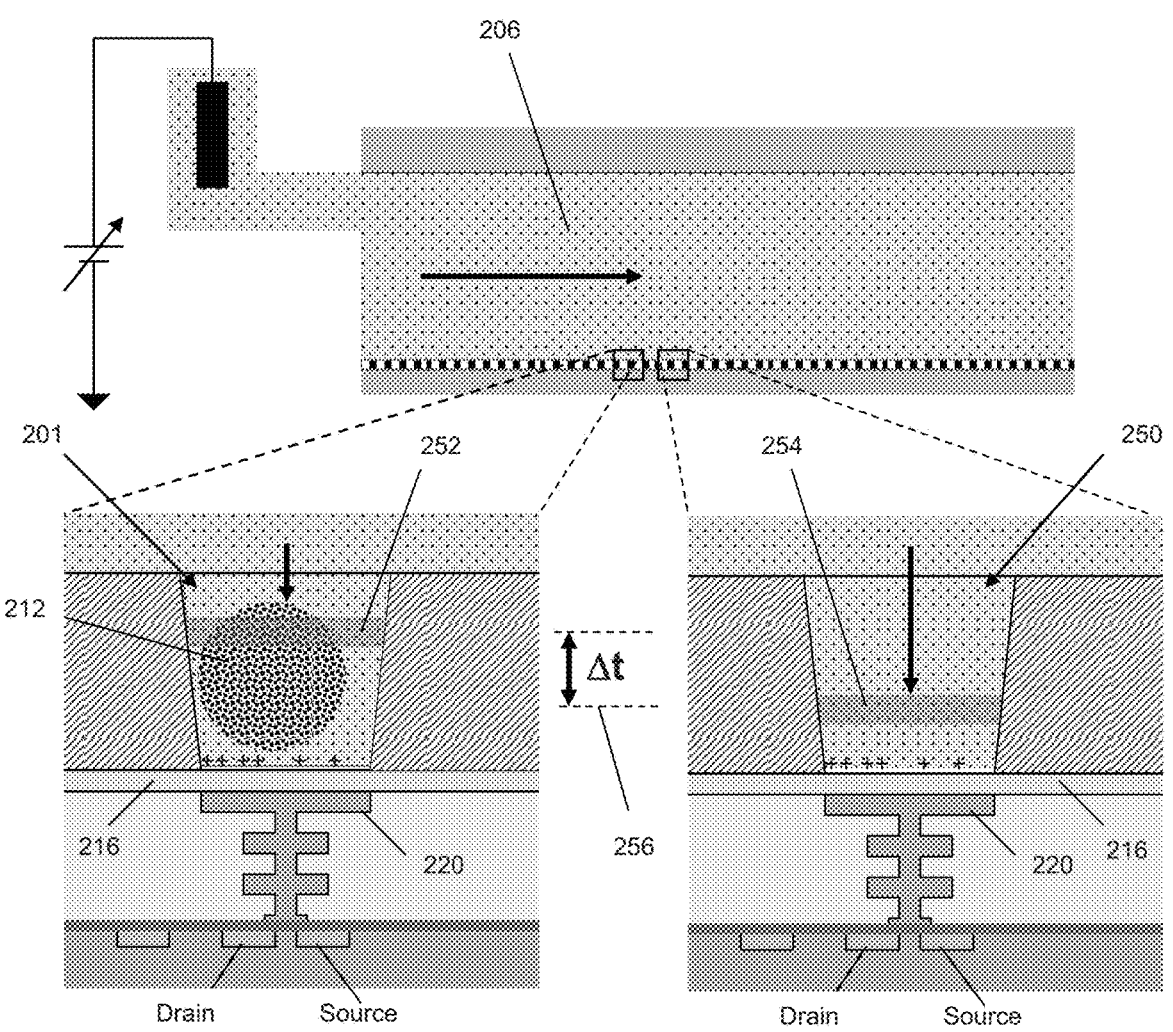
FIG. 2C illustrates a time delay associated with a diffusion of a reagent flow from a flow chamber to a microwell that contains an analyte and/or particle and to an empty microwell.

FIG. 2C illustrates a time delay associated with a diffusion of a reagent flow from a flow chamber 206 to a microwell 201 that contains an analyte and/or particle 212 and to an empty microwell 250 according to an exemplary embodiment. The charging reagent flow may diffuse to the passivation layer 216 region opposite of the sensor plate 220. However, a diffusion front 252 of the reagent flow in the microwell 201 containing an analyte and/or particle 212 is delayed relative to a diffusion front 254 of the reagent flow in the empty well 250, either because of a physical obstruction due to the analyte/particle or because of a buffering capacity of the analyte/particle.

In an exemplary embodiment, a correlation between an observed time delay in a change of output signal and the presence of an analyte/particle may be used to determine whether a microwell contains an analyte. To observe the time delay, the pH may be changed using a charging reagent from a first predetermined pH to a different pH, effectively exposing the sensors to a step-function change in pH that will produce a rapid change in charge on the sensor plates. The pH change between the first reagent and the charging reagent (which may sometimes be referred to herein as the "second reagent" or the "sensor-active" reagent) may be 2.0 pH units or less. 1.0 pH unit or less, 0.5 pH unit or less, or 0.1 pH unit or less, for example. The changes in pH may be made using conventional reagents, including HCl, NaOH, for example, at concentrations for DNA pH-based sequencing reactions in the range of from 5 to 200 μM, or from 10 to 100 μM, for example.

Figure 2D:
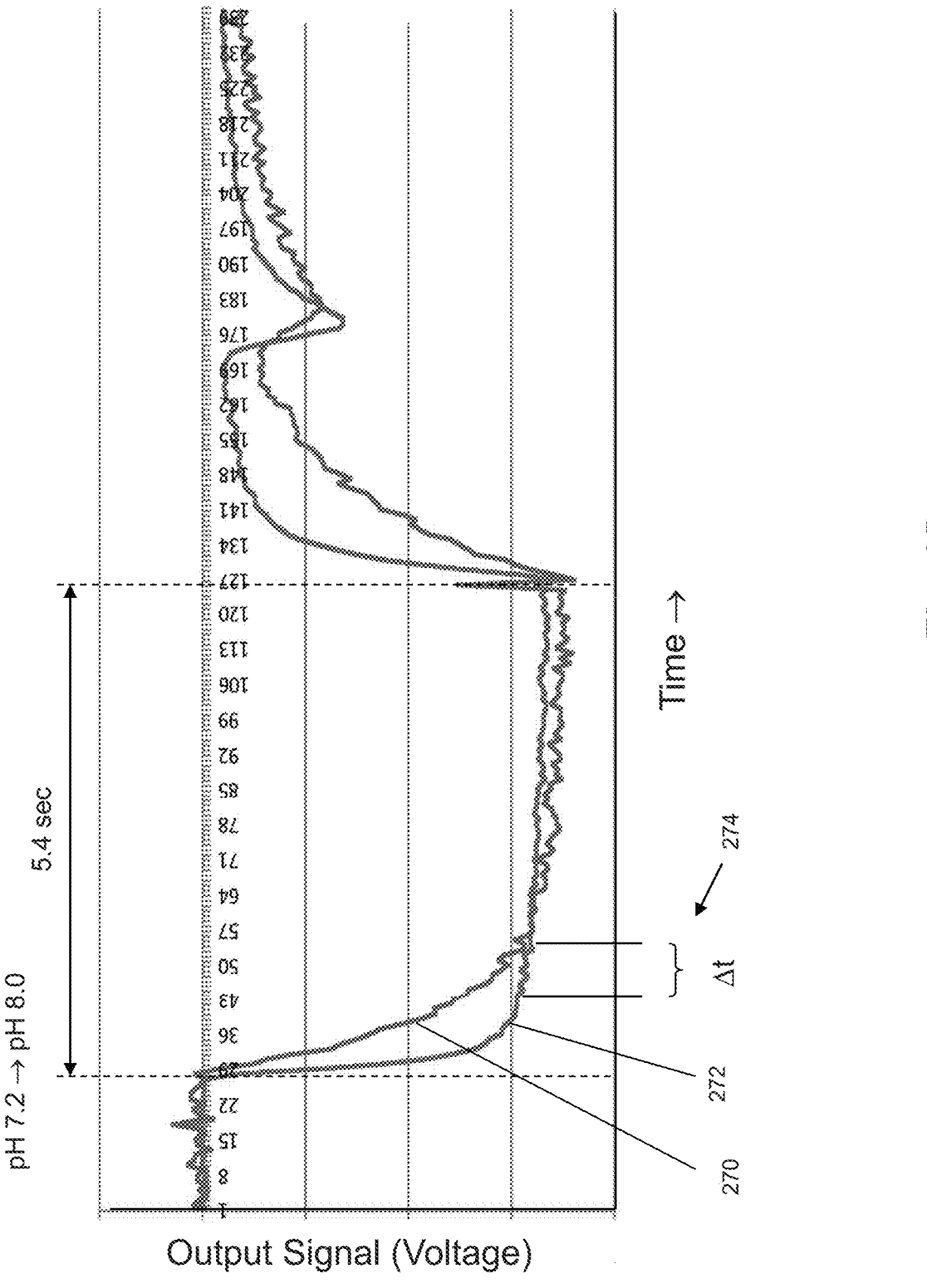
FIG. 2D illustrates a comparison between an output signal from a microwell with a particle and an output signal from a microwell without a particle following a pH.

FIG. 2D illustrates a comparison between an output signal from a microwell with a particle and an output signal from a microwell without a particle following a pH change according to an exemplary embodiment. Curve 270 shows an output signal from a first sensor corresponding to a microwell loaded bead with template, primer, and polymerase attached. Curve 272 shows an output signal from a second sensor corresponding to an empty microwell. The output signals follow a change from pH 7.2 to pH 8.0. Both curves show an abrupt change from a high value corresponding to pH 7.2 to a low value corresponding to pH 8.0. However, the output signal corresponding to the empty microwell reaches the low value noticeably faster than the output signal corresponding to the loaded microwell. The difference in time, Δt 274, at which the respective output signals reach the lower value (or a comparable measure) may be determined with any suitable data analysis techniques, and may be used to determine whether a microwell contains an analyte and/or particle.

FIG. 3 illustrates a system for evaluating sample nucleic acids including making base calls by processing and/or analyzing nucleic acid sequencing data according to an exemplary embodiment. The system includes a sequencing instrument 301, a server 302 or other computing means or resource, and one or more end user computers 305 or other computing means or resource, and may also include other user computers/servers/networks 306. The server 302 may include a processor 303 and a memory and/or database 304. The sequencing instrument 301 and the server 302 may include one or more computer readable media for making base calls by processing and/or analyzing nucleic acid sequencing data. One or more of these components may be used to perform or implement one or more aspects of the exemplary embodiments described herein.

FIG. 4 illustrates a method for evaluating sample nucleic acids including making base calls by processing and/or analyzing nucleic acid sequencing data according to an exemplary embodiment. In step 411, a user obtains physical data by performing a sequencing task using a sequencing instrument. The physical data may include voltage data indicative of hydrogen ion concentrations, for example. In step 412, a server or other computing means or resource converts the physical data into sequences of bases by, for example, evaluating a set of possible sequences of bases and identifying a sequence that corresponds to predicted physical data (under some models of underlying sequencing phenomena) having a best fit to the obtained physical data. In step 413, the server or other computing means or resource delivers the physical data and/or sequences of bases to an end user. In step 414, if many runs of physical data and/or sequences of bases have been performed, other users and/or entities may perform multiple analyses of sequencing runs. One or more of these steps and/or components may be used to perform or implement one or more aspects of the exemplary embodiments described herein.

Figures 5A, 5B, 5C:
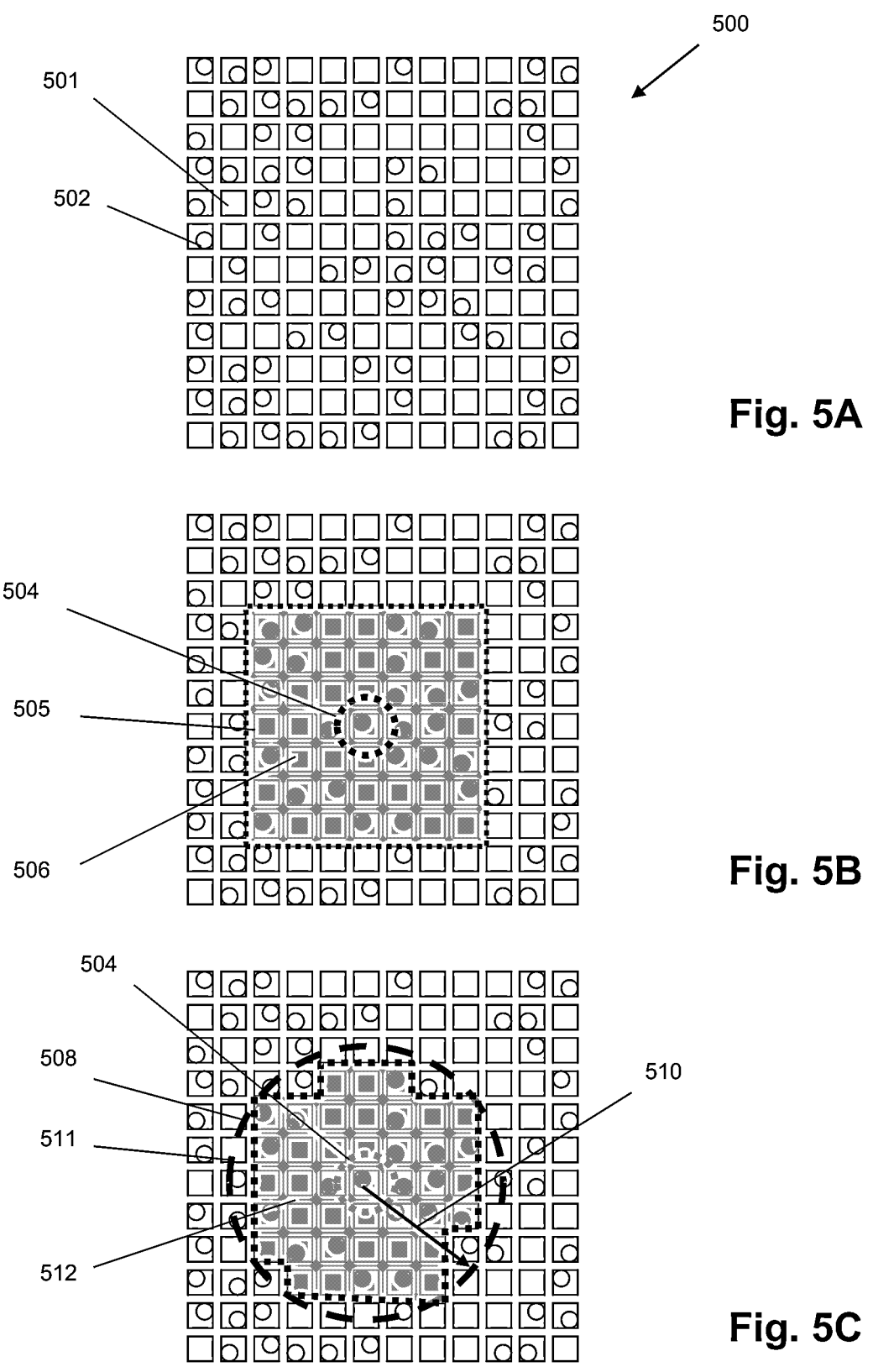
FIG. 5A illustrates an array section including empty microwells and analyte-containing microwells.
FIGS. 5B and 5C illustrate alternative ways of defining a set of empty microwells in the vicinity of a selected microwell.

FIG. 5A illustrates an array section 500 including empty microwells 501 and analyte-containing microwells 502 according to an exemplary embodiment. The analytes may be randomly distributed among the microwells, and may include beads, for example.

In an exemplary embodiment, output signals collected from empty wells may be used to reduce or subtract noise in output signals collected from analyte-containing wells to improve a quality of such output signals. Such reduction or subtraction may be done using any suitable signal processing techniques. The noise component may be measured based on an average of output signals from multiple neighboring empty wells that may be in a vicinity of a well of interest, which may include weighted averages and functions of averages, for example, based on models of physical and chemical processes taking place in the wells.

In an exemplary embodiment, alternatively or in addition to neighboring empty wells, other sets of wells may be analyzed to characterize noise even better, which may include wells containing particles without an analyte, for example. The noise component or averages may be processed in various ways, including converting time domain functions of average empty well noise to frequency domain representations and using Fourier analysis to remove common noise components from output signals from non-empty wells.

FIGS. 5B and 5C illustrate alternative ways of defining a set of empty microwells in the vicinity of a selected microwell according to an exemplary embodiment. In FIG. 5B, the empty wells to be used are from a fixed region 506 defined by a 7×7 square region of wells 505 for each selected microwell 504. Such a fixed region may vary in the range from 2×2 to 101×101, or in the range from AxA to BxB where A is an integer larger than 2 and B is an integer larger than A and smaller than 101, or in the range from 3×3 to 25×25, for example, or it may be larger in size and may not necessarily be square in shape and could be rectangular, for example. In FIG. 5C, the empty wells to be used may be those wells 508 falling entirely within a circular region 512 defined by a circle 511 having a given radius 510 centered on selected microwell 504. Although all such wells 508 may be used, in some embodiments only a subset of them may actually be used. For example, when analytes or particles are sparsely present (e.g., in less than 25% of the wells), only a portion of the empty wells in a defined region (e.g., 512), which may be a random sample, may be used. The size of such regions may be selected depending on several factors, including a degree of analyte loading, and an availability of computing time/resources, for example.

In an exemplary embodiment, an area and/or number of wells selected for determining an average empty well signal may change according to the density of analytes in the wells.

For example, if a minimum of $N$ *empty* well output signals, e.g., 10, 20, or 30, must be measured to ensure a reliable representation of local noise, then a local region, e.g., 512, may be increased until it contains the necessary number of empty wells. In an exemplary embodiment, local noise may be removed using a fixed area whenever ninety-five percent or less of the wells in an array contain an analyte.

Figure 6A:
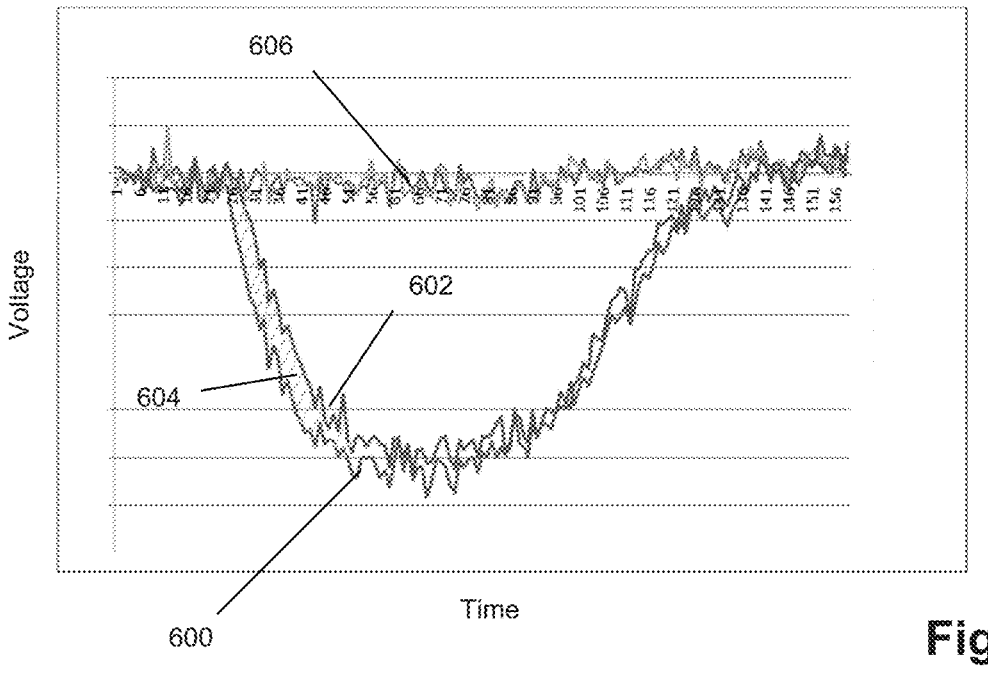
FIG. 6A illustrates various output signals obtained from different wells in response to a reagent change in a pH-based sequencing operation.

FIG. 6A illustrates various output signals obtained from different wells in response to a reagent change in a pH-based sequencing operation according to an exemplary embodiment. Curves 606 show signals from wells during a wash step with no changes in reagent. Curve 600 shows an output signal from a well containing a particle with template attached where a primer has been extended by one nucleotide. Curve 602 shows an output signal from a well that contains a particle with a template where there has been no extension. Region 604 shows the difference between signals 602 and 604 that is due to the nucleotide extension. This shows another source of noise (e.g., reagent change noise), which may arise with successive reagent flows. The magnitude of such noise may depend on several factors, including the nature of the measurement being made (e.g., pH, inorganic pyrophosphate (PPi), or other ions), whether a leading or trailing reagent in a reagent change has a property or constituent (e.g., pH) that affects sensor performance and the magnitude of the influence, the relative magnitude of the reagent change effect in comparison with the reaction signal being monitored, etc.

Figure 6B:
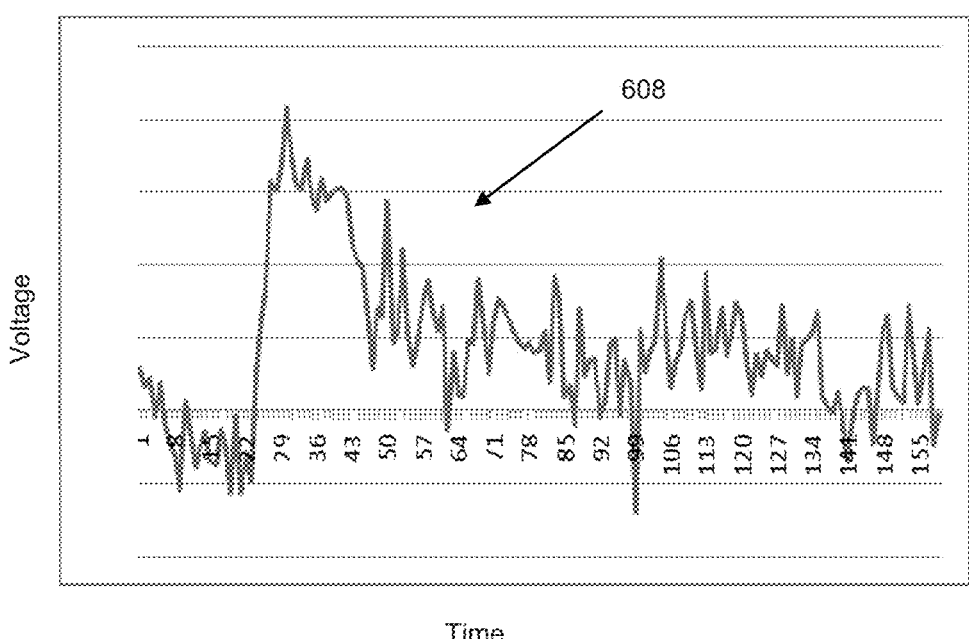
FIG. 6B illustrates a part of an output signal due to a nucleotide incorporation.

FIG. 6B illustrates a part of an output signal due to a nucleotide incorporation according to an exemplary embodiment. Curve 608 corresponds to the difference between curves 600 and 602 of FIG. 6A, which corresponds to the part of the raw output signal of curve 600 that is due to the production of an hydrogen ion in the extension reaction. Such reagent change noise (and other noise components common to local groups of wells) may be removed or subtracted from an output signal of a selected well by using output signals of one or more neighboring wells (which may include average values), which may include empty wells and/or non-empty wells where no extension reaction took place. Correction of raw output signals by removal or subtraction of reagent change noise may be carried out after each reagent change based on averages computed after each such change, or using averages from a previous reagent change, depending on the rate at which averages change during a multi-step or multi-cycle electrochemical process, for example. An average may be computed for each different dNTP flow in a sequencing cycle and used to correct raw output signals for from 1 to 5 cycles of reagent change, for example.

Figure 6C:
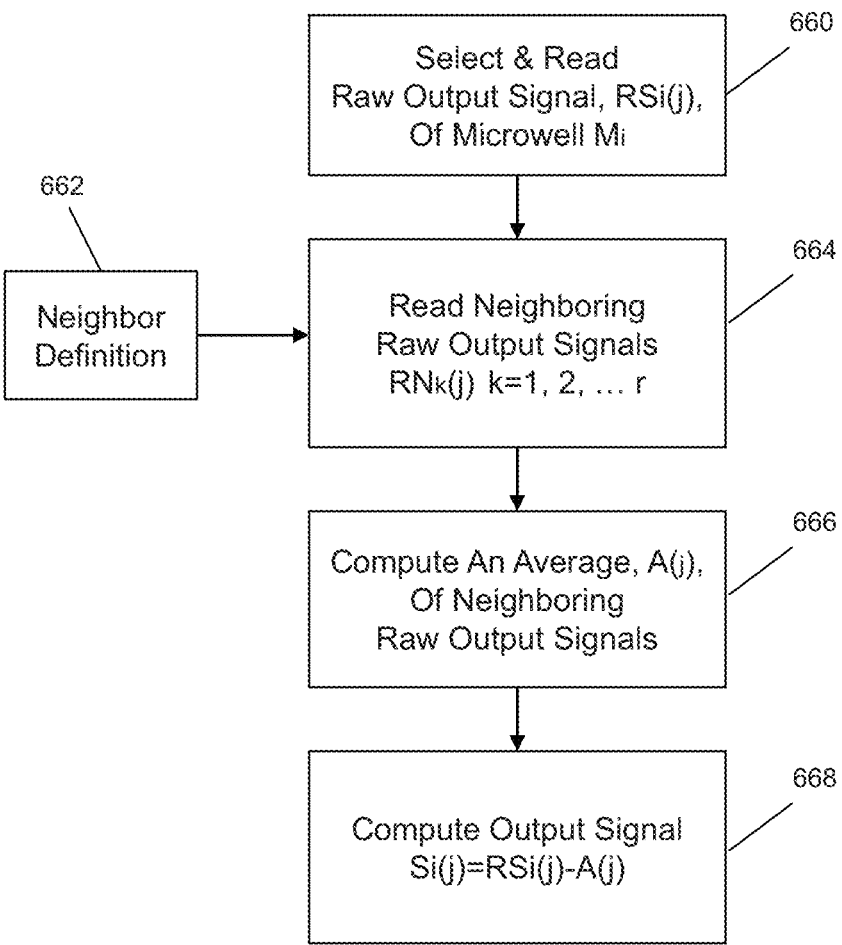
FIG. 6C illustrates a method for removing reagent change noise from a signal.

FIG. 6C illustrates a method for removing reagent change noise from a signal according to an exemplary embodiment. In step 660, a raw output signal $RS_i$ (j) for times j=1, 2 . . . t and selected well $M_i$ is recorded by a sensor. The raw output signal may represent recorded values of the output signal prior to downstream data processing and/or analysis. In step 662, neighboring wells are defined, which may include definition of a local region as described in FIGS. 5B and 5C, for example, for empty wells or wells with analyte or particle but no reaction, for example. In step 664, raw output signals of neighboring wells $RN_K$ (j) for selected neighbors k=1, 2, . . . r are read. The neighboring output signals may be selected from neighboring wells that are physically and chemically similar to the $M_i$ well, except for the presence of a signal from the analyte that is to be detected or measured. In step 666, an average A (j) is computed for the neighboring raw output signals. The average may include weighted averages or transforms of average raw output signals of the neighboring wells to reflect the different physical and chemical conditions of the selected well and its neighbors. In step 668, the average A (j) is subtracted from the raw output signal RSi (j) to yield a noise-reduced output signal Si (j).

In an exemplary embodiment, the signal delay shown in FIG. 2D that may permit the detection of empty wells may be accounted for with an appropriate signal transformation in a noise removal process, and an empty well signal may accordingly be modified to account for the absence of a particle and related chemical interactions (including, e.g., an absence of delay and flattening that would occur in an analyte-containing well).

Figure 6D:
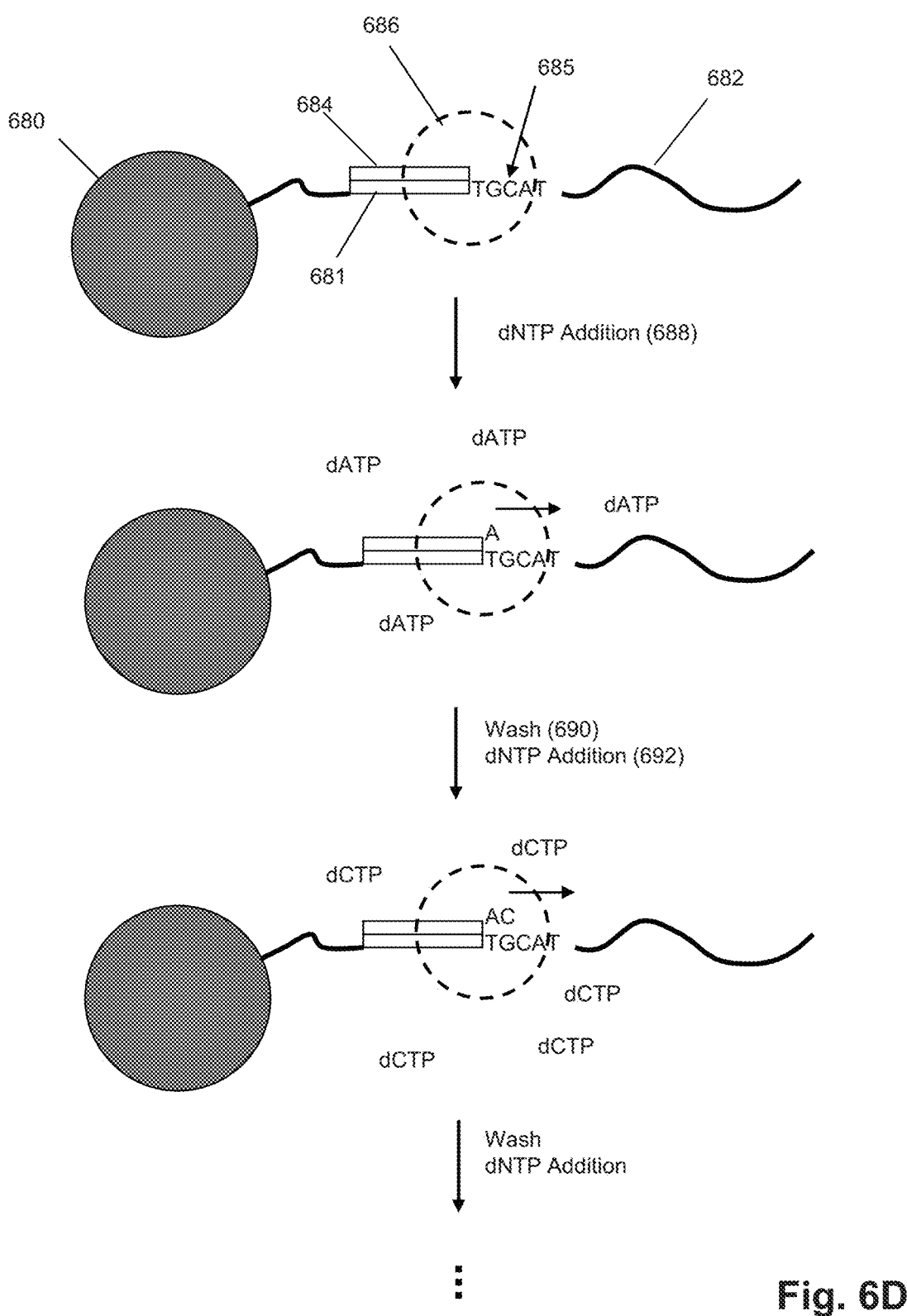
FIG. 6D illustrates schematically a process for label-free, pH-based sequencing.

FIG. 6D illustrates schematically a process for label-free, pH-based sequencing according to an exemplary embodiment. A template 682 with a primer binding site 681 are attached to a solid phase support 680. The template 682 may be attached as a clonal population to a solid support, such as a microparticle or bead, for example, and may be prepared as disclosed in U.S. Pat. No. 7,323,305, which is incorporated by reference herein in its entirety. A primer 684 and DNA polymerase 686 are operably bound to the template 682. As used herein, "operably bound" generally refers to a primer being annealed to a template so that the primer's 3' end may be extended by a polymerase and that a polymerase is bound to such primer-template duplex (or in close proximity thereof) so that binding and/or extension may take place when dNTPs are added. In step 688, dNTP (shown as dATP) is added, and the DNA polymerase 686 incorporates a nucleotide "A" (since "T" is the next nucleotide in the template 682). In step 690, a wash is performed. In step 692, the next dNTP (shown as dCTP) is added, and the DNA polymerase 686 incorporates a nucleotide "C" (since "G" is the next nucleotide in the template 682). The pH-based nucleic acid sequencing, in which base incorporations may be determined by measuring hydrogen ions that are generated as natural by-products of polymerase-catalyzed extension reactions, may be performed using at least in part one or more features of Anderson et al., Sensors and Actuators B Chem., 129:79-86 (2008): Rothberg et al., U.S. Pat. Appl. Publ. No. 2009/0026082; and Pourmand et al., Proc. Natl. Acad. Sci., 103:6466-6470 (2006), which are all incorporated by reference herein in their entirety. In an exemplary embodiment, after each addition of a dNTP, an additional step may be performed in which the reaction chambers are treated with a dNTP-destroying agent, such as apyrase, to eliminate any residual dNTPs remaining in the chamber that might result in spurious extensions in subsequent cycles.

The output signals measured throughout this process depend on the number of nucleotide incorporations. Specifically, in each addition step, the polymerase extends the primer by incorporating added dNTP only if the next base in the template is complementary to the added dNTP. If there is one complementary base, there is one incorporation: if two, there are two incorporations: if three, there are three incorporations, and so on. With each incorporation, an hydrogen ion is released, and collectively a population released hydrogen ions change the local pH of the reaction chamber. The production of hydrogen ions is monotonically related to the number of contiguous complementary bases in the template (as well as to the total number of template molecules with primer and polymerase that participate in an extension reaction). Thus, when there is a number of contiguous identical complementary bases in the template (which may represent a homopolymer region), the number of hydrogen ions generated and thus the magnitude of the local pH change is proportional to the number of contiguous identical complementary bases (and the corresponding output signals are then sometimes referred to as "1-mer." "2-mer." "3-mer" output signals, etc.). If the next base in the template is not complementary to the added dNTP, then no incorporation occurs and no hydrogen ion is released (and the output signal is then sometimes referred to as a "0-mer" output signal). In each wash step of the cycle, an unbuffered wash solution at a predetermined pH may be used to remove the dNTP of the previous step in order to prevent misincorporations in later cycles. In an exemplary embodiment, the four different kinds of dNTP are added sequentially to the reaction chambers, so that each reaction is exposed to the four different dNTPs, one at a time. In an exemplary embodiment, the four different kinds of dNTP are added in the following sequence: dATP, dCTP, dGTP, dTTP, dATP, dCTP, dGTP, dTTP, etc., with each exposure followed by a wash step. Each exposure to a nucleotide followed by a washing step can be considered a "nucleotide flow." Four consecutive nucleotide flows can be considered a "cycle." For example, a two cycle nucleotide flow order can be represented by: dATP, dCTP, dGTP, dTTP, dATP, dCTP, dGTP, dTTP, with each exposure being followed by a wash step. Different flow orders are of course possible.

In an exemplary embodiment, template 682 may include a calibration sequence 685 that provides a known signal in response to the introduction of initial dNTPs. The calibration sequence 685 preferably contains at least one of each kind of nucleotide, may contain a homopolymer or may be non-homopolymeric, and may contain from 4 to 6 nucleotides in length, for example. In an exemplary embodiment, calibration sequence information from neighboring wells may be used to determine which neighboring wells contain templates capable of being extended (which may, in turn, allows identification of neighboring wells that may generate ( ) mer signals, 1-mer signals, etc., in subsequent reaction cycles), and may be used to remove or subtract undesired noise components from output signals of interest.

In an exemplary embodiment, an average ( ) mer signal may be modeled (which may be referred to herein as a "virtual 0-mer" signal) by taking into account (i) neighboring empty well output signals in a given cycle, and (ii) one or more effects of the presence of a particle and/or template on the shape of the reagent change noise curve (such as, e.g., the flattening and shifting in the positive time direction of an output signal of a particle-containing well relative to an output signal of an empty well, as reflected in FIG. 2D). Such effects may be modeled to convert empty well output signals to virtual 0-mer output signals, which may in turn be used to subtract reagent change noise.

Figures 6E, 6F:
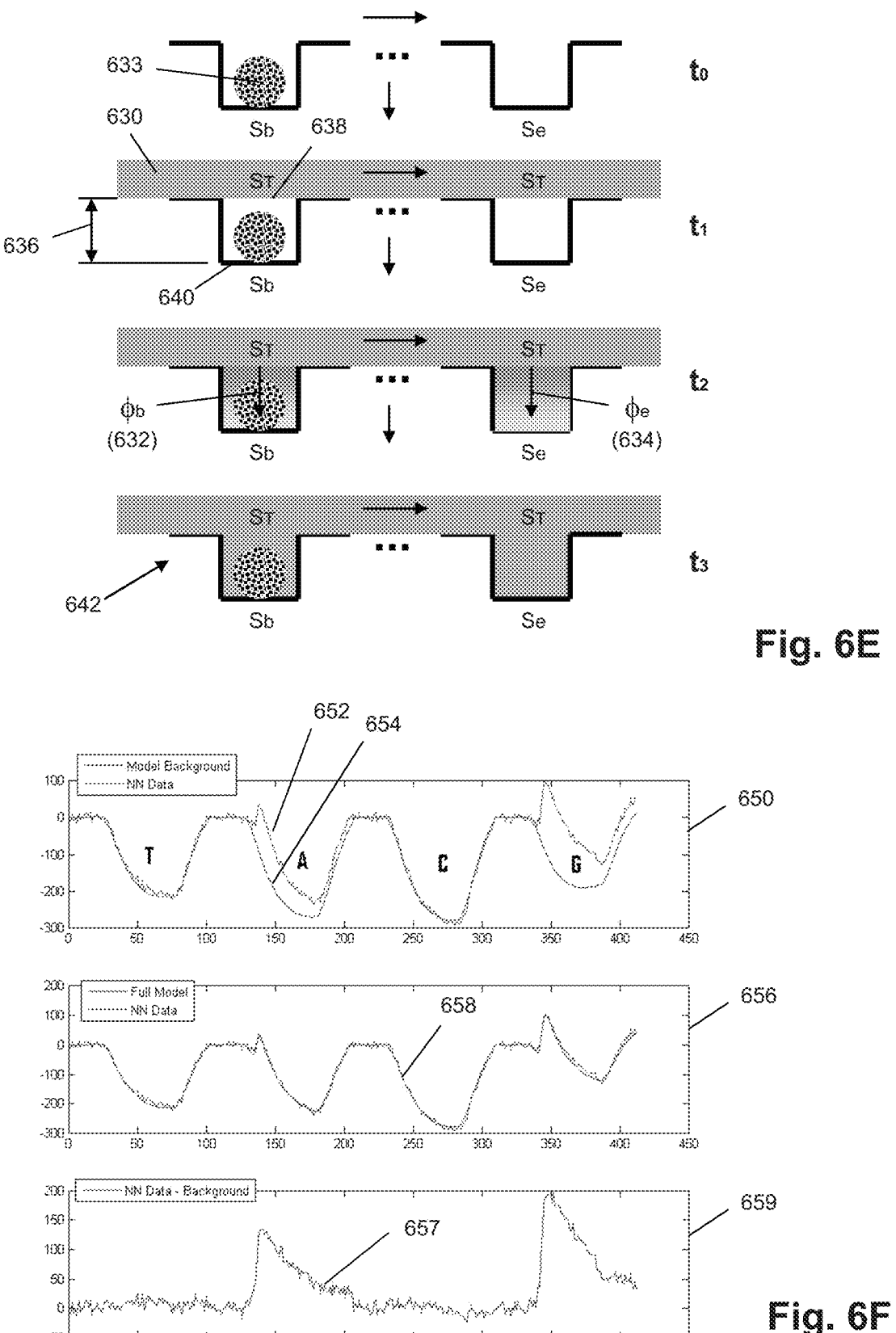
FIG. 6E illustrates a model for using an average neighbor signal to remove reagent change noise from a signal.
FIG. 6F illustrates data fit by a model such as presented in FIG. 6E and use of such model to subtract reagent change noise from an incorporation signal.

FIG. 6E illustrates a model for using an average neighbor signal to remove reagent change noise from a signal according to an exemplary embodiment. Shown are neighboring wells at four different times during a reagent change: to (before a next reagent is added), $t_1$ (immediately after the next reagent is added), $t_2$ (during equilibration of the next reagent with the well contents), and $t_3$ (after equilibrium has been achieved). The change in sensor signal is described as a two compartment model, where one compartment is the next reagent (e.g., the next flow of dNTPs) in region 638 adjacent to the opening of a well and the other compartment is the surface 640 at the bottom of a well adjacent to the sensor. Immediately after new reagent 630 enters, a concentration difference 636 is created between the two compartments, so that a flux of hydrogen ions is established both in wells with particles $\varphi_b$ 632 and in empty wells De 634. For microwells having particles 633 where extension reactions occur, hydrogen ions are also created, which adds to the flux. Eventually equilibrium 642 is reached and the flux of hydrogen ions goes to zero. A variety of alternative models of differing complexity may be used to describe the physical and chemical phenomena of the electrochemical reactions taking place in the wells.

In an exemplary embodiment, the generation of hydrogen ions by extension reactions and the fluxes through wells with and without particles/beads may be described by equations including the following reaction-diffusion equations:

$$\frac{S_T - S_b}{\alpha_b} = \varphi_b = \frac{\delta S_b}{\delta t} \beta_b; \frac{S_T - S_e}{\alpha_e} = \varphi_e = \frac{\delta S_e}{\delta t} \beta_e$$

In these equations, ST refers to the signal measured at the top of the wells, which corresponds to the flowing solution: $S_b$ refers to the signal measured from the bottom of the loaded well: $S_e$ refers to the signal measured from the bottom of the empty well: $\alpha_b$ and $\alpha_c$ are diffusion constants of the hydrogen ions in the solution; and $\beta_b$ and $\beta_c$ are constants that reflect the interaction (e.g., buffering) of the hydrogen ions with the well and/or particle or analyte in the well. Manipulation of these terms and integration yields $S_b$ as a function of $S_e$ and an integral of the difference between $S_e$ and $S_b$, plus a source term, $I_{ext}$, for the hydrogen ions generated in an extension reaction, which can be expressed using the following equation:

$$S_b = S_e R + \frac{\int S_e - S_b}{\tau_b} + I_{ext}$$

In this equation, $R = \tau_e / \tau_b$, Where $\tau_e = \alpha_e \beta_c$ and to $= \alpha_b \beta_b$. Curves for $S_b$ can be generated numerically for fitting data to remove reagent change noise.

FIG. 6F illustrates data fit by a model such as presented in FIG. 6E and use of such model to subtract reagent change noise from an incorporation signal according to an exemplary embodiment. Panel 650 shows an output signal 652 ("NN Data") from a sensor of a well in which extension reactions occur when exposed to flows of dATP and dGTP. Curve 654 ("Model Background") shows a reagent change noise background component (which component may be represented in the model by the first two terms on the right of the expression for $S_b$) from the above model. Panel 656 includes curve 658, which shows both the reagent change noise and the generation of hydrogen ions (which may be represented in the model by the entire expression for $S_b$), and that such complete model nearly overlaps with the "NN Data" curve. Panel 659 shows output signal 657, after removal of the reagent change noise background component, which more clearly shows the signal due to nucleotide incorporations.

Figure 7:
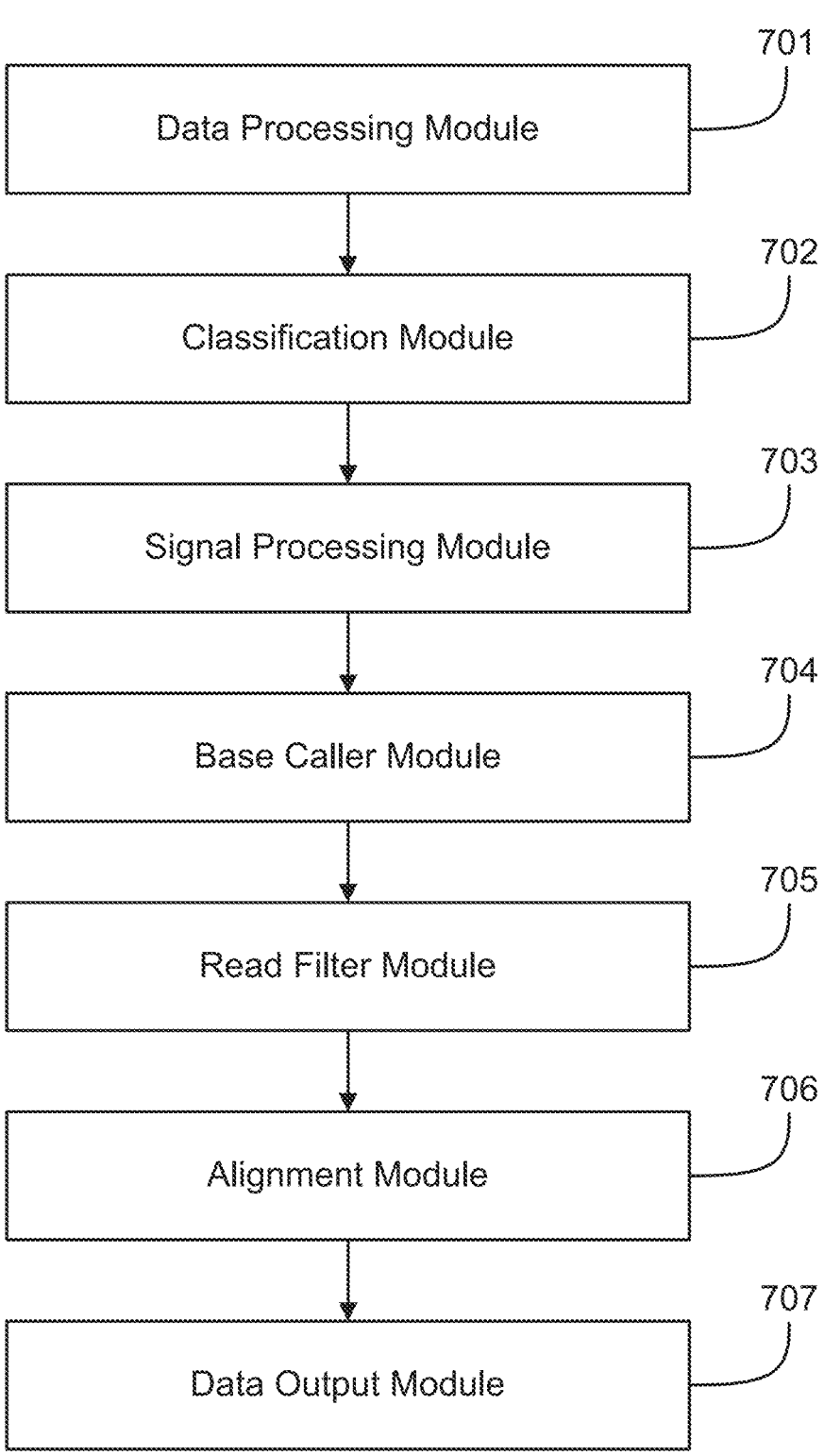
FIG. 7 illustrates a system for nucleic acid sequencing.

FIG. 7 illustrates a system for nucleic acid sequencing according to an exemplary embodiment. The system includes a data processing module 701, a classification module 702, a signal processing module 703, a base caller module 704, a read filter module 705, an alignment module 706, and a data output module 707. The system may be implemented in one or more computers and/or servers and may be accessible at least in part through a web-accessible data portal. In an exemplary embodiment, there is provided a method performing steps including the general steps associated with modules 701-707 (e.g., processing data, classifying defined spaces or reaction confinement regions, processing signals, calling bases, filtering reads, aligning reads, and outputting results).

Data Processing Module

In an exemplary embodiment, a data processing module or data processor may be configured to receive data (e.g., raw data, which may be a series of signals), which may be reflective or indicative of one or more by-product(s) of a chemical reaction. The signals may be derived from nucleotide incorporation events (e.g., incorporation of a dNTP associated with a sample nucleic acid template) by measuring hydrogen ions generated as by-products of polymerase-catalyzed nucleic acid extension reactions. The hydrogen ion concentration (or pH) for a defined space or reaction confinement region may be measured repeatedly and at intervals timed to coincide with the nucleotide flows of different types of dNTPs. The signals may be actual raw pH values, or they may be a conversion of the raw pH value (or related physical measurement) in each defined space into a voltage, for example, which may then be converted into a digital representation.

The data processing module may be configured to generate one or more acquisition file(s) for the raw data, which may contain raw signals from defined spaces of a chip, for example, for one or more nucleotide flow(s). For a chip containing about 1.5 million wells, for example, each nucleotide flow can result in about 1.5 million separate nucleotide incorporation events, and a series of such acquisition files can represent about 1.5 million possible reads. A read can represent consecutive base calls associated with a sequence of a nucleic acid. A read can reflect bases or base complements associated with a sample nucleic acid template, which can be associated with a defined volume, such as a well, or with a defined area, such as a portion of a surface of a substantially flat substrate, for example. A read can include a full sequence of the sample nucleic acid template or a portion thereof. A read can include about eight nucleotides (base calls) and can contain 16 or more base calls, 25 or more base calls, 50 or more base calls, 100 or more base calls, or 120 or more base calls, for example. The length of a read can be expressed as a number of base pairs (bps).

In an exemplary embodiment, the data processing module may be configured to perform multiple functions, including receiving or loading raw data and/or signals (which may be temporarily or permanently stored in a memory and may be compressed and decompressed as desired), decompiling raw data, and offset correcting raw data. For example, the raw data and/or signals may be streamed off of an analytical instrument directly to the data processing module. Alternatively, or in combination with direct steaming, the data processing module may access or receive the raw data and/or signals after storage or collection on a computer-readable medium, such as a portable disk or hard drive, for example. The data processing module may receive directly raw acquisition files in DAT file format (e.g., acq_*dat files), for example, streaming from an analytical instrument.

In an exemplary embodiment, the data processing module may be configured to compress data and/or signals using one or more compression modes, which may include a dynamic/variable frame rate compression mode and a key frame and/or delta compression mode. In the dynamic/variable frame rate compression mode, certain portions of a nucleotide incorporation event or a nucleotide flow may be captured at different frame rates to allow capture of biologically specific events at high resolution while reducing the overall file size by allowing multiple frames in some portions to be averaged. In the key frame and/or delta compression mode, whereas an initial value is actually stored, for subsequent values only their difference relative to the initial value may be stored.

In an exemplary embodiment, the data processing module may be configured to perform raw signal offset and/or background corrections. Each defined space may have its own reference value. To compare two defined spaces, a common reference may be used. The offset and/or background correction can take the average of the first few frames within each acquisition file, and subtract that value from values for each defined space, thus allowing measurements within the defined space to have a common reference value.

In an exemplary embodiment, the data processing module may flag or exclude certain defined spaces that may for whatever reason not be functional or may be covered, obscured, or otherwise fluidically inaccessible or unaddressable. For example, a mask may be loaded, per chip type, to mark those defined spaces as excluded so as to avoid unnecessary and/or computationally inefficient downstream processing of the chip and signals generated therefrom, where the information likely will be uninformative.

Classification Module

In an exemplary embodiment, a classification module or classifier may be configured to classify one or more wells of an array as to whether the well is empty or contains an analyte or substrate associated with an analyte and whether the well generally contains useful information that should be carried forward and included in downstream processing and/or analysis. Because the data can include signals from thousands to millions of individual wells, reducing the amount of data to be carried forward can increase overall performance and efficiency, and conserve file storage space. (Of course, in practice while some data can be screened, all data may be stored so that various screening and manipulating of the data can be started anew, if desired.) The classification module may process wells in smaller groups or regions rather than as one group to exploit parallel computing techniques, such as multi-core and/or multi-process nodes that have parallel computational capabilities. For example, a chip containing an array of about 1.5 million wells can be segmented into 50×50 well regions, resulting in about 625 total regions.

In an exemplary embodiment, the classification module may be configured to classify one or more wells of an array as to whether the well is empty or contains an analyte or substrate associated with an analyte by flowing a known pH buffer at a different pH than a wash buffer onto the wells. If the diffusion rate in the well is slower than an average rate of surrounding neighbors, for example, then the well may be considered to contain a particle. If not, then the well may be identified as empty. Other procedures to establish a baseline pH change over time can include, for example, fitting the signal to exponentials or other models of the expected background signal.

According to an exemplary embodiment, there is provided a method for determining whether a defined space includes an analyte or substrate associated with an analyte, including: (1) changing reagents in a flow chamber from a first reagent that sensors generate in response thereto a first output signal to a second reagent that sensors generate in response thereto a second output signal; and (2) correlating a time delay in the generation of the second output signal in response to the changing of reagents with a presence or absence of an analyte or substrate associated with an analyte. The sensor may be an electrochemical sensor, including a potentiometric sensor, an impedimetric sensor, or an amperometric sensor, for example, or any sensor such that the output signal depends on an interaction between an electrode or other analyte-sensitive surface and a sensor-active reagent whose arrival is delayed by physical or chemical obstructions in a defined space. The sensor-active reagent may be a wash solution at a different pH than the reagent it replaces.

In an exemplary embodiment, the classification module may be further configured to identify and parse sample nucleic acids or fragments based on their type and/or origin. Such identification, which may be useful when using test nucleic acid fragments as a control and/or when pooling and sequencing fragmented samples of nucleic acids from different origin ("multiplexing"), for example, may be based on labeling or tagging of the fragments prior to the sequencing process (e.g., with fluorescent tags). Such identification may be performed using sequencing keys (e.g., a known artificial nucleic acid sequence).

FIG. 8 illustrates a method for classifying a content of a defined space according to an exemplary embodiment. In step 801, a module or other hardware and/or software component considers whether a defined space includes one or more nucleic acids, which may be associated with a solid substrate such as a bead. In step 802, if the answer is no, the defined space may be marked as empty. In step 803, if the answer is yes, a module or other hardware and/or software component considers whether the defined space yields informative data about the sample nucleic acids. In step 804, if the answer is no, the defined space may be marked as non-informative. In step 805, if the answer is yes, a module or other hardware and/or software component considers whether the sample nucleic acid(s) correspond to one of a test fragment (TF) and a library fragment (LF). In step 806, if the answer is no, the defined space may be marked as ambiguous. In step 807, if the answer is yes, the defined space may be marked as TF or LF as the case may be.

In an exemplary embodiment, a sequencing key can be viewed as a unique identifier, such as a bar code, of the type or origin of the sample nucleic acid template or population of nucleic acid fragments to permit appropriate sorting and/or association of nucleic acid sequences randomly dispersed in an array. One, two, or more sequencing keys may be used. A "library sequencing key" or "library fragment key." for example, may be a known artificial nucleic acid sequence identified or associated with a fragment of a nucleic acid sequence from a library. The library sequencing key may be associated with or be part of an adapter sequence or have another association with particles including fragments from the library of a nucleic acid sequence of interest. A "test fragment sequencing key" or "test fragment key." for example, may be a known artificial nucleic acid sequence identified or associated with a known fragment of a nucleic acid used as a control or reference. If the library sequencing key and the test fragment sequencing key are distinct identifiers of each key, then a comparison of a read of unknown origin against each of them should produce a match or a comparison of sufficient confidence. If such identification cannot be made, then the information from that well can be flagged, discarded, or ignored as being an ambiguous well. The sequencing keys may have the same length or different lengths, in which case comparison may be based on the shortest length. Of course, other kinds of sequencing keys are possible, and a test fragment key may or may not always be used.

FIG. 9 illustrates a particle 50 associated with a sample nucleic acid template 52, a primer 56, and a sequencing key

54 according to an exemplary embodiment. The sequencing key (bold nucleotides A G T C), which may be added to the 5' end of the sample nucleic acid template to be at the beginning of a read to permit early identification and classification of the origin of the sample nucleic acid template (as a test fragment or a library fragment, for example). If no identification can be made (e.g., where there is no or low signal strength, ambiguous identification of the sample nucleic acid template, and/or a particle with more than one type of sample nucleic acid template or fragment (e.g., polyclonal)), the fragment may be classified as being ambiguous. A particle could have multiple sequencing keys for classifying different aspects. For example, one such key might be used to determine whether a sample is a library fragment, and another (which could have a different length (e.g., longer)) might be used to serve as an additional "bar code" for the sample.

A comparison of a read of unknown origin against a sequencing key may be done in various ways depending on the format of the signals. The comparison may be done in "base-space" format (e.g., using a series or vector of nucleotide designations such as A, C, G, and T that correspond to the series of nucleotide species that were flowed and incorporated). The comparison may also be done in "flow-space" format (e.g., using a series or vector of zeros and ones representing a non-incorporation event (a zero, "0")") for a given nucleotide flow or a nucleotide incorporation event (a one, "1") for a given nucleotide flow). Thus, in flow-space format, the nucleotide flow order and whether and how many non-events and events occurred for any given nucleotide flow determine the flow-space format series of zeros and ones, which may be referred to as the flow order vector. (Of course, zeros and ones are merely convenient representations of a non-incorporation event and a nucleotide incorporation event, and any other symbol or designation could be used alternatively to represent and/or identify such non-events and events.) Also, a homopolymer region may be represented by a whole number greater than one, rather than the respective number of one's in series (e.g., one might represent a "T" flow resulting in an incorporation followed by an "A" flow resulting in two incorporations by "12" rather than "111" in flow-space).

To illustrate the interplay between base-space vectors, flow-space vectors, and nucleotide flow orders, one may consider, for example, an underlying template sequence beginning with "TA" subjected to multiple cycles of a nucleotide flow order of "TACG."

The first flow, "T," would result in a non-incorporation because it is not complementary to the template's first base, "T." In the base-space vector, no nucleotide designation would be inserted: in the flow-space vector, a "0" would be inserted, leading to "0." The second flow, "A," would result in an incorporation because it is complementary to the template's first base, "T." In the base-space vector, an "A" would be inserted, leading to "A": in the flow-space vector, a "1" would be inserted, leading to "01." The third flow, "C," would result in a non-incorporation because it is not complementary to the template's second base, "A." In the base-space vector, no nucleotide designation would be inserted: in the flow-space vector, a "0" would be inserted, leading to "010." The fourth flow, "G," would result in a non-incorporation because it is not complementary to the template's second base, "A." In the base-space vector, no nucleotide designation would be inserted: in the flow-space vector, a "(" would be inserted, leading to "0100." The fifth flow, "T," would result in an incorporation because it is complementary to the template's second base, "A." In the base-space vector, a "T" would be inserted, leading to "ΔT": in the flow-space vector, a "1" would be inserted, leading to "01001." (Note: if the analysis were to contemplate a potentially longer template, an "X" could be inserted here instead because additional "A's" could potentially be present in the template in the case of a longer homopolymer, which would allow for more than one incorporations during the fifth flow, leading to "0100X.") The base-space vector thus shows only the sequence of incorporated nucleotides, whereas the flow-space vector shows more expressly the incorporation status corresponding to each flow. Whereas a base-space representation may be fixed and remain common for various flow orders, the flow-based representation depends on the particular flow order. Knowing the nucleotide flow order, one can infer either vector from the other. Of course, the base-space vector could be represented using complementary bases rather than the incorporated bases (thus, one could just as well define the base-space representation of a sequencing key as being the incorporated nucleotides or as being the complementary nucleotides of the template against which the flowed nucleotides would be incorporated).

Table 1 shows exemplary library and test fragment sequencing keys in both base-space format and in flow-space format for a nucleotide flow order of TACG.

TABLE 1

| | Base-space format | Flow-space format |
|---|---|---|
| Library Fragment Sequencing Key | TCAG | 1010010X |
| Test Fragment Sequencing Key | ATCG | 0100101X |

According to an exemplary embodiment, there is provided a method for classifying a content of a defined space, including: (1) providing a flow-space format vector of a sample nucleic acid based on a series of nucleotide flows to a defined space and a series of signals from the defined space, the sample nucleic acid being associated with the defined space and each of the series of signals being indicative of the hydrogen ion concentration in the defined space: (2) comparing the flow-space format vector of the sample nucleic acid to each of a flow-space format vector of a first sequencing key and a flow-space format vector of a second sequencing key, the flow-space format vectors of the first and second sequencing keys being derived from the series of nucleotide flows; and (3) classifying, based on the comparison, the sample nucleic acid as a fragment associated with the first sequencing key, a fragment associated with the second sequencing key, or an ambiguous fragment. In such a method, providing a flow-space format vector may include determining for a first nucleotide flow of the series of nucleotide flows of a first nucleotide whether a 0-mer, a 1-mer, a 2-mer, a 3-mer, a 4-mer, or a higher order number of nucleotide incorporation events occurred based on the signal from the defined space associated with the first nucleotide flow, wherein a ( ) mer nucleotide incorporation event is a non-incorporation event. Providing a flow-space format vector of a sample nucleic acid may include recording sequentially, as the flow-space format vector of the sample nucleic acid: 0, 1, 11, 111, or 1111, or the higher order number of ones (1's) for a corresponding ( ) mer, 1-mer, 2-mer, 3-mer, 4-mer, or the higher order number nucleotide incorporation events, respectively. Providing a flow-space format vector of a sample nucleic acid may further include repeating the determining and recording for a second nucleotide flow of a second nucleotide, for a third nucleotide flow of a third nucleotide, and for a fourth nucleotide flow of a fourth nucleotide. Providing a flow-space format vector of a sample nucleic acid may further include repeating the determining and recording for a fifth nucleotide flow of the first nucleotide, for a sixth nucleotide flow of the second nucleotide, for a seventh nucleotide flow of the third nucleotide, and for an eighth nucleotide flow of the fourth nucleotide, and so on until at least one nucleotide incorporation event occurs for each of the four nucleotides. The first sequencing key may include a library sequencing key and the second sequencing key may include a test fragment sequencing key. According to an exemplary embodiment, there is provided a non-transitory machine-readable storage medium comprising instructions which, when executed by a processor, cause the processor to perform such a method for classifying a content of a defined space or related methods and variants thereof.

In an exemplary embodiment, sequencing keys may be designed by increasing a likelihood that they will be sufficiently distinguishable so that the identification can be made with sufficient confidence. Such design may be done by evaluating an orthogonality (or distinctiveness) between keys. Sequencing keys may be orthogonal with respect to zero, one, two, three, or four nucleotides, with a higher number signifying a higher separation between the keys, which may result in increased confidence in the accuracy of the identification of the origin of a read, and which can allow identification and classification using fewer bases/flows (and thus less data). As shown in detailed examples below, which are explanatory only and not to be construed as limiting or restrictive in any way, two sequencing keys can be considered to be orthogonal with respect to a given nucleotide if two conditions or rules are satisfied for the given nucleotide in flow-space. The rules are as follows:

Rule 1: Both a non-incorporation event ("0-mer") and a nucleotide incorporation event ("1-mer") must be present in each sequencing key for the given nucleotide.

Rule 2: Each nucleotide incorporation event ("1-mer") or non-incorporation event ("0-mer") in one sequencing key for any given flow of the given nucleotide must correspond to an opposite non-incorporation event ("0-mer") or nucleotide incorporation event ("1-mer") in the other sequencing key.

As a first example, one may consider the orthogonality of the sequencing keys in Table 1 for nucleotide flow order TACG. The flow-space format vectors are reproduced below (without the "X," which is an unknown). Each row represents a sequencing key and each column represents a nucleotide flow. As explained below, these keys may be considered orthogonal with respect to T, A, and C, but not G.

| 1 | 0 | 1 | 0 | 0 | 1 | 0 |
|---|---|---|---|---|---|---|
| 0 | 1 | 0 | 0 | 1 | 0 | 1 |

Regarding the "T" nucleotide, which corresponds to the first and fifth flows (see bolded columns below), each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "T."

| 1 | 0 | 1 | 0 | 0 | 1 | 0 |
|---|---|---|---|---|---|---|
| 0 | 1 | 0 | 0 | 1 | 0 | 1 |

Regarding the "A" nucleotide, which corresponds to the second and sixth flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "A."

| 1 | 0 | 1 | 0 | 0 | 1 | 0 |
|---|---|---|---|---|---|---|
| 0 | 1 | 0 | 0 | 1 | 0 | 1 |

Regarding the "C" nucleotide, which corresponds to the third and seventh flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "C."

| 1 | 0 | 1 | 0 | 0 | 1 | 0 |
|---|---|---|---|---|---|---|
| 0 | 1 | 0 | 0 | 1 | 0 | 1 |

Finally, regarding the "G" nucleotide, which corresponds to the fourth flow, each key does not include both a nucleotide incorporation event ("1") and a non-incorporation event ("0"), thereby failing to meet rule 1. Thus, these keys may not be considered orthogonal with respect to "G."

| 1 | 0 | 1 | 0 | 0 | 1 | 0 |
|---|---|---|---|---|---|---|
| 0 | 1 | 0 | 0 | 1 | 0 | 1 |

As a second example, one may consider the orthogonality of a library sequencing key CTAGT with the same test fragment sequencing key for nucleotide flow order TACG.

| 0 | 0 | 1 | 0 | 1 | 1 | 0 | 1 | X |
|---|---|---|---|---|---|---|---|---|
| 0 | 1 | 0 | 0 | 1 | 0 | 1 | X |  |

Because the two vectors here have different lengths, comparison may be based on the first seven known values. These keys may be considered orthogonal with respect to A and C, but not G and T.

| 0 | 0 | 1 | 0 | 1 | 1 | 0 |
|---|---|---|---|---|---|---|
| 0 | 1 | 0 | 0 | 1 | 0 | 1 |

Regarding the "T" nucleotide, which corresponds to the first and fifth flows, each key includes both a nucleotide incorporation event ("1") and a non-incorporation event ("0"), thereby meeting rule 1, however, each nucleotide incorporation event or non-incorporation event (i.e., "1" or "0") in one key corresponds to an identical nucleotide incorporation event or non-incorporation event (i.e., "1" or "0") in the other key, thereby failing to meet rule 2. Thus, these keys may not be considered orthogonal with respect to "T."

| 0 | 0 | 1 | 0 | 1 | 1 | 0 |
|---|---|---|---|---|---|---|
| 0 | 1 | 0 | 0 | 1 | 0 | 1 |

Regarding the "A" nucleotide, which corresponds to the second and sixth flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "A."

| 0 | 0 | 1 | 0 | 1 | 1 | 0 |
|---|---|---|---|---|---|---|
| 0 | 1 | 0 | 0 | 1 | 0 | 1 |

Regarding the "C" nucleotide, which corresponds to the third and seventh flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "C."

| 0 | 0 | 1 | 0 | 1 | 1 | 0 |
|---|---|---|---|---|---|---|
| 0 | 1 | 0 | 0 | 1 | 0 | 1 |

Finally, regarding the "G" nucleotide, which corresponds to the fourth flow, each key does not include both a nucleotide incorporation event ("1") and a non-incorporation event ("0"), thereby failing to meet rule 1. Thus, these keys may not be considered orthogonal with respect to "G."

| 0 | 0 | 1 | 0 | 1 | 1 | 0 |
|---|---|---|---|---|---|---|
| 0 | 1 | 0 | 0 | 1 | 0 | 1 |

According to an exemplary embodiment, there is provided a method for selecting sequencing keys, including: (1) providing at least a first sequencing key and a second sequencing key, the first and second sequencing keys having flow-space format representations based on a series of predetermined nucleotide flows to a defined space: (2) determining whether the flow-space format representation of the first sequencing key includes both a non-incorporation event and a nucleotide incorporation event for at least a first given type of flowed nucleotide; and (3) determining whether the flow-space format representation of the second sequencing key includes both a non-incorporation event and a nucleotide incorporation event for at least the first given type of flowed nucleotide. In such a method, the defined space may be configured to generate a series of signals indicative of an hydrogen ion concentration in the defined space. The method may further include determining for at least the first given type of flowed nucleotide whether each nucleotide incorporation event or non-incorporation event in the flow-space format representation of the first sequencing key for any given flow of the at least first given type of flowed nucleotide corresponds to an opposite non-incorporation event or nucleotide incorporation event in the flow-space format representations of the second sequencing key. The method may further include concluding, if each of the determining steps results in a positive response, that the first sequencing key and the second sequencing key are orthogonal with respect to the at least first given type of flowed nucleotide. The method may further include repeating one or more of the determining steps for a second given type of flowed nucleotide, a third given type of flowed nucleotide, and a fourth given type of flowed nucleotide to determine whether the first sequencing key and the second sequencing key are orthogonal with respect to one or more of the second given type of flowed nucleotide, the third given type of flowed nucleotide, and the fourth given type of flowed nucleotide. The first sequencing key may include a library sequencing key and the second sequencing key may include a test fragment sequencing key. The method may include determining, for the first occurrence of a first nucleotide in the first sequencing key, whether a single incorporation event in the first sequencing key occurs during a non-incorporation event for the second sequencing key for the same nucleotide flow; and determining, for the first occurrence of the first nucleotide in the second sequencing key, whether a single incorporation event in the second sequencing key occurs during a non-incorporation event for the first sequencing key for the same nucleotide flow. According to an exemplary embodiment, there is provided a non-transitory machine-readable storage medium comprising instructions which, when executed by a processor, cause the processor to perform such a method for selecting sequencing keys or related methods and variants thereof.

According to an exemplary embodiment, there is provided a system for nucleic acid sequencing, including: (1) a vector comparison module configured to compare a flow-space format vector of a sample nucleic acid to a flow-space format vector of a first sequencing key and a flow-space format vector of a second sequencing key, wherein the first and second sequencing keys are derived from a series of nucleotide flows; and (2) a nucleic acid origin identification module configured to identify, based on the comparison, the sample nucleic acid as being associated with the first sequencing key, the second sequencing key, or as an ambiguous fragment.

Figure 10:
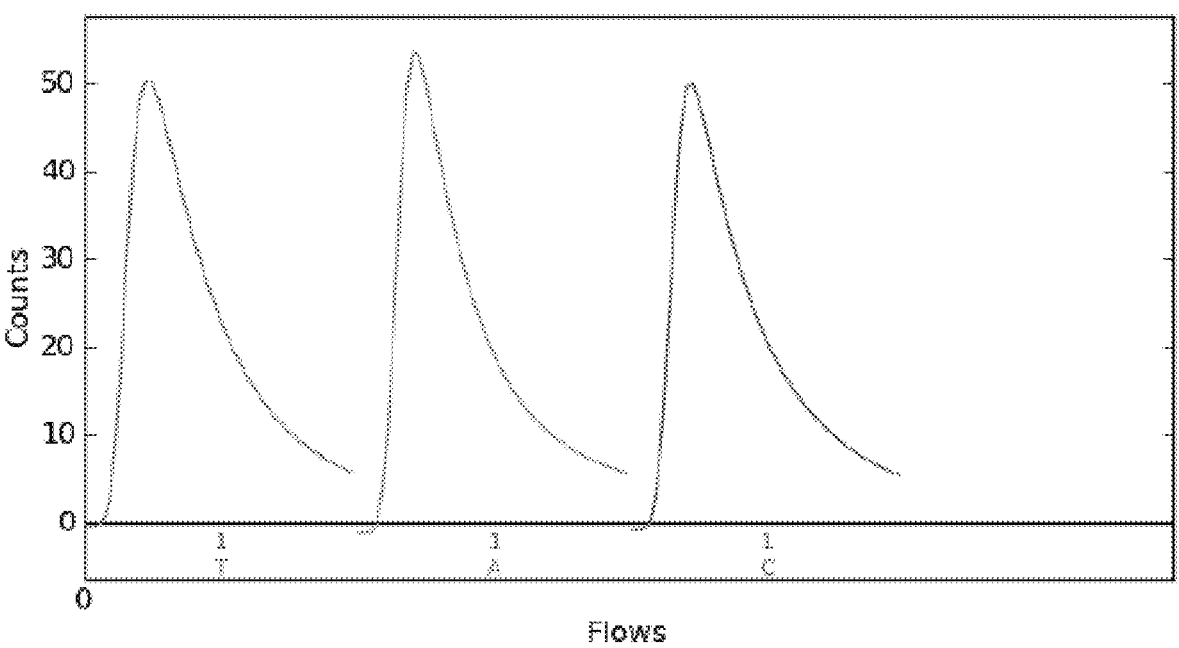
FIG. 10 illustrates consensus incorporation signals for three initial bases of a library sequencing key.

FIG. 10 illustrates consensus incorporation signals averaged from a large number of reads for three initial bases of a library sequencing key according to an exemplary embodiment. The consensus incorporation signals may be used by a user to visually confirm the quality of a run, for example.

Figure 11A:
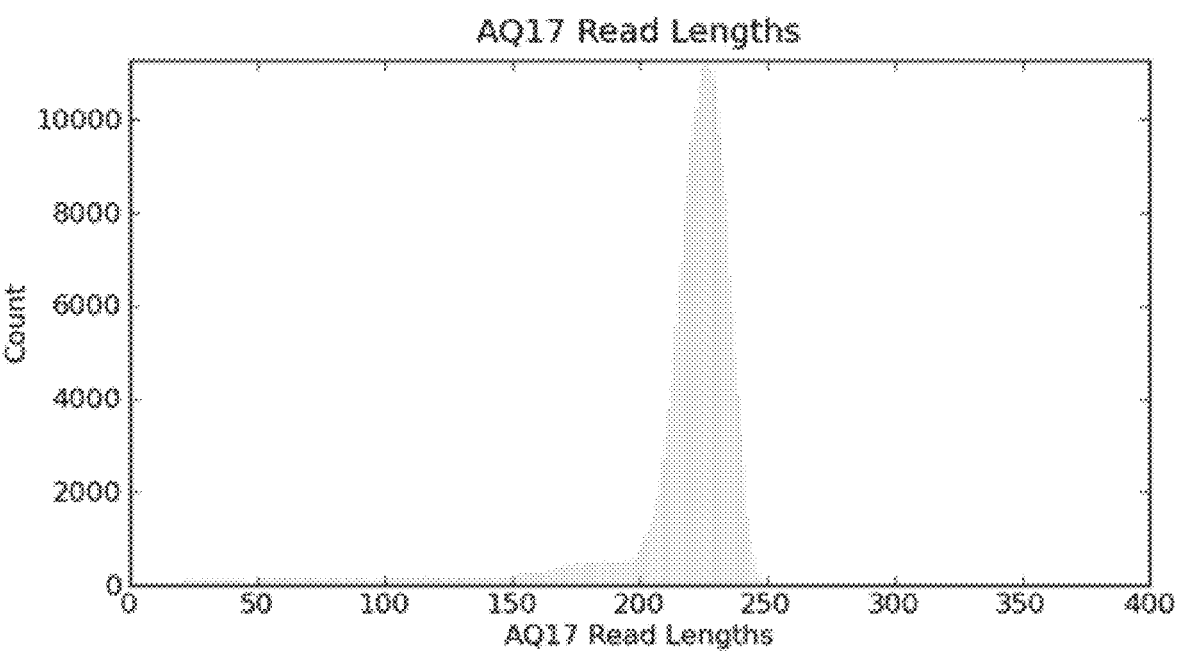
FIG. 11A illustrates a histogram of library read lengths.

FIG. 11A illustrates a histogram of library read lengths according to an exemplary embodiment. The histogram depicts the AQ17 read length for each read aligned to a reference genome.

Figure 11B:
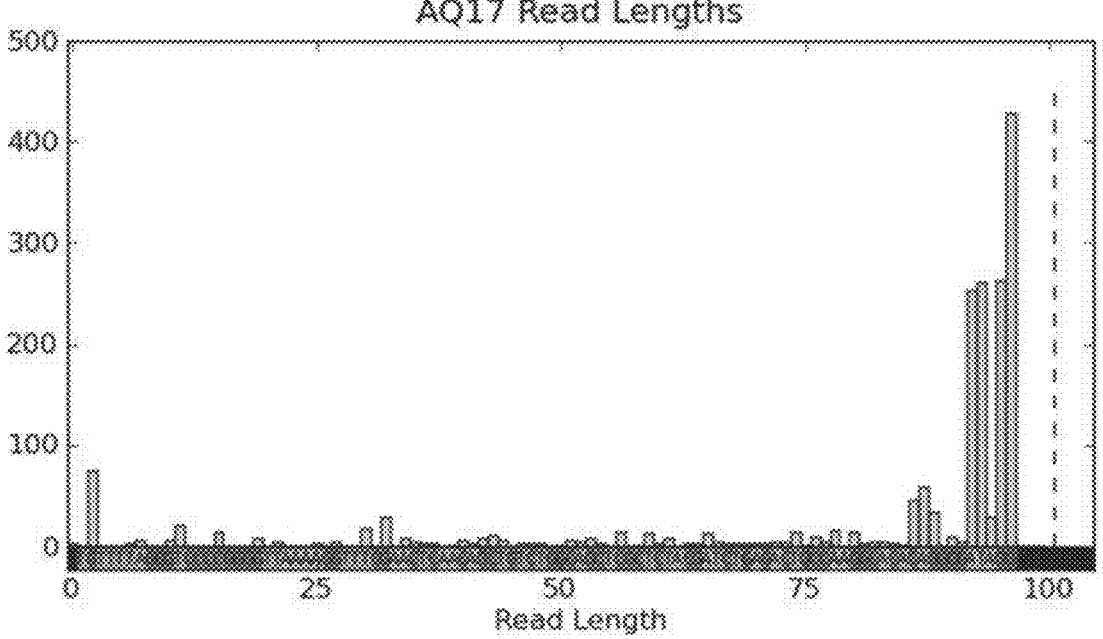
FIG. 11B illustrates a histogram of test fragment read lengths.

FIG. 11B illustrates a histogram of test fragment read lengths according to an exemplary embodiment. The histogram depicts the AQ17 read length of each test fragment as mapped to its reference (actual) sequence. The distribution of test fragment lengths is highly concentrated because test fragments are positive controls of known composition and defined length.

In an exemplary embodiment, the classification module may receive directly or indirectly a data file, e.g., from the data processing module, and may store, transmit, or output classification information in a MASK file format (e.g., bfmask.bin), which can contain one or more bit flags for each well, indicating the contents of each defined space.

Signal Processing Module

In an exemplary embodiment, a signal processing module or signal processor may be configured to analyze signal information from a defined space or reaction confinement region and an associated sample nucleic acid template. The signal processing module may output a processed signal, which may be considered a raw incorporation signal. The signal processing module may use information and data resulting from the classification module and associated methods, but may also use raw data or raw signals.

In an exemplary embodiment, the signal processing module may be configured to remove noise from raw signal and improve a quality of the signal, which may include an accuracy and a signal-to-noise ratio of the raw signals, for example. Noise, which may be due to various causes including thermal sensitivity of the sensors, electrical potential disturbances in the fluid (such as resistive or thermal noise in the fluids, reference voltage changes due to different fluids contacting the reference electrode), pH changes due to bulk changes in fluids that are passed over the sensor array (referred to herein as "reagent change noise"), stochastic behavior of polymerase function (e.g., incomplete extensions) or failure to completely wash away all dNTPs in a given step (e.g., inappropriate incorporation), for example, may be removed in various ways.

In an exemplary embodiment, the signal processing module may be configured to remove from the data and signals it received some background signal or noise to generate an improved incorporation signal. To minimize computation time, the signal processing module may only process data and signals for defined spaces containing particles and/or having produced a sufficiently strong signal to indicate a nucleotide incorporation event. The background or noise portion of the signal can be present during each flow and can vary over time, across an array of wells, and during an acquisition.

In an exemplary embodiment, the signal processing module may be configured to create an incorporation fitting model, which may have two parts. The first part may include determining the background signal that would have been measured in a given defined space had no nucleotide incorporation event occurred. The second part may include subtracting or otherwise removing (or fitting) the background signal from the raw signal and then examining and analyzing (or fitting) the signal that remains. The result of the incorporation fitting model may be an estimate of incorporation during each nucleotide flow for each well.

In an exemplary embodiment, the signal processing module may be configured to perform or implement one or more of the teachings disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No. 61/428,097, filed Dec. 29, 2010, which are all incorporated by reference herein in their entirety.

In an exemplary embodiment, the signal processing module may receive a MASK file from the classification module, for example. The signal processing module may store, transmit, and/or output raw incorporation signals and related information and data in raw WELLS file format, for example. The signal processing module may output a raw incorporation signal per defined space and per flow, for example.

Base Caller Module

In an exemplary embodiment, a base caller module or base caller may be configured to transform a raw incorporation signal into a base call and compile consecutive base calls associated with a sample nucleic acid template into a read. A base call refers to a particular nucleotide identification (e.g., dATP ("A"), dCTP ("C"), dGTP ("G"), or dTTP ("T")). The base caller module may perform one or more signal normalizations, signal phase and signal droop (e.g. enzyme efficiency loss) estimations, and signal corrections, and it may identify or estimate base calls for each flow for each defined space. The base caller module may share, transmit or output non-incorporation events as well as incorporation events.

In an exemplary embodiment, the base caller module may be configured to normalize a read, which may include initially using raw data and/or signals from the signal processing module. For example, using one or more known expected 1-mer events, which may be identified using sequencing keys, a 1-mer average signal may initially be established and used for normalization. Then, as the base caller module processes each defined space, additional base calls can be accurately determined and additional measurements then can be used to re-normalize the raw signals. Such re-normalization process may improve confidence (e.g., a higher signal-to-noise ratio) of the signal from each defined space.

In an exemplary embodiment, the base caller module may be configured to observe and account for signal droop that in some instances may be attributed to DNA polymerase loss that can occur during a sequencing run. Such DNA polymerase loss may be experienced during nucleotide incorporation events, with values typically in the range of about 0).1% to about 0.2% over the course of a run. By averaging groups of reads in a region together and/or averaging their signals after normalization, an exponential can be fit to the resulting curve, from which the rate of signal loss over time can be extracted to determine an estimate of the DNA polymerase loss during nucleotide incorporation events.

In an exemplary embodiment, the base caller module may be configured to use the signal droop in a signal phase model as a constant for a read. Signal estimates can vary across an array of defined spaces, but signal droop estimates often can be assumed to be fixed for each processed region. The signal phase model can fit parameters, including carry-forward and incomplete extension parameters, which may lead to an estimate of the carry-forward and incomplete extension for each defined space. Polymerase-based carry-forward and incomplete extension phenomena, see, e.g., Margulies et al., NATURE, 437:376-380 (2005), may also be referred to as plus frame shifts and minus frame shifts, see, e.g., Ronaghi et al., GENOME RESEARCH, 11:3-11 (2001), plus-shift effects and minus-shift effects, see Svantesson et al., BIO-PHYSICAL CHEMISTRY, 110:129-145 (2004), and extension failures, see U.S. Pat. No. 7,875,440. The resulting values may be averaged over small regions to reduce errors and noise in the fit, which averaging may be done in various ways, including for any given defined space in a manner that uses neighboring defined spaces in small regions while excluding the defined space to which the resulting values may be applied in downstream analysis, as discussed in Davey et al., U.S. Prov. Appl. No. 61/684,221, filed Aug. 17, 2012, which is incorporated by reference herein in its entirety. The output carry-forward and incomplete extension values can be used as inputs to other parts of the base caller module, for example, a solver function.

In an exemplary embodiment, the base caller module may include a solver function that can apply phase and droop estimates to the normalized signals and make predictions of the likely signal measurements for each nucleotide flow for probable nucleotide incorporation events. The solver function can compare the actual measured value to a list of predicted values and the best fit prediction at each nucleotide flow can be used as the base call for that flow. For example, a ( ) mer, 1-mer, 2-mer, 3-mer, 4-mer, and higher order nucleotide incorporations can be predicted at each nucleotide flow. The solver function can continue such processing over the entire read. At the end of one pass, a good estimate of all base calls for that read can be made. The solver function then can iterate over the read again, applying the same phase and droop estimates at each nucleotide flow, to refine the base calls.

In an exemplary embodiment, the base caller module may be configured to perform or implement one or more of the teachings disclosed in Davey et al., U.S. patent application Ser. No. 13/283,320, filed Oct. 27, 2011, based on U.S. Prov. Pat. Appl. No. 61/407,377, filed on Oct. 27, 2010, and in Davey et al., U.S. Prov. Appl. No. 61/684,221, filed Aug. 17, 2012, which are all incorporated by reference herein in their entirety.

In an exemplary embodiment, the solver may be configured as a software tool or application with functionality to efficiently solve or determine, from a set of possible or candidate sequences of bases, which sequence is in some sense most consistent with some observed data. Possible or candidate sequences may be evaluated by predicting data that would be expected for such sequences under one or more predictive models and determining how "close" under some distance criterion the predicted data are from the observed data.

To illustrate this, let Y represent observed or measured data (e.g., a vector of values such as an observed or measured ionogram or flowgram, for example, or other sequencing values), let X represent predicted data (e.g., a vector of values such as a predicted ionogram or flowgram), let A represent a set of possible or candidate nucleic acid or base sequences (e.g., the set comprising the possible sequences of A, C, G, and T: the set comprising the possible sequences of A, C, G, and T that have at most a certain length: or any other subset of candidate sequences), and let P represent a set of parameters used by the one or more predictive models (e.g., parameters for the incomplete extension, carry-forward, and droop rates). Then, in an embodiment, the solver may be thought of as a function f that determines for some defined space or reaction confinement regions comprising one or more sample nucleic acids a "best" candidate sequence A* from set A such that $$A^* = f(Y, X(A,P)) = \arg\min_{A,P} D(Y - X(A,P)),$$

where $$\arg\min_{x,y} f(x,y)$$

generally denotes the value (or values) of x and y that would generally minimize the function $f(x, y)$ and where $D(y-x)$ denotes some function of the "distance" between y and x (e.g., a sum of squared distances or any other measure of a distance between vectors, for example).

Such a solver may in principle consider the possible combinations of sequences in set A and values for the parameters in set P to identify an optimal combination of a sequence and parameter values. Of course, such an exhaustive search may be computationally expensive and potentially very time consuming. In practice the search may advantageously be limited to a subset of sequences and subset of candidate values for the parameters. In an embodiment, the search may be facilitated by performing parameter estimation separately from the optimization, dividing the process into two phases. For example, in a first step, the parameters may be estimated. And in a second step, the parameter estimates may be treated as fixed and supplied as inputs to the solver problem, which could then be reformulated as $$A^* = f(Y, X, A, P) = \arg\min_{A} D(Y - X(A|P)),$$

where X(A|P) denotes X as a function of A given some fixed parameters P.

In an exemplary embodiment, if P included three parameters (e.g., incomplete extension, carry-forward, and droop rates represented as IER, CFR, and DR, respectively), then an optimal sequence A* may be found as follows: First, estimates of IER, CFR, and DR may be obtained using any suitable method, including as disclosed in Davey et al., U.S. patent application Ser. No. 13/283,320, filed Oct. 27, 2011, based on U.S. Prov. Pat. Appl. No. 61/407,377, filed on Oct. 27, 2010, and in Davey et al., U.S. Prov. Appl. No. 61/684, 221, filed Aug. 17, 2012, which are all incorporated by reference herein in their entirety. Second, A* may be found by solving $$A^* = \arg\min_{A} D(Y - X(A|IER,CFR,DR)),$$

where X(A|P) denotes X as a function of A given some fixed parameters P (e.g., IER, CFR, and DR in this example). Any suitable optimization method may be used to solve this problem. Also, such an approach does not require any particular type or choice of parameters and/or models using such parameters, although better parameters/models may improve accuracy and performance.

In various embodiments, the sequence identification approaches of the present teachings may go beyond "base-by-base" base calling, and extend to "whole-sequence" or "whole-read" calling (or at least "whole-fragment" calling). That is, the output of a solver as described herein may be a particular sequence that was collectively considered/called, rather than merely a sequence of individual bases that were considered/called one by one and then joined together to form a sequence. As a result, although the predictive modeling may include some incremental base-by-base aspects, for example, it may sometimes be the case that a particular base (e.g., the second) may be deemed to be a T (in the case of a hypothetical output of the solver yielding sequence "ATTGC . . . ") even though one might have made a different base call had one not considered how consistent the predicted data for the entire candidate sequence may be with measured or observed data.

Figure 12:
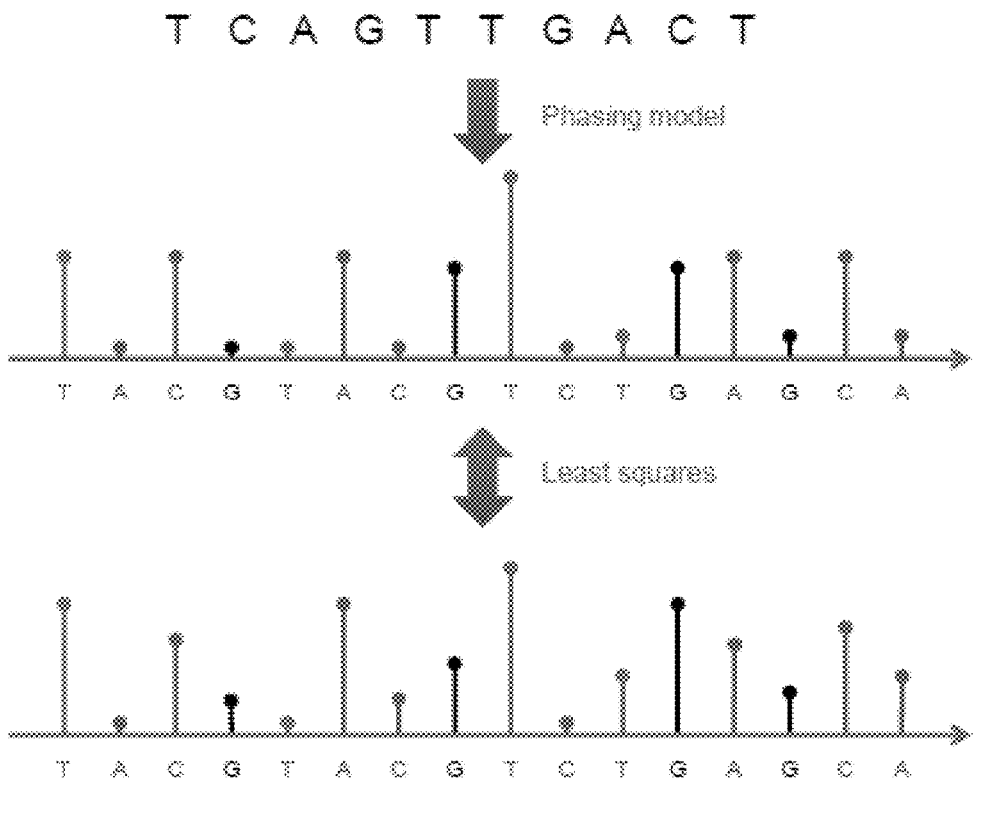
FIG. 12 illustrates conceptually an approach for making base calls in presence of effects capable of causing sequencing errors (such as, e.g., phasing effects).

FIG. 12 illustrates conceptually an approach for making base calls in presence of effects capable of causing sequencing errors (such as, e.g., phasing effects), according to an exemplary embodiment. It illustrates schematically the concept of finding as solution a sequence of bases (e.g., T. C, A, G. T. T. G, A, C, and T) ((SEQ ID NO: 2)) for which a predicted set of values (shown in the top graph as, e.g., a predicted ionogram) calculated under a phasing model, for example, is most or closely similar to some hypothetical measured set of values (shown in the bottom graph as, e.g., an observed ionogram) under a least squares framework, for example. Such an approach is tolerant to phasing errors or effects, in the sense that rather than actually removing or correcting such phasing errors or effects from data to subsequently make base calls, the approach can yield base calls that in some way best reflect or take into account such phasing errors or effects. The solution may be found by searching or traversing possible sequences in various ways. For example, the search may be structured as a tree.

Figure 13:
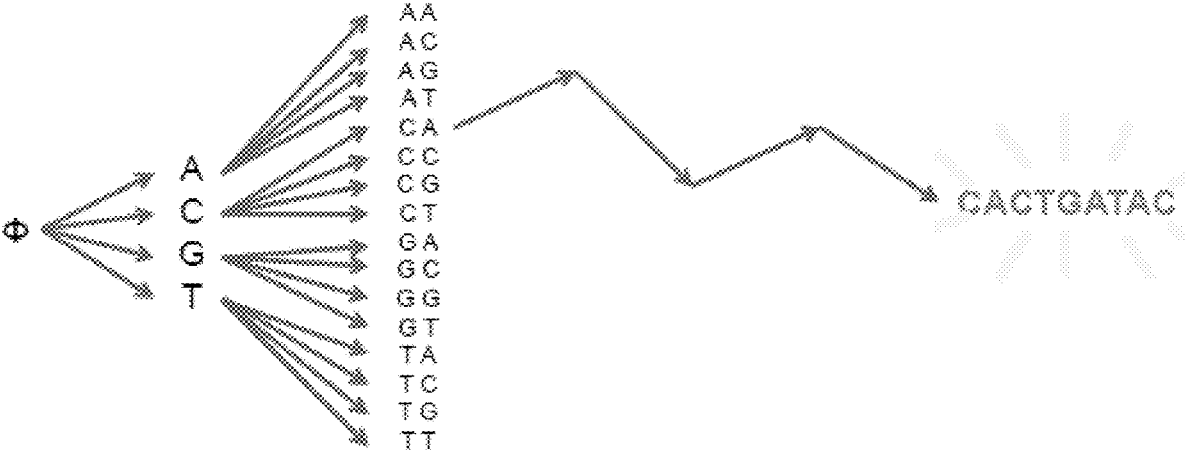
FIG. 13 illustrates a solver for making base calls.

FIG. 13 illustrates a solver for making base calls according to an exemplary embodiment. The solver may, for example, be a tree-based solver that determines a sequence of bases that are in some sense most or very consistent with measured data. For example, the solver may determine a sequence of bases (among some or all possible sequences having at most some given maximal length) for which predicted values that would be expected-under one or more models of underlying phenomena and related parameters if such a sequence were subjected to a given ordering of nucleotide flows—are in some sense most similar to measured values for templates actually subjected to the given ordering of nucleotide flows.

The generation of such a data structure may be incremental (e.g., one base at a time, or some number of bases at a time). For example, paths and predicted values may be generated for some partial sequence of length 4 (say, A. G. T, and C) to determine the next base (say, A) leading to a partial sequence of length 5 (say, A, G, T, C, and A) along the corresponding path, and so on. The partial sequences may be organized together, for example, to form a tree, and a "best" sequence may then be represented as a path through the data structure that identifies or leads to a best-fitting sequence under some appropriate metric. In other words, the solver may find the "correct sequence" (e.g., the actual physical base sequence to be determined) by looking at some or all possible sequences (or corresponding paths) having a length up to some selected or maximal length threshold, and determining which one is the "best-fitting sequence" (e.g., the sequence leading to predicted measurements that most closely fit with observed measurements). In an exemplary embodiment, the best-fitting sequence may be the sequence for which a sum of squared distance between an observed ionogram and a predicted ionogram is reduced or minimal.

It should be noted that although such a best-fitting sequence may correspond to or closely match the correct sequence, it is not necessarily the correct sequence both because one or more models used to generate the predicted ionogram may not necessarily reflect all underlying physical phenomena exactly, and because noise in measurements may sometimes cause an incorrect sequence to be a better fit to the observed data purely by chance. In addition, the best-fitting sequence may not always be the optimal solution under the models due to possible overfitting associated with a mismatch between the models and the data.

In such a structured approach, it is in principle possible to consider every possible sequence path or traversal (assuming some given maximal sequence length). However, such an exhaustive approach can be computationally time-consuming depending on complexity. Also, a large number of partial paths may not lead to the best-fitting or optimal sequence when extended and would thus be unnecessarily considered in an exhaustive approach. In an exemplary embodiment, with the use of appropriate metrics, a more efficient search considering some subset of the possible sequence paths may be performed. For example, a solver may examine partial sequence paths, eliminate some from further consideration, and then further examine more promising or informative ones. In an exemplary embodiment, the process of generating partial paths and associated predicted values may be incremental (e.g., one base at a time, or a predetermined numbers of bases at a time).

Figure 14:
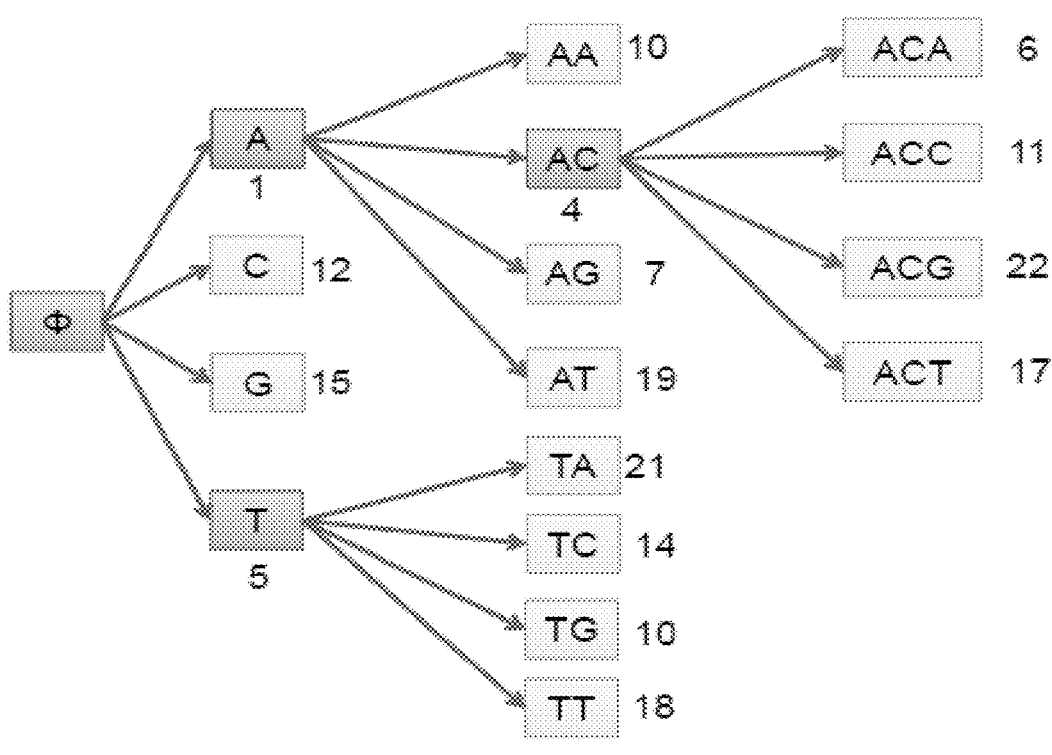
FIG. 14 illustrates a data structure with stepwise progression through partial sequence paths in a solver for making base calls.

FIG. 14 illustrates a data structure with stepwise progression through partial sequence paths in a solver for making base calls according to an exemplary embodiment. At the root of the data structure, illustrated in the single box in the first column, there is no base and an exemplary path metric may be assigned a value of zero. There are then four possible 1-nucleotide extensions (A, C, G, and T), which are illustrated in the boxes in the second column. The exemplary path metric has a value of 1 and 5 for nucleotides A and T, respectively, and a value of 12 and 15 for nucleotides C and G, respectively. Here, for example, the partial paths with lower metric values corresponding to nucleotides A and T are selected for further analysis and thus placed on the stack, whereas the partial paths with higher metric values corresponding to nucleotides C and G are not selected for future analysis and removed from the stack (of course, alternative metrics could be devised in which larger values are preferable). There are then four possible 1-nucleotide extensions (A, C, G, and T) for each of the two remaining partial paths, which are illustrated in the boxes in the third column (AA with value 10, AC with value 4, AG with value 7. AT with value 19, TA with value 21, TC with value 14, TG with value 10, and TT with value 18). At this stage, the partial path corresponding to AC has the lowest metric value and is selected for further analysis. There are then four possible 1-nucleotide extensions (A, C, G, and T) for that partial path, which are illustrated in the boxes in the fourth column (ACA with value 6, ACC with value 11. ACG with value 22, and ACT with value 17). This process could continue further to select additional bases along the ACA partial path, which has the lowest metric value at this point. Various criteria could be devised to determine how many paths to preserve at any given stage, which may be based on empirical observations or other rules.

Figure 15:
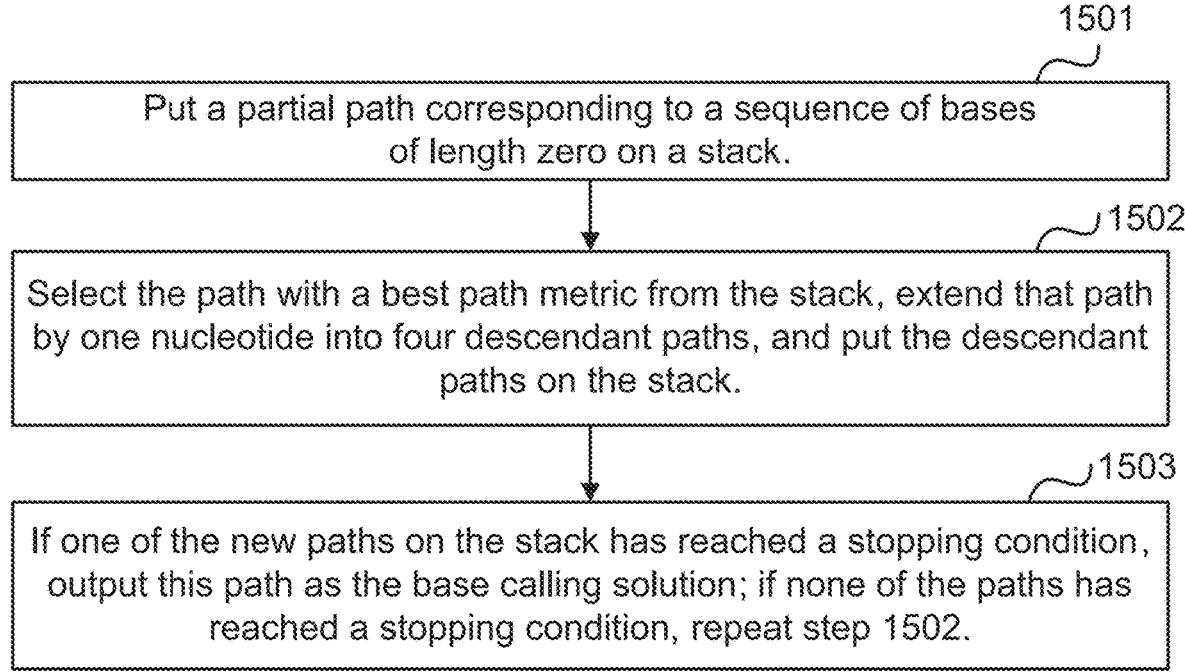
FIG. 15 illustrates a method for stepwise progression through partial sequence paths in a solver for making base calls.

FIG. 15 illustrates a method for stepwise progression through partial sequence paths in a solver for making base calls according to an exemplary embodiment. In step 1501, a server or other computing means or resource puts a partial path corresponding to a sequence of bases of length zero on a stack. In step 1502, a server or other computing means or resource selects the path with a best path metric from the stack, extends that path by one nucleotide into four descendant paths, and puts the descendant paths on the stack. In step 1503, a server or other computing means or resource determines if one of the new paths on the stack has reached a stopping condition and, if one has, outputs this path as the base calling solution: if none of the paths has reached a stopping condition, step 1502 is repeated.

The performance of such structured approaches may depend on making an appropriate selection of one or more path metric(s). Among full length sequences, a best or optimal fitting sequence, or sequence having a desired fit, may be the one having the lowest or smallest path metric (of course, alternative metrics could be devised in which larger values are preferable). For partial sequences, the path metric may be nondecreasing. It should be noted, however, that the length of the best fitting sequence need not be known a priori. Subject to the level of accuracy of underlying models of sequencing phenomena, path metrics may provide a mechanism in the context of the structured search to identify the best fitting sequence and thus make base calls in a manner that may be more accurate and/or efficient.

Because of phasing effects, individual pieces of observed or measured data (e.g., ionogram values) may be causally affected by multiple nucleotides. As a result, when calling bases (or homopolymers) one-by-one (sequentially), one may have to assume that some of the bases are yet undecided, and that their contribution to the measured data is unknown. Such difficulty in fully leveraging information embedded in measured data can increase risks of missing the global optimum. FIG. 16 illustrates a decision point between various exemplary paths in a solver for making base calls according to an exemplary embodiment. There, decision is between paths T-C-A, A-C, and G-G-A. A proper traversal search may overcome local minima and find a better solution. Further, a proper traversal search may end up terminating certain branches early on, and keeping more or less descendants in some branches, in an effort to carefully consider sets of partial sequences that are promising while rapidly removing from consideration sets of partial sequences that are not promising.

FIG. 17 illustrates a method for stepwise progression through partial sequence paths in a base calling solver according to an exemplary embodiment. In step 1701, a server or other computing means or resource puts a relatively small number of open paths on a stack (e.g., for one or more of the first few levels of a tree or other data structure) to help prevent overfitting and limit complexity. In step 1702, for every open path on the stack, a server or other computing means or resource calculates a set of predicted values (e.g., a predicted ionogram) for the four possible next path extensions from that path: evaluates, for each of the four possible next path extensions and under some appropriate criterion, how good a fit there is between the set of predicted values and corresponding measured values; and identifies which of the four possible next path extensions has a best fit and, if the fit is good enough under some appropriate threshold, ends that path and determines whether it is the best fitting path so far. In step 1703, a server or other computing means or resource terminates or abandons the least promising paths on the stack to maintain a relatively small number of open paths in order to prevent overfitting and limit complexity, which may include terminating or abandoning paths that are too far behind the longest one under some appropriate criterion and, in some cases when comparing paths of different length, terminating or abandoning paths having a path metric with a steepest slope.

In an exemplary embodiment, a base caller may be configured to calculate several metrics for each path. The metrics may be used alone or in various combinations to directly and/or indirectly evaluate the paths. The metrics may include a path metric (e.g., a metric that drives the selection of the next path on the stack to expand), a greedy decision metric (e.g., a local fit metric calculated for four descendants of a just extended path, which may be used in one or more absolute pruning rules), a per-flow metric (e.g., an auxiliary path metric used by a stack size limiting rule), a scaled residual (e.g., another local fit metric that may be used in one or more absolute pruning rules), and a total residual (e.g., a complementary measure to the path metric, which may be used in one or more absolute pruning rules and which may be such that a lowest total residual among visited paths constitutes a good upper bound for the path metric). In an embodiment, these metrics may be closely aligned to the manner in which a partial predicted ionogram is computed, which may done be according to a temporal phasing model as disclosed in Davey et al., U.S. patent application Ser. No. 13/283,320, filed Oct. 27, 2011, based on U.S. Prov. Pat. Appl. No. 61/407,377, filed on Oct. 27, 2010, which are both incorporated by reference herein in their entirety.

To further illustrate such metrics for some read pertaining to some defined space comprising sample nucleic acids subjected to a series of nucleotide flows, let L denote a number of nucleotide flows: let Y, denote an observed or measured intensity value representative of one or more nucleotide incorporation(s) (or lack thereof) for the samples in response to the ith nucleotide flow: let $Y(Y_1, Y_2 \ldots Y_L)$ denote an observed or measured ionogram or flowgram or other sequencing data (e.g., a vector comprising observed or measured intensity values such as, e.g., voltages or signals, responsive to the various nucleotide flows), and let $X=(X_1, X_2 \ldots X_L)$ denote a predicted ionogram or flowgram or other sequencing data for the path or partial sequence under consideration (e.g., a vector comprising predicted intensity values that would be expected in response to the various flows under one or more models of underlying physical sequencing phenomena). In addition, let (a,b) denote an active window within the nucleotide flows (where a and b respectively denote the earliest and the latest flow during which the last nucleotide in the partial sequence under consideration was incorporated by a substantial subpopulation of the polymerase molecules) and let $f$ denote an "in-phase flow" (e.g., an index for the flow at which the last base would have been incorporated in the absence of any phasing errors or effects).

In an embodiment, a path metric may be a sum of (i) a sum of squared residuals before an active window and (ii) a sum of squared residuals for negative residuals within the active window. For example, such a path metrics may be expressed as Equation 1.1.

$$PathMetric = \sum_{i=1}^{a-1}(Y_i - X_i)^2 + \sum_{i=a}^{b}\begin{cases} 0 & \text{if } (Y_i - X_i) > 0 \\ (Y_i - X_i)^2 & \text{if } (Y_i - X_i) < 0 \end{cases} \qquad \text{Eqn. 1.1}$$

A path metric may also be expressed as Equation 1.2, where $\delta$ and $\varepsilon$ are real numbers, which may differ from zero.

$$PathMetric = \sum_{i=1}^{a-1}(Y_i - X_i)^2 + \sum_{i=a}^{b}\begin{cases} \delta & \text{if } (Y_i - X_i) > \varepsilon \\ (Y_i - X_i)^2 & \text{if } (Y_i - X_i) < \varepsilon \end{cases} \qquad \text{Eqn. 1.2}$$

In an embodiment, a greedy decision metric may be a sum of (i) a product of an empirical constant and a sum of squared residuals for negative residuals within an active window and (ii) a sum of squared residuals for positive residuals within the active window but only before an in-phase flow. For example, such a greedy metrics may be expressed as Equation 2.1, where a is an empirical constant.

$$GreedyMetric = \alpha\sum_{i=a}^{b}\begin{cases} 0 & \text{if } (Y_i - X_i) > 0 \\ (Y_i - X_i)^2 & \text{if } (Y_i - X_i) < 0 \end{cases}^{+} \qquad \text{Eqn. 2.1}$$

33

-continued $$\sum_{i=a}^{f-1}\begin{cases}(Y_i - X_i)^2 & \text{if } (Y_i - X_i) > 0 \\ 0 & \text{if } (Y_i - X_i) < 0\end{cases}.$$

A greedy decision metric may also be expressed as Equation 2.2, where $\beta$, $\gamma$, $\delta$, and $\varepsilon$ are real numbers, which may differ from zero.

$$GreedyMetric = \alpha \sum_{i=a}^{b}\begin{cases}\beta & \text{if } (Y_i - X_i) > \gamma \\ (Y_i - X_i)^2 & \text{if } (Y_i - X_i) < \gamma\end{cases} + \qquad \text{Eqn. 2.2}$$

$$\sum_{i=a}^{f-1}\begin{cases}(Y_i - X_i)^2 & \text{if } (Y_i - X_i) > \varepsilon \\ \delta & \text{if } (Y_i - X_i) < \varepsilon\end{cases}.$$

In an embodiment, a per-flow metric may be a weighted sum of (i) a path metric as described above and (ii) a greedy decision metric as described above. For example, the per-flow metric may be expressed as Equation 3.1, where A may be substantially equal to $1/f$ and B may be substantially equal to $0.5/f$, where $f$ denotes the in-phase flow.

Eqn. 3.1: PerFlowMetric=A(PathMetric)+B(Greedy Metric).

In an embodiment, a scaled residual may be a ratio of (i) a difference between an observed or measured value for a current path at a current in-phase flow and a predicted value from a parent path at the current in-phase flow and (ii) a difference between a predicted value of the current path at the current in-phase flow and a predicted value from the parent path at the current in-phase flow. For example, a scaled residual may be expressed as Equation 3.2.

$$ScaledResidual = \frac{Y_f - Z_f}{X_f - Z_f}. \qquad \text{Eqn. 3.2}$$

In an embodiment, a total residual may be a sum of squared residuals over all nucleotide flows. For example, the total residual may be expressed as Equation 4.1.

$$TotalResidual = \sum_{i=1}^{L}(Y_i - X_i)^2. \qquad \text{Eqn. 4.1}$$

In various embodiments, some or all of the foregoing metrics may be used to allow a more efficient search through and consideration of possible sequences of bases. In an exemplary embodiment, some or all of the foregoing metrics may be used to perform pruning, which may include removing selected paths from the stack to minimize and/or ameliorate possible model overfitting considerations while improving speed. This may obviate the need to spend computational resources considering paths that likely do not lead to the correct sequence, and reduce risks of reporting such likely erroneous paths as final solution. However, pruning may also have downsides. For example, a path removed through pruning may actually lead to the correct sequence. In an exemplary embodiment, to maximize the benefits of pruning while minimizing potential downsides, there is provided a set of rules that are sensitive (e.g., having a low likelihood of removing paths leading to the correct sequence) and specific (e.g., achieving removal of a large number of other paths).

Various rules may be used for pruning, including "absolute" pruning rules and "relative" pruning rules. Absolute pruning rules include rules adapted to decide whether a path is to be removed without any dependency on other paths on the stack. Such absolute rules act on new paths created in an extension step, and usually act quickly. Relative pruning rules include rules adapted to decide whether a path is to be removed depending on other paths on the stack. Such relative rules may entail periodic scanning of the stack for paths that match the rule at a given point in time (even though in some cases the same paths may not previously have matched the rule).

Figure 18A:
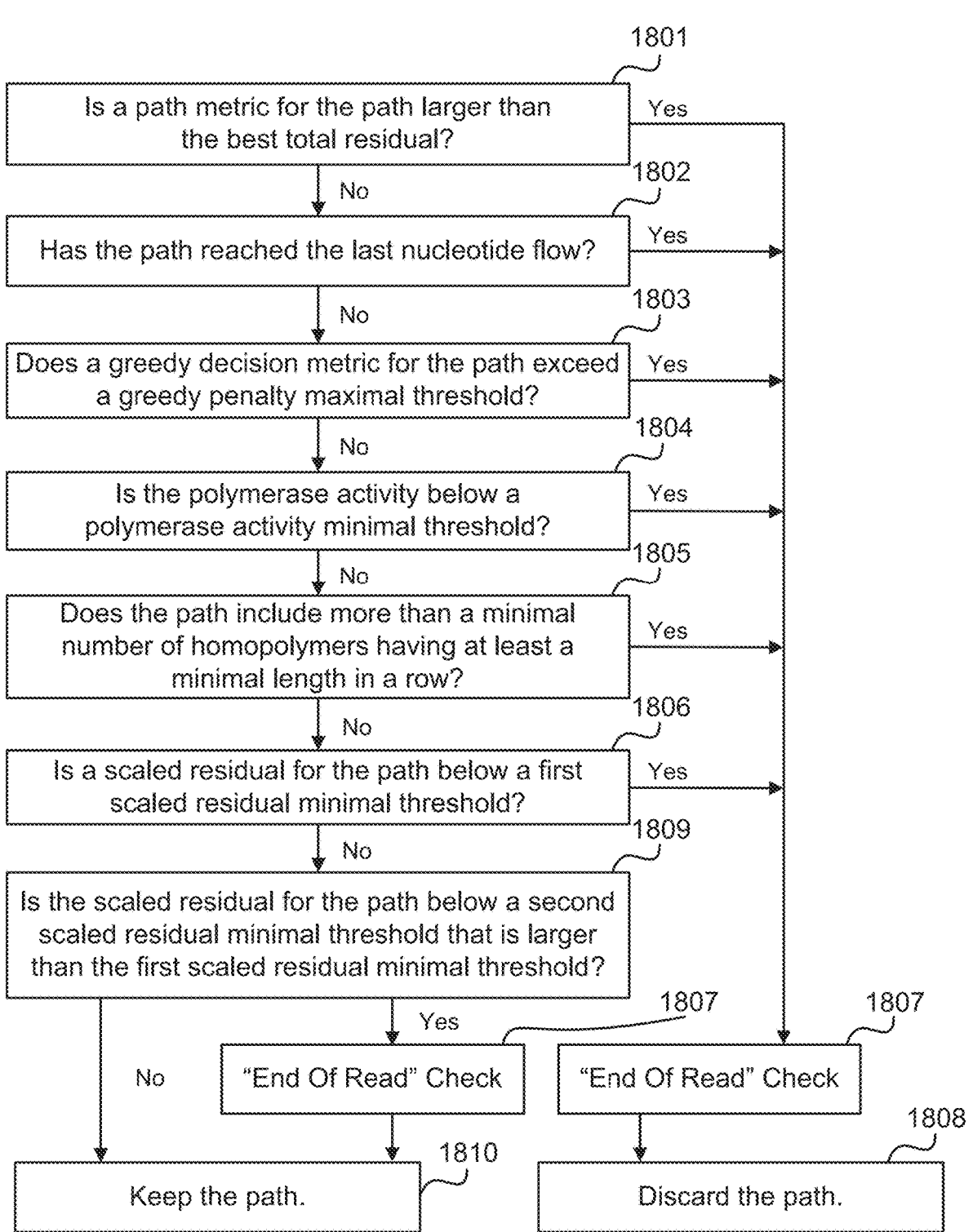
FIG. 18A illustrates a base calling pruning method including absolute pruning for a best greedy expansion.

FIG. 18A illustrates a base calling pruning method including absolute pruning for a best greedy expansion according to an exemplary embodiment. In step 1801, a server or other computing means or resource determines, for a best greedy expansion (the descendant path with the lowest greedy decision metric), whether the path metric for the path is larger than the best total residual. If it is, then in step 1807, a server or other computing means or resource performs a final check whether the path has a lowest total residual than the best path seen so far, and then in step 1808, a server or other computing means or resource discards the path. If not, then in step 1802, a server or other computing means or resource determines whether the path has reached the last nucleotide flow. If it has, then a server or other computing means or resource performs steps 1807 and 1808 as discussed above. If not, then in step 1803, a server or other computing means or resource determines whether a greedy decision metric for the path is very high under some appropriate measure (e.g., exceeds a greedy penalty maximal threshold). If it is, then a server or other computing means or resource performs steps 1807 and 1808 as discussed above. If not, then in step 1804, a server or other computing means or resource determines whether polymerase activity is low under some appropriate measure (e.g., below a polymerase activity minimal threshold). If it is, then a server or other computing means or resource performs steps 1807 and 1808 as discussed above. If not, then in step 1805, a server or other computing means or resource determines whether the path includes multiple long homopolymers in a row (e.g., more than a minimal number of homopolymers having at least a minimal length in a row). If it does, then a server or other computing means or resource performs steps 1807 and 1808 as discussed above. If not, then in step 1806, a server or other computing means or resource determines whether a scaled residual is very low under some appropriate measure (e.g., below a first scaled residual minimal threshold). If it is, then a server or other computing means or resource performs steps 1807 and 1808 as discussed above. If not, then in step 1809, a server or other computing means or resource determines whether the scaled residual is low under some appropriate measure (e.g., below a second scaled residual minimal threshold that is larger than the first scaled residual minimal threshold). If it is, then a server or other computing means or resource performs step 1807 as discussed above, and then in step 1810, a server or other computing means or resource keeps the path. If not, then a server or other computing means or resource performs step 1810 as discussed above. In various exemplary embodiments, only a subset of these rules may be used, and they may be used in a different order. Any of the threshold parameters for these rules may be set based on empirical observations or using any other means, which may entail making one or more assumptions about underlying phenomena to determine reasonable parameters.

FIG. 18B illustrates a base calling pruning method including absolute pruning for another expansion than a best greedy expansion according to an exemplary embodiment. Aside from the best greedy expansion (the descendant path with the lowest greedy decision metric), there may be three other expansions. In step 1811, a server or other computing means or resource determines whether the best greedy expansion has been discarded already. If it has, then in step 1816, a server or other computing means or resource discards the path. If not, then in step 1812, a server or other computing means or resource determines whether a greedy decision metric for this expansion exceeds the greedy decision metric for the best greedy expansion by more than a maximal threshold. If it does, then a server or other computing means or resource performs step 1816 as discussed above. If not, then in step 1813, a server or other computing means or resource determines whether the path metric is larger than the best total residual. If it is, then a server or other computing means or resource performs step 1816 as discussed above. If not, then in step 1814, a server or other computing means or resource determines whether the path has reached the last nucleotide flow. If it has, then a server or other computing means or resource performs step 1816 as discussed above. If not, then in step 1815, a server or other computing means or resource determines whether a scaled residual is very low under some appropriate measure (e.g., below a first scaled residual minimal threshold). If it is, then a server or other computing means or resource performs step 1816 as discussed above. If not, then in step 1817, a server or other computing means or resource keeps the path.

In an exemplary embodiment, there is provided a method for pruning a data structure comprising paths or traversals representing candidate nucleic acid sequences, including using one or more rules or conditions for determining whether to keep or discard one or more of the paths. The one or more rules or conditions may include one or more one or more absolute pruning rules selected from the group comprising: (i) discarding paths having a path metric larger than a best total residual metric, (ii) discarding paths having reached a last nucleotide flow, (iii) discarding paths for which a greedy decision metric exceeds a greedy penalty maximal threshold. (iv) discarding paths for which a polymerase activity is below a polymerase activity minimal threshold. (v) discarding paths including more than a threshold number of homopolymers having at least a threshold length in a row, (vi) discarding paths having a scaled residual metric below a first scaled residual minimal threshold, (vii) discarding paths having a scaled residual below a second scaled residual minimal threshold that is larger than the first scaled residual minimal threshold, and (viii) discarding paths having a greedy decision metric that exceeds the greedy decision metric for a best greedy expansion by more than a maximal threshold.

The one or more rules or conditions may also include one or more relative pruning rules selected from the group comprising: (i) a maximum delay rule (e.g., discarding paths being more than a certain number of base pairs shorter than a longest path in the structure), and (ii) a stack size limiting rule (e.g., discarding paths having a highest per-flow metric whenever the number of paths exceeds a certain threshold or K value).

Various methods may be used to efficiently generate partial predicted ionograms or other sequencing data, including temporal phasing models for incrementally generating partial sequences and corresponding partial ionograms (e.g., one base at a time) and simulation and/or dynamic programming calculation of predicted ionograms or other sequencing data.

FIG. 19 illustrates a path predicted signal and a path residual according to an exemplary embodiment. The predicted signal shows values $X_1$, and the path residual shows values $Y_i-X_1$. Also shown are the flow for the current incorporation and the active window around such flow, which is preceded by a determined residual and followed by an undetermined residual. The metrics (e.g., penalty) may depend on the residual in the active window; and may take into account the negative residuals in the active window and the positive residuals left of the current incorporation, as discussed previously.

FIG. 20 illustrates schematically a temporal model for modeling times at which a polymerase incorporates a nucleotide according to an exemplary embodiment. The nucleotide flows are labeled by number (1 through 20 in the top panel and 102 through 125 in the bottom panel) and by type of flowed nucleotide. Because the flows occur one after the other, a progression along flow numbers also denotes a progression along time. The top panel shows a histogram of flows during which a base (e.g., an exemplary $6^{th}$ base T) is incorporated. As shown, in most cases the T is incorporated during the $9^{th}$ flow, which is the in-phase flow. However, in a few cases the T is incorporated during the $5^{th}$, $11^{th}$, or $17^{th}$ flow; which may be due to possible phasing errors or effects leading to some templates having fallen behind or moved forward relative to main population. The bottom panel shows a histogram of flows during which another base (e.g., an exemplary $50^{th}$ base A) is incorporated. As shown, in most cases the A is incorporated during the $109^{th}$ flow, which is the in-phase flow. However, in a few cases the A is incorporated during the $102^{nd}$, $112^{th}$ $116^{th}$, $120^{th}$, or $124^{th}$ flow, which again may be due to possible phasing errors or effects. Because the $50^{th}$ base is further along than the $6^{th}$ base, the distribution of times at which incorporation occur tends to be more spread out, which is to be expected given that the more sequencing has progressed the more opportunities for phasing errors or effects have been encountered.

Figure 21:
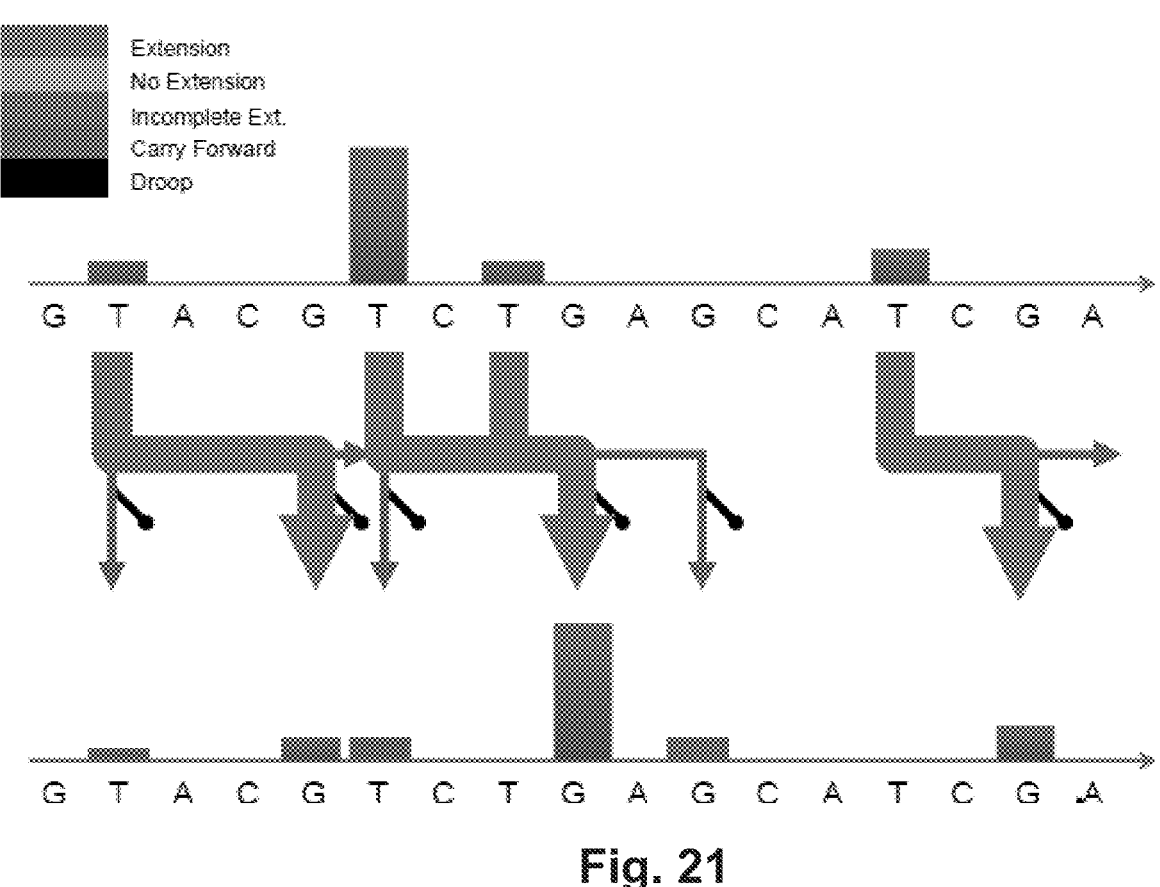
FIG. 21 illustrates schematically a temporal model for modeling times at which a polymerase incorporates a nucleotide.

FIG. 21 illustrates schematically a temporal model for modeling times at which a polymerase incorporates a nucleotide according to an exemplary embodiment. The flows are labeled by type of flowed nucleotide. Because the flows occur one after the other, a progression along flowed nucleotides from left to right also denotes a progression along time. The top panel shows a histogram of flows during which a base (e.g., an exemplary $6^{th}$ base T) is incorporated. As shown, in most cases the T is incorporated during the $6^{th}$ flow, which is the in-phase flow: However, in a few cases the T is incorporated during the $2^{nd}$, $8^{th}$, or $14^{th}$ flow: The bottom panel shows a histogram of flows during which the next base (e.g., an exemplary $7^{th}$ base G) is incorporated. As shown, in most cases the G is incorporated during the $9^{th}$ flow; which is the in-phase flow. However, in relatively few cases the G is incorporated during the $2^{nd}$, $5^{th}$, $6^{th}$, $11^{th}$, or $16^{th}$ flow:

To better understand how and when the next base incorporates in the bottom panel of FIG. 21 given the situation in the top panel, it may help to look at the populations one by one. The G incorporation in the $2^{nd}$ flow results from a leftover G nucleotide that may have remained from the 1st flow (e.g., at the second flow, the polymerase incorporates both a T and a G, which is sometimes called a carry-over event). The G incorporation in the $5^{th}$ flow results from the normal extension process for those templates that incorporated a T in the $2^{nd}$ flow and stood ready to incorporate at the next flow of G. The G incorporation in the $6^{th}$ flow results from a leftover G nucleotide that may have remained from the $5^{th}$ flow (e.g., another carry-over event). The G incorporation in the $9^{th}$ flow results from the normal extension process for those templates that incorporated a T in the $6^{th}$ or $8^{th}$ flow, and stood ready to incorporate at the next flow of G. The G incorporation in the $11^{th}$ flow results from a relatively small number of those templates that incorporated a T in the $2^{nd}$. $6^{th}$, or $8^{th}$ flow and stood ready to incorporate at the next flow of G but for whatever reason did not incorporate when G was flowed (which is sometimes called an incomplete extension event). Finally, the G incorporation in the $16^{th}$ flow results from the normal extension process for those templates that incorporated a T in the $14^{th}$ flow and stood ready to incorporate at the next flow of G.

In various embodiments, partial paths being considered may be associated with both a partial predicted signal (e.g., a partial predicted ionogram or other sequencing data) and a histogram of flows during which the last nucleotide was incorporated.

Figure 22:
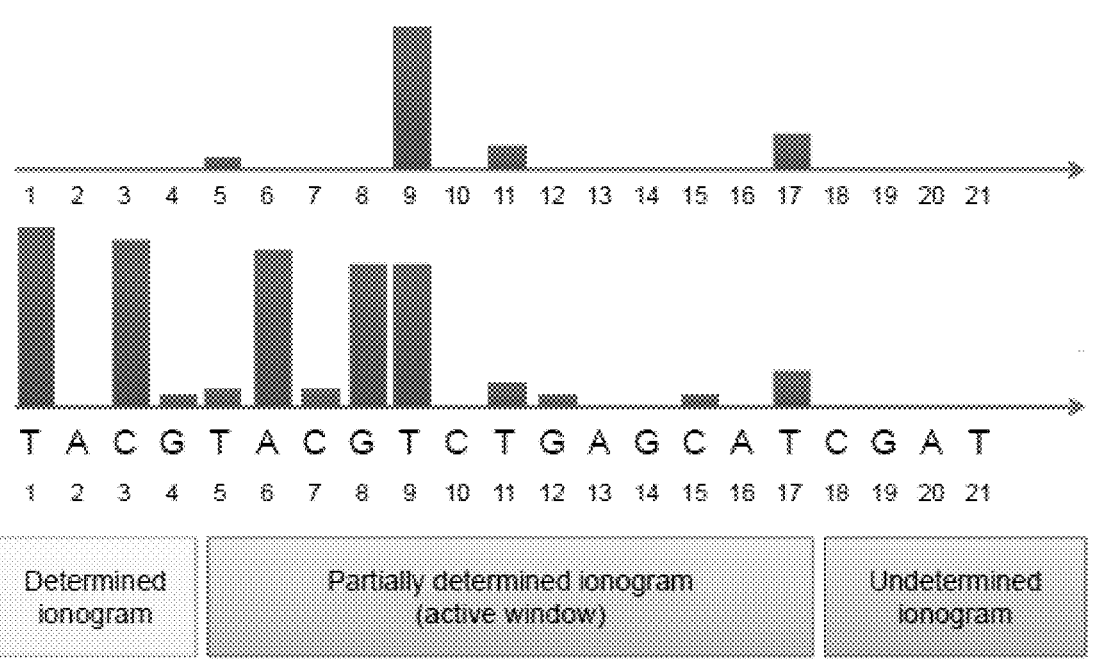
FIG. 22 illustrates a partial predicted signal and a histogram of flows during which the last nucleotide was incorporated that are associated with a base sequence of length 5 ending with T.

FIG. 22 illustrates a partial predicted signal and a histogram of flows during which the last nucleotide was incorporated that are associated with a base sequence of length 5 ending with T according to an exemplary embodiment. The top panel shows a histogram of flows during which a base (e.g., an exemplary $5^{th}$ base) is incorporated. The essentially nonzero populations in this histogram are contained within the active window (e.g., flows 5 through 17 in this example). The middle panel shows a sum of incorporation signals from bases 1 through 5 (thus including that of the top panel). The bottom panel shows three flow windows. On the left is a window corresponding to the first four flows, for which the corresponding ionogram has been determined. Since the fifth base was incorporated in flows 5 and later in this example, any subsequent bases by which this path may be extended, must necessarily also be incorporated no earlier than flow 5, leaving flows 1 through 4 unchanged. In the middle is the active window, where the ionogram has only been partially determined (e.g., flows 5 through 17 in this example). Some of the initial 5 bases already contributed signal to incorporation signal within this range, and subsequent bases by which this path may be extended can contribute further signal. On the right is a window corresponding to the flows starting with the $18^{th}$ flow, for which the corresponding ionogram has not been determined. The initial 5 bases have not contributed any signal here, but subsequent bases by which this path may be extended can contribute. Generally, for any given path the solver may maintain a window having expected populations defined by a phasing model.

Figure 23A:
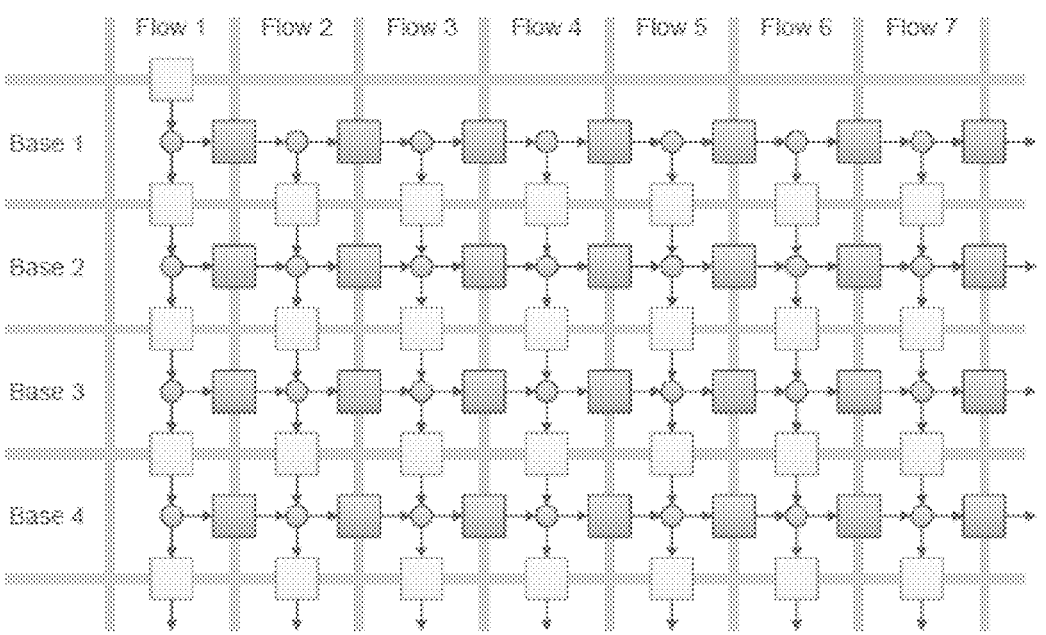
FIG. 23A illustrates schematically a simulation framework for calculating predicted ionograms.

FIG. 23A illustrates schematically a simulation framework for calculating predicted ionograms according to an exemplary embodiment. The representation includes various steps and can be thought of as a matrix of flows (see columns representing flows 1, 2, 3, and so on) and bases (see rows representing bases 1, 2, 3, and so on. Bases may or may not incorporate in response to the flows, as further described next, and simulations of incorporations (or absence thereof) generate paths along the cells of such a matrix.

Figure 23B:
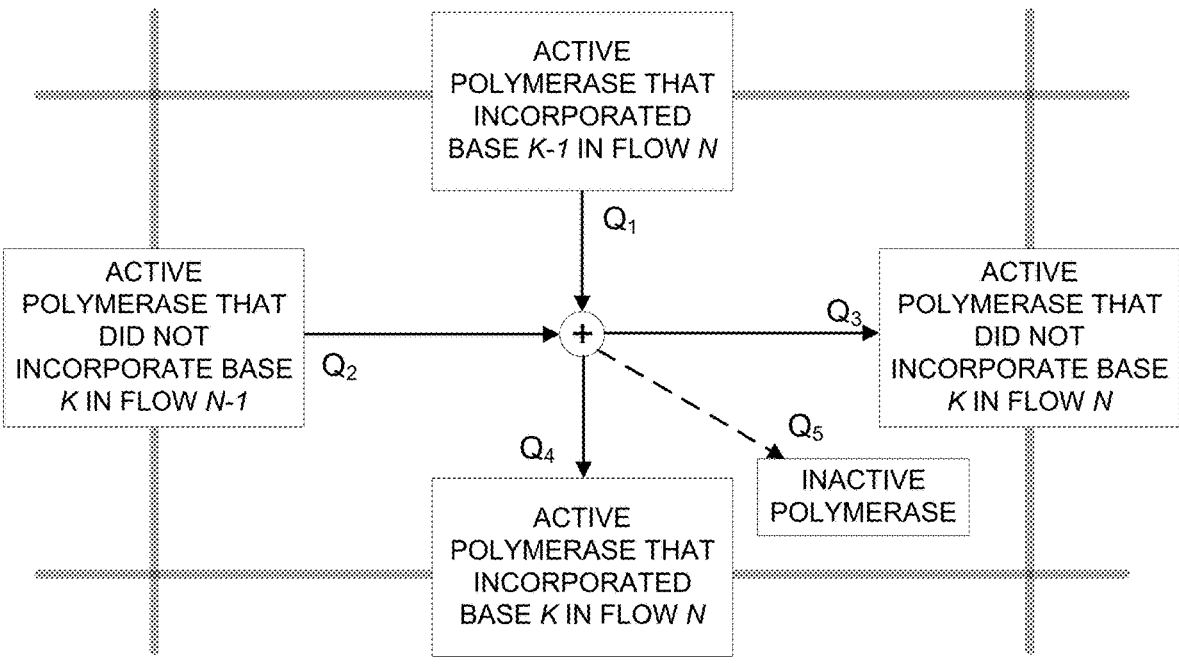
FIG. 23B illustrates an exemplary cell within a matrix as illustrated in FIG. 23A along with possible states and state transitions.

FIG. 23B illustrates an exemplary cell within a matrix as illustrated in FIG. 23A along with possible states and state transitions according to an exemplary embodiment. Such a cell illustrates what may happen for an active polymerase present at the K-th base during the N-th flow. To arrive at this point, the polymerase either incorporated base K-/in flow N or did not incorporate base K in flow N-1. There are then several possibilities. The polymerase may undergo normal extension or a carry-forward event, and incorporate base K in flow N. The polymerase may also fail to extend or undergo an incomplete extension event, and not incorporate base K in flow N. Finally, the polymerase may become inactive and thus undergo droop. For a population of polymerase, the proportion of polymerase in the possible subsequent states will depend on the incoming populations and state transition parameters.

Referring to the exemplary cell within a matrix as illustrated in FIG. 23B, in situations where the K-th base matches the N-th flow, the proportion of polymerase that will remain active and not incorporate base K in flow N (e.g., $Q_3$) may be determined by multiplying some measure of the quantity (e.g., number, concentration, etc.) of polymerase in the two prior states (e.g., $Q_1$. $Q_2$) by a transition factor comprising term $[IER \times (1-DR)]$, where IER is an incomplete extension rate and DR is a droop rate. Conversely, the proportion of polymerase that will remain active and incorporate base K in flow N (e.g., $Q_4$) may be determined by multiplying some measure of the quantity (e.g., number, concentration, etc.) of polymerase in the two prior states (e.g., $Q_1$. $Q_2$) by a transition factor comprising term $[(1-IER) \times (1-DR)]$.

Referring to the exemplary cell within a matrix as illustrated in FIG. 23B, in situations where the K-th base does not match the N-th flow, the proportion of polymerase that will remain active and not incorporate base K in flow N (e.g., $Q_3$) may be determined by multiplying some measure of the quantity (e.g., number, concentration, etc.) of polymerase in the two prior states (e.g. $Q_1$, $Q_2$) by a transition factor comprising term $[(1-(FR). (CFR^M \times IER \times (1-DR))]$, where CFR is a carry forward rate and M is the smallest number such that the (N−M)-th flow matches the K-th base. Conversely, the proportion of polymerase that will remain active and incorporate base K in flow N (e.g., $Q_4$) may be determined by multiplying some measure of the quantity (e.g., number, concentration, etc.) of polymerase in the two prior states (e.g., $Q_1 \cdot Q_2$) by a transition factor comprising term $[CFR^M \times (1-IER) \times (1-DR)]$.

The IER, CFR, and DR values may be determined using any suitable approach, including as disclosed in Davey et al., U.S. patent application Ser. No. 13/283,320, filed Oct. 27, 2011, based on U.S. Prov. Pat. Appl. No. 61/407,377, filed on Oct. 27, 2010, which are both incorporated by reference herein in their entirety.

Figures 24A, 24B, 24C:
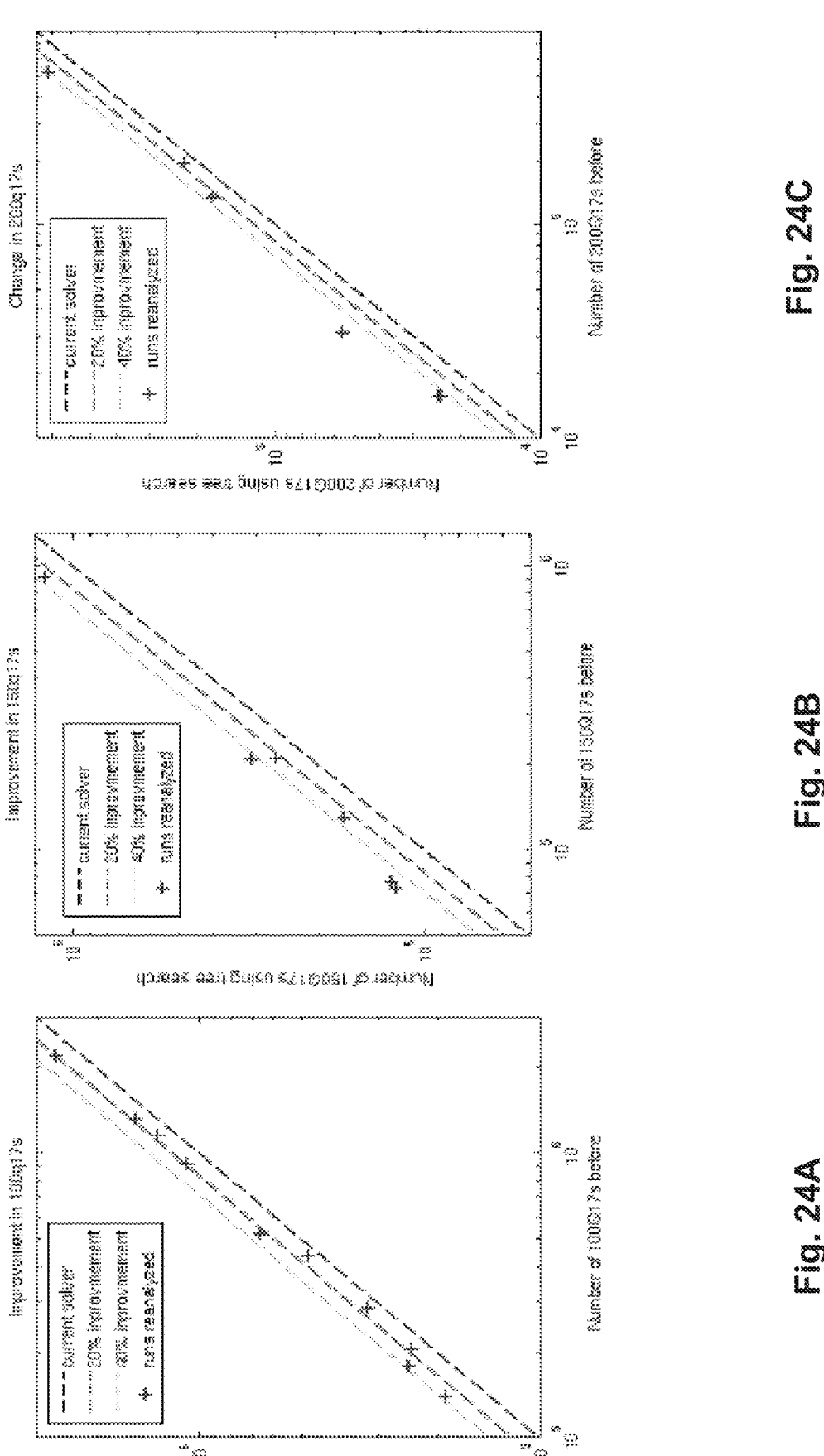
FIGS. 24A-24C illustrate improvements in performance associated with use of a solver for making base calls.

FIGS. 24A-24C illustrate improvements in performance associated with use of a solver for making base calls according to an exemplary embodiment. The figures show the number of 100Q17 reads (reads that achieve error rate less or equal than 2% over 100 or more initial bases), 150Q17 reads (reads that achieve error rate less or equal than 2% over 150 or more initial bases), and 200Q17 reads (reads that achieve error rate less or equal than 2% over 200 or more initial bases), respectively both without (x-axis) and with (y-axis) use of structured (e.g., tree) searching. The solid dashed line shows the line with slope of 1 dividing the quadrant in two and showing points where performance would be identical with the two methods. The two other dashed lines show points where performance would be improved by 20% and 40%. As shown, in all three cases all the reanalyzed runs (see crosses) lead to improvements, which exceeded 40% in about five of the reanalyzed runs in FIGS. 24B-24C.

Figure 25A:
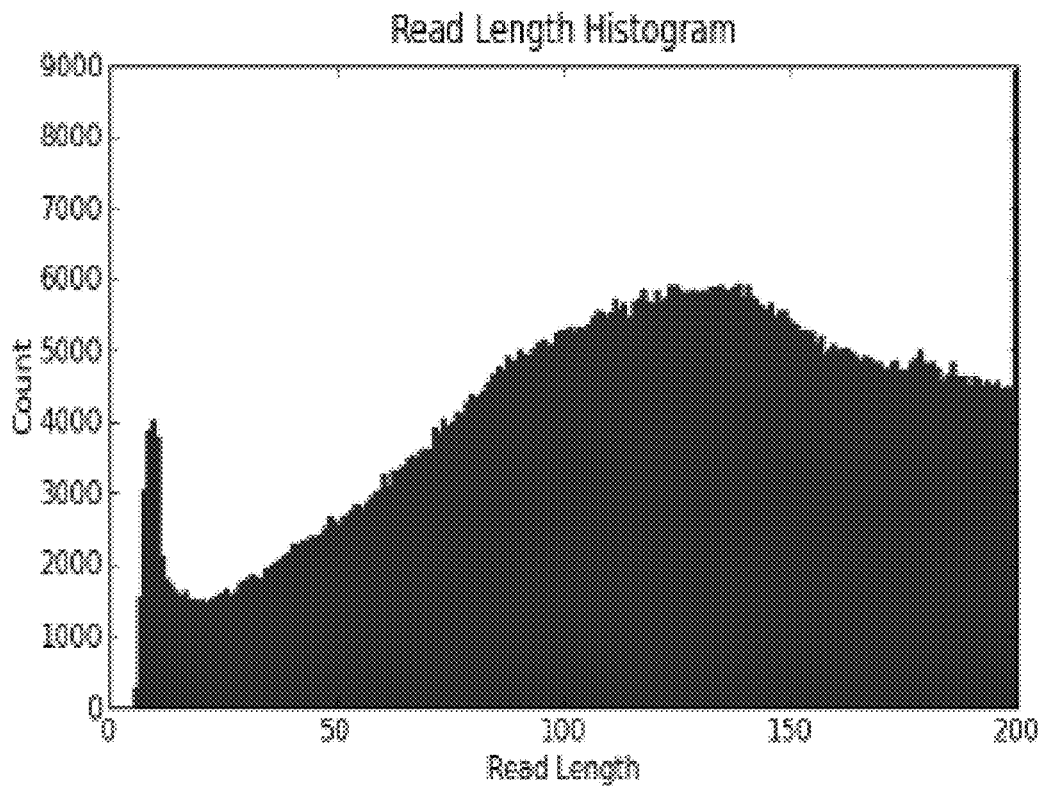
FIGS. 25A-25B illustrate improvements in read length distributions associated with use of a solver for making base calls.
Figure 25B:
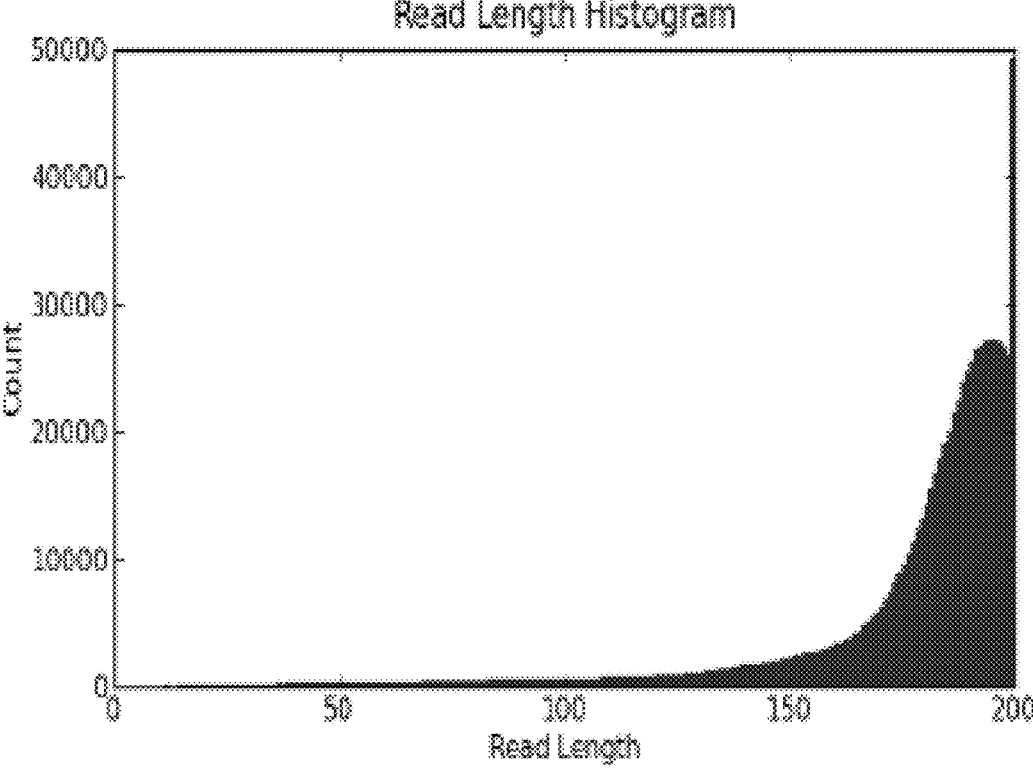

FIGS. 25A-25B illustrate improvements in read length distributions associated with use of a solver for making base calls according to an exemplary embodiment. FIG. 25A shows a histogram of read lengths for 209.101 $150Q_{17}$ reads without structured searching. FIG. 25B shows a histogram of read lengths for 310,650 150$Q_{17}$ reads with structured searching. The histograms show that using structured searching may render more long reads with a desired confidence observable and result in a smoother distribution of read lengths.

Figure 26A:
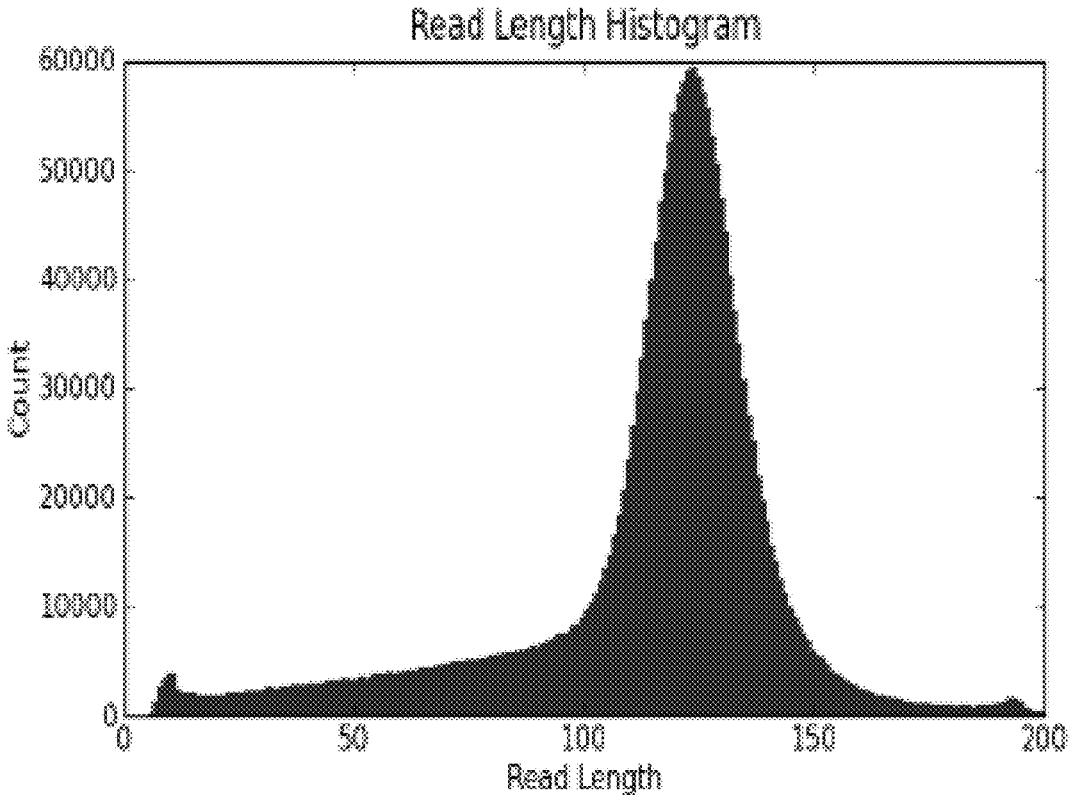
FIGS. 26A-26B illustrate improvements in read length distributions associated with use of a solver for making base calls.
Figure 26B:
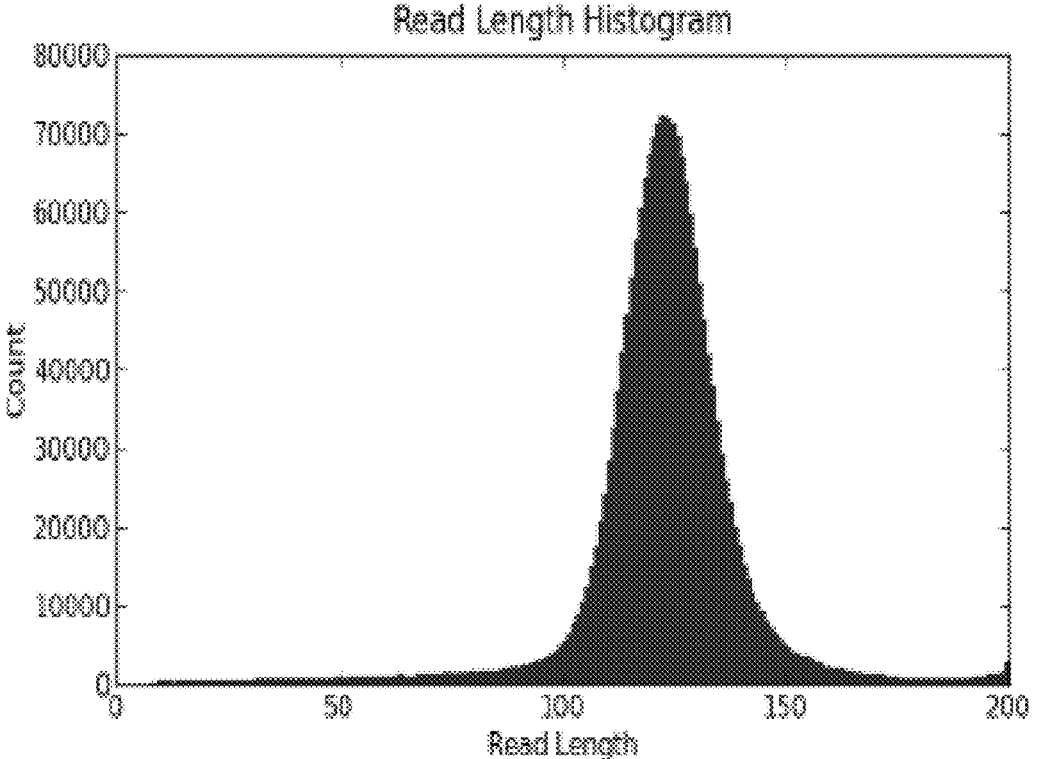

FIGS. 26A-26B illustrate improvements in read length distributions associated with use of a solver for making base calls according to an exemplary embodiment. FIG. 26A shows a histogram of read lengths for 820,036 100$Q_{17}$ reads without structured searching. FIG. 26B shows a histogram of read lengths for 1.022.467 100$Q_{17}$ reads with structured searching. The histograms show that using structured searching may render more long reads with a desired confidence observable and result in a smoother distribution of read lengths. In particular, the left tail of the distribution is significantly smaller when using structured searching and does not include a distinct peak at the very left.

FIG. 27 illustrates a method of nucleic acid sequencing according to an exemplary embodiment. In step 2701, a module or other hardware and/or software component receives a plurality of observed or measured signals indicative of a parameter observed or measured for a plurality of defined spaces or reaction confinement regions, at least some of the defined spaces or reaction confinement regions comprising one or more sample nucleic acids, the observed or measured signals being responsive to a plurality of nucleotide flows introducing nucleotides to the defined spaces. In step 2702, a module or other hardware and/or software component determines, for at least some of the defined spaces or reaction confinement regions, whether the defined space or reaction confinement region comprises one or more sample nucleic acids. In step 2703, a module or other hardware and/or software component processes, for at least some of the defined spaces or reaction confinement regions determined to comprise one or more sample nucleic acids, the observed or measured signal for the defined space or reaction confinement region to improve a quality of the observed or measured signal. In step 2704, a module or other hardware and/or software component generates, for at least some of the defined spaces or reaction confinement regions determined to comprise one or more sample nucleic acids and processed in the processing step, a set of candidate sequences of bases for the defined space or reaction confinement region using one or more metrics adapted to associate a score or penalty to the candidate sequences of bases. In step 2705, a module or other hardware and/or software component selects from the generated sequences of bases the candidate sequence leading to a highest score or a lowest penalty as corresponding to the correct sequence for the one or more sample nucleic acids in the defined space or reaction confinement region.

Figures 28, 29:
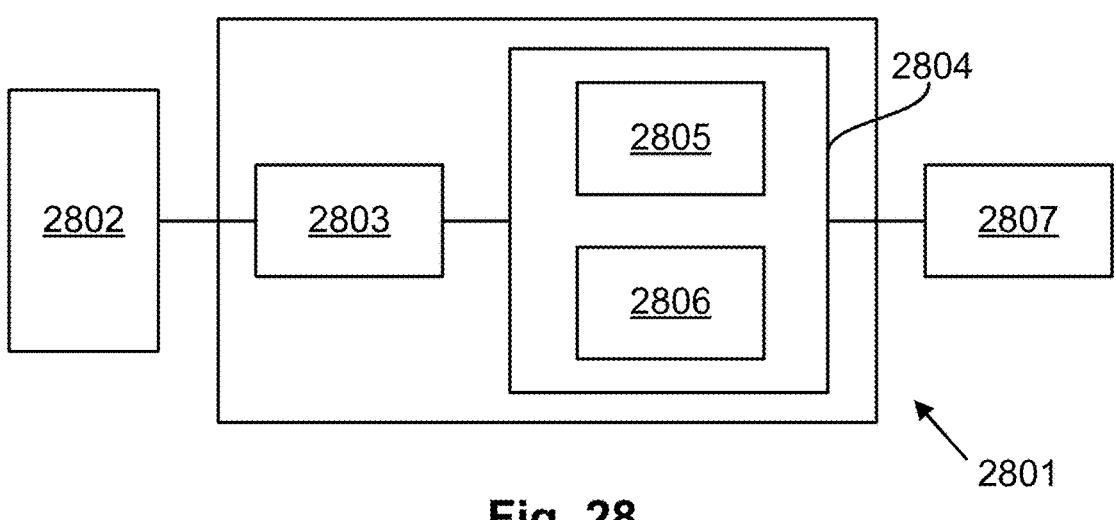
FIG. 28 illustrates a system for nucleic acid sequencing.
FIG. 29 illustrates a correlation plot showing empirical vs. predicted quality scores.

FIG. 28 illustrates a system 2801 for nucleic acid sequencing according to an exemplary embodiment. The system includes a reactor array 2802: a reader board 2803: a computer and/or server 2804, which includes a CPU 2805 and a memory 2806; and a display 2807, which may be internal and/or external. One or more of these components may be used to perform or implement one or more aspects of the exemplary embodiments described herein.

According to an exemplary embodiment, there is provided a method for nucleic acid sequencing, comprising (1) receiving a plurality of observed or measured signals indicative of a parameter observed or measured for a plurality of defined spaces, at least some of the defined spaces comprising one or more sample nucleic acids, the observed or measured signals being responsive to a plurality of nucleotide flows introducing nucleotides to the defined spaces: (2)

determining, for at least some of the defined spaces, whether the defined space comprises one or more sample nucleic acids: (3) processing, for at least some of the defined spaces determined to comprise one or more sample nucleic acids, the observed or measured signal for the defined space to improve a quality of the observed or measured signal: (4) generating, for at least some of the defined spaces determined to comprise one or more sample nucleic acids and processed in the processing step, a set of candidate sequences of bases for the defined space using one or more metrics adapted to associate a score or penalty to the candidate sequences of bases; and (5) selecting from the generated sequences of bases the candidate sequence leading to a highest score or a lowest penalty as corresponding to the correct sequence for the one or more sample nucleic acids in the defined space.

In such a method, the parameter observed or measured for the defined spaces may comprise a voltage measurement indicative of hydrogen ion concentration for respective defined spaces or a measurement substantially proportional to a light or fluorescent intensity for respective defined spaces. Generating the set of candidate sequences may comprise generating a data structure comprising a set of partial paths corresponding to candidate sequences undergoing expansion in a stepwise manner one base at a time. Generating the data structure may comprise determining a predicted signal for each partial path and evaluating a distance between the predicted signal and an observed or measured signal.

In such a method, the one or more metrics may comprise a metric that is a function of the distance between the predicted signal and the observed or measured signal, and may comprise a metric comprising a sum of squared distances between corresponding values of the predicted signal and the observed or measured signal. The one or more metrics may comprise one or more of (1) a path metric comprising a sum of (i) a sum of squared residuals before an active window and (ii) a sum of squared residuals for negative residuals within the active window: (2) a path metric expressed as Equation 1.1 or 1.2, where $Y_1$, represents an observed or measured value responsive to an i-th nucleotide flow. X represents a predicted value responsive to the i-th nucleotide flow, $\alpha$ represent an index for a first nucleotide flow in an active window, b represent an index for a last nucleotide flow in the active window, $\delta$ is a real number, and $\varepsilon$ is a real number: (3) a greedy decision metric comprising a sum of (i) a product of an empirical constant and a sum of squared residuals for negative residuals within an active window and (ii) a sum of squared residuals for positive residuals within the active window but only before an in-phase flow: (4) a greedy decision metric expressed as Equation 2.1 or 2.2, where $Y_1$ represents a observed or measured value responsive to an i-th nucleotide flow, X represents an predicted value responsive to the i-th nucleotide flow, $\alpha$ represents an index for a first nucleotide flow in an active window, b represent an index for a last nucleotide flow in the active window, $f$ represents an index for an in-phase flow, a is an empirical constant. $\delta$ is a real number, $\gamma$ is a real number, $\delta$ is a real number, and $\varepsilon$ is a real number: (5) a path metric, a greedy decision metric, and a per-flow metric, and wherein the per-flow metric comprises a weighted sum of (i) the path metric and (ii) the greedy decision metric: (6) a path metric, a greedy decision metric, and a per-flow metric, and wherein the per-flow metric is expressed as a sum of (i) a product of a factor substantially equal to 1 $f$ and the path metric and (ii) a product of a factor substantially equal to 0.5 $f$ and the greedy decision metric, where $f$ represents an index for an in-phase flow: (7) a scaled residual comprising a ratio between (i) a difference between an observed or measured value for a current path at a current in-phase flow and a predicted value from a parent path at the current in-phase flow and (ii) a difference between a predicted value of the current path at the current in-phase flow and a predicted value from the parent path at the current in-phase flow: (8) a scaled residual expressed as Equation 3.1, where $Y_f$ represents an observed or measured value at the in-phase flow $f$. $Z_f$ represents a predicted value at an in-phase flow $f$, and X represents a predicted value at the in-phase flow $f$. (9) a total residual comprising a sum of squared residuals over all nucleotide flows; and (10) a total residual expressed as Equation 4.1, where $Y_1$, represents an observed or measured value responsive to an i-th nucleotide flow, $X_1$, represents a predicted value responsive to the i-th nucleotide flow, and I, represents a total number of nucleotide flows.

In such a method, generating the data structure may comprise pruning the data structure using one or more absolute pruning rules selected from the group comprising: (i) discarding paths having a path metric larger than a best total residual metric, (ii) discarding paths having reached a last nucleotide flow, (iii) discarding paths for which a greedy decision metric exceeds a greedy penalty maximal threshold, (iv) discarding paths for which a polymerase activity is below a polymerase activity minimal threshold, (v) discarding paths including more than a threshold number of homopolymers having at least a threshold length in a row; (vi) discarding paths having a scaled residual metric below a first scaled residual minimal threshold, (vii) discarding paths having a scaled residual below a second scaled residual minimal threshold that is larger than the first scaled residual minimal threshold, and (viii) discarding paths having a greedy decision metric that exceeds the greedy decision metric for a best greedy expansion by more than a maximal threshold. Generating the data structure may comprise pruning the data structure using one or more relative pruning rules selected from the group comprising: (i) discarding paths being more than a certain number of base pairs shorter than a longest path in the data structure, and (ii) discarding paths having a highest per-flow metric whenever the number of paths exceeds a certain threshold.

Generating the set of candidate sequences may comprise determining a predicted signal for candidate sequences using a simulation framework for simulating possible state transitions for active polymerase present at a K-th base during an N-th nucleotide flow, where K and N denote indices associated with bases and nucleotide flows. The simulation framework may comprise simulating possible state transitions for situations where the K-th base matches the N-th nucleotide flow by modeling (i) a proportion of polymerase that will remain active and not incorporate base K in flow N by a first expression and (ii) a proportion of polymerase that will remain active and incorporate base K in flow N by a second expression, and the first expression may then comprise a product of (i) a measure of a quantity of active polymerase prior to the transition and (ii) a transition factor $[IER\times(1-DR)]$, and the second expression may then comprise a product of (i) the measure of the quantity of active polymerase prior to the transition and (ii) a transition factor $[(1-IER)\times(1-DR)]$, where IER represents an incomplete extension rate and DR represents a droop rate. The simulation framework may further comprise simulating possible state transitions for situations where the K-th base does not match the N-th flow by modeling (iii) a proportion of polymerase that will remain active and not incorporate base K in flow N by a third expression and (iv) a proportion of polymerase that will remain active and incorporate base K in flow N by a fourth expression, and the third expression may then comprise a product of (i) a measure of the quantity of active polymerase prior to the transition and (ii) a transition factor $[(1-CFR^M)+(CFR^M\times IER\times(1-DR))]$, and the fourth expression may then comprise a product of (i) the measure of the quantity of active polymerase prior to the transition and (ii) a transition factor $[CFR^M\times(1-IER)\times(1-DR)]$, where IER represents an incomplete extension rate, DR represents a droop rate, CFR represents a carry forward rate, and M is the smallest number such that the (N-M)-th flow matches the K-th base. The simulation framework may comprise simulating possible state transitions for situations where the K-th base does not match the N-th flow by modeling (i) a proportion of polymerase that will remain active and not incorporate base K in flow N by a first expression and (ii) a proportion of polymerase that will remain active and incorporate base K in flow N by a second expression, and the first expression may then comprise a product of (i) a measure of the quantity of active polymerase prior to the transition and (ii) a transition factor $[(1-CFR^M)$. $(CFR^M\times IER\times(1-DR))]$, and the second expression may then comprise a product of (i) the measure of the quantity of active polymerase prior to the transition and (ii) a transition factor $[CFR^M\times(1-IER)\times(1-DR)]$, where IER represents an incomplete extension rate, DR represents a droop rate, CFR represents a carry forward rate, and M is the smallest number such that the (N-M)-th flow matches the K-th base.

According to an exemplary embodiment, there is provided a non-transitory machine-readable storage medium comprising instructions which, when executed by a processor, cause the processor to perform such a method for nucleic acid sequencing or related methods and variants thereof. According to an exemplary embodiment, there is provided a system, including: a machine-readable memory; and a processor configured to execute machine-readable instructions, which, when executed by the processor, cause the system to perform such a method for nucleic acid sequencing or related methods and variants thereof.

According to an exemplary embodiment, there is provided a method for nucleic acid sequence identification, comprising: (1) obtaining information corresponding to a plurality of observed or measured nucleotide incorporation events for one or more sample nucleic acid sequences: (2) developing a plurality of predicted modelings of the observed or measured nucleotide incorporation events: (3) comparing the plurality of predicted modelings to at least one of the observed or measured nucleotide incorporation events; and (4) identifying at least a portion of the nucleic acid sequence on the basis of which predicted modeling is most similar to the observed or measured nucleotide incorporation events. The portion may cover at least two, three, four, five, six, seven, eight, nine, ten, or a larger integer, of consecutive bases called together as a whole. The method may include using a multi-element traversal approach to compare the predicted modelings to the observed or measured nucleotide incorporation events. The multi-element traversal approach may be a tree-based approach. The multi-element traversal approach may use one or more metrics selected for comparing the predicted modelings to the observed or measured nucleotide incorporation events, and may identify a path through the multi-element traversal having the best fit using the one or more metrics to determine which of the predicted modelings is most similar to the observed or measured nucleotide incorporation events.

According to an exemplary embodiment, there is provided a non-transitory machine-readable storage medium comprising instructions which, when executed by a processor, cause the processor to perform such a method for nucleic acid sequence identification or related methods and variants thereof. According to an exemplary embodiment, there is provided a system, including: a machine-readable memory; and a processor configured to execute machine-readable instructions, which, when executed by the processor, cause the system to perform such a method for nucleic acid sequence identification or related methods and variants thereof.

In an exemplary embodiment, the base caller module may receive data in WELLS file format. The base caller module may store, transmit, and/or output reads and related information in a standard flowgram format ("SFF"), for example.

Read Filter Module

In an exemplary embodiment, a read filter module or read filter may be configured to generate quality metrics for each base call of a read and for each read of a set of reads. For example, adapter sequences or other low quality base calls may be trimmed out. Low quality base calls may be removed from the output data by filtering out entire reads and/or trimming low quality 3' ends of reads using various filters and protocols.

Quality Scoring:

In an exemplary embodiment, the read filter module may be configured to assign per-base quality scores to each read, and the per-base quality scores can be written to an SFF file along with the read itself. The per-base quality scores can be assigned by calculating metrics for the read, which metrics may be analyzed by comparison to a pre-defined quality lookup table, which may be a phred-like table established through prior system training. (Phred quality scores, which were created by the program phred to aid in sequencing nucleic acid (DNA) in the Human Genome Project, can characterize the quality of a DNA sequence.) A phred quality score Q may be defined as a property that is logarithmically related to a base-calling error probability P, such that $Q=-10$ log P or equivalently $P=10^{(Q/10)}$. Thus, when referring to a $Q_{20}$ assigned to a specific base, for example, it is meant that a base with $Q_{20}$ has a 0.99 probability of being correct. The metrics may include estimates of accuracy of the current base call, nucleotide flow, and earlier or later base calls or nucleotide flows for each read. The quality scores may be based on nucleotide flow values for each base, from which several quality predictors can be calculated. The quality look-up table may be generated by selecting a representative data set to use as a training set, which may use a variety of quality predictors to characterize the quality of a base call. See Brockman et al., Genome Research 18:763-770 (2008), which is incorporated by reference herein in its entirety. In an exemplary embodiment, the read filter module may be configured to use quality predictors, which may include base position, local noise, read noise, multiple incorporations, phase error, and environment noise, for example, as part of an index to look-up an appropriate quality score for the base call in phred-like quality look-up table.

In an exemplary embodiment, the base position quality predictor may be the base position in the read from the start of the nucleic acid sequence. The local noise quality predictor may be the noise in an immediate neighborhood of a given base, which neighborhood may be varied depending on the particulars of the application and run (e.g., the local noise quality predictor may be defined to be within plus or minus (+) one base of the given base, or within #2 bases of the given base, for example. The read noise quality predictor may be a peak-normalized expression of the mean and the standard deviation of all ( ) mers and 1-mers of a read. The multiple incorporations quality predictor may, in the case of multiple incorporations of the same nucleotide in one nucleotide flow (a homopolymer region), assign to the last base in the homopolymer region a value equivalent to the total number of incorporations during that particular nucleotide flow (while all other bases in the homopolymer region can be assigned a value of 1). The phase error quality predictor may be the number of incorporations of the same nucleotide in the previous nucleotide flow. The environment noise quality predictor may be the noise in a larger neighborhood of a given base, the area of which neighborhood may vary depending on the application and run (e.g., the environmental noise quality predictor may be in a larger neighborhood which is defined to be within ±10 bases of the given base, or within ±5 bases, ±6 bases, ±7 bases, ±8 bases, ±9 bases, ±11 bases, ±12 bases, or more, for example. In an exemplary embodiment, the quality predictors may include a phase error combined with one or more of base position, local noise, read noise, multiple incorporations, and environment noise.

In an exemplary embodiment, after a quality look-up table has been generated, the quality look-up table may be used to assign a per base quality score independent of alignment. For example, quality predictors can be calculated for each base of a sample nucleic acid sequence template. The corresponding per base quality score may be determined by locating, in the quality look-up table, the first line for which the six above-mentioned calculated quality predictors, for example, are less than or equal to the quality predictor values in the quality look-up table. The quality score then can be read from the same line.

Filtering Reads:

In an exemplary embodiment, the read filter module may be configured to calculate an overall quality metric representing the base caller module's ability to correct accurately and base call the raw signal measurements. Low quality reads can be mixed reads or very low copy-count reads that produce low quality nucleic acid sequences such that they do not fit an expected incorporation model, for example. Reads identified as low quality typically may be excluded and not written to the SFF or FASTQ file.

Various types of filtering may occur. For example, reads that are derived from wells with non-clonal nucleic acid template populations and/or that are generally a poor fit to the base calling model's expectations for high quality data may be targeted for removal, whether because of low or poor signal quality from the well or a low copy count of sample nucleic acid templates. Specifically, particles or wells identified to non-clonal nucleic acids typically are filtered from the data as they contain a mixture of different nucleic acid templates (which may result from nucleic acid templates that are amplified on a single particle but are derived from multiple, different input nucleic acid templates).

A mixed nucleic acid template read can occur because of the presence of two or more distinct nucleic acid fragments in a vesicle or droplet at the start of an emulsion PCR stage, for example, or because of the collapsing together of different emulsion vesicles or droplets. Regardless of origin, mixed nucleic acid template reads can be identified by searching for reads in which an unusually large proportion of nucleotide flows are estimated to result in a nucleotide incorporation event. For example, when no mixed nucleic acid template reads exist, each particle will have a single sample nucleic acid template species amplified onto it. Based on a four-nucleobase flow cycle and uniform and random nucleotide content in the sample nucleic acid sequence template, sequencing of such a sample nucleic acid template is expected to result in approximately one-half (50%) of the nucleotide flows having a positive nucleotide incorporation event. By contrast, when a particle contains multiple different sample nucleic acid templates, or mixed nucleic acid template reads, the number of nucleotide flows with a positive nucleotide incorporation event signal can be expected to increase substantially.

In an exemplary embodiment, the read filter module may be configured to filter based on a percentage of positive flows ("PPF"). The PPF (percentage of positive flows nucleotide incorporation events based on the total number of nucleotide flows) may be evaluated over a given number of nucleotide flows, for example, the first 30 nucleotide flows, the first 40 nucleotide flows, the first 60 nucleotide flows, or the first 75 nucleotide flows, for example.

In an exemplary embodiment, the read filter module may be configured to filter reads based on non-PPF criteria. For example, read filtering may include targeted removal of reads that are generally a poor fit to the base calling model's expectations for high quality data. A typical or "well-behaved" read can be modeled and will have certain expectations about its signal distribution. For example, after the amount of incomplete extension and carry forward phasing effects have been estimated, certain expectations are present for how signals in neighboring nucleotide flows should be elevated or depressed. For example, when a positive incomplete extension is in effect, a large homopolymer sequence should result in a depressed signal in the nucleotide flow corresponding to the homopolymer while an elevated signal should be present in the next nucleotide flow of the same nucleotide.

In an exemplary embodiment, the read filter module may be configured to filter reads based on a difference between an observed signal and an expected signal based on a prediction of a base calling model for each nucleotide flow for each read (which may be referred to as the flow residual for the well and nucleotide flow in question, e.g., flow residual equals observed signal minus predicted signal). In general, a high quality read which is well-described by the base calling model and the nucleic acid sequence that it estimates should have a low residual value. In an exemplary embodiment, the median absolute value of the flow residual values over a number of initial nucleotide flows may be tracked for each read as a measure of the agreement between the observed data and the base calling model. If the median absolute flow residual value of a read is greater than a predefined threshold, then the read may be considered unreliable and it may be filtered and excluded from further processing. In various exemplary embodiments, the median absolute flow residual value can be determined over the first 30 nucleotide flows, the first 40 nucleotide flows, the first 50 nucleotide flows, the first 60) nucleotide flows, or the first 70 nucleotide flows, for example. In various exemplary embodiments, if the median absolute flow residual value is above a threshold of about 0.1, about 0.12, about 0.13, about 0.15, or about 0.2, or greater, for example, the read may be filtered from the set of reads. For these criteria, a median absolute flow residual value filter can be applied to reads of both library fragments and test fragments.

Alternatively or in addition to the above, other characteristics of reads can be identified and evaluated to determine whether the read should be filtered as being of low quality. For example, the strength of the signal from a particular well can be evaluated over the first two, three, or four key nucleotides. A key nucleotide can be a nucleotide that is present in a library sequencing key or a test fragment sequencing key. Reads for wells that do not produce a strong signal across each of the predetermined number of (key) nucleotides may be filtered. Also, a read can be required to contain a minimum number (threshold) of base calls (nucleotides) to avoid identification as a low quality read. For example, a threshold read length can be at least 6 bases, at least 8 bases, at least 10 bases, at least 12 bases, at least 15 bases, at least 20 bases, or at least 25 bases, or more, for example. If a read does not contain the threshold read length, the read can be filtered from the set of reads for further processing. Further, in certain embodiments where sequencing keys are used, a read filter can require an exact match of a sequence of the read to the corresponding library sequencing key for that run. If an exact match is not identified, the read can be filtered.

Filtering or Trimming Base Calls:

In an exemplary embodiment, the read filter module may be configured to trim a read (e.g., by excising or removing one or more nucleotides (base calls) from the read) until an acceptable level of quality persists for the remaining portion of the read, rather than filtering a read in its entirety. A trimmed read may be used in further processing and/or written to a SFF or FASTQ file. For example, a read that contains an adapter sequence (e.g., a B-adapter) may be trimmed to remove the adapter sequence and other base calls determined to be of low quality. Searching a read for a match to a known adapter sequence may be done in flow-space using flow-space vectors. The effects of incomplete extension and carry forward phasing may be reversed to produce a phase-corrected ionogram (which can be stored in a SFF file). If a read extends into the adapter sequence, 3' end of the phase-corrected ionogram can exhibit a pattern that is characteristic of the adapter sequence. In some embodiments, each position of the phase-corrected ionogram may be tested to determine whether it matches the pattern expected for the adapter sequence. Testing can include computing the Euclidean distance between the phase-corrected ionogram at the test position and the known ionogram for the adapter. If the distance falls below an adapter ionogram distance threshold, the corresponding position (translated from flow-space format back to base-space format) may be marked and/or recorded as an adapter trim location. If the distance does not fall below the adapter ionogram distance threshold, that position of the read does not match to the adapter sequence. In an embodiment, the adapter ionogram distance threshold may be a Euclidean distance of 5. In other embodiments, the adapter ionogram distance threshold may be a distance of 2, 3, 4, 6, 7, 8, 9, or more, for example.

Read trimming usually occurs at 3' end of a read. However, in certain embodiments, base calls at the 5' end of a read can be trimmed, for example, where the base calls correspond to a sequencing key such as a library sequencing key. Considering the distribution of per base quality scores within a read, the highest quality base calls tend to occur at the start of the read, where phase errors typically are the smallest. The trimming of low quality base calls at 3' end of a read may performed using a per base quality score threshold.

In various exemplary embodiments, base call trimming using a per base quality score may include scanning along the base calls of a read and computing a moving average in a fixed-length base call window along the read. A read trim point can be set to trim the earliest (5"-most) base call at which the moving average of the per base quality score drops below a moving average base quality score threshold. The base call window size may be 30 base calls and the moving average base quality score threshold, below which trimming will occur, may be a quality score of nine, for example. Of course, depending upon the particular run and application, the window size can be five base calls, 10 base calls, 15 base calls, 20 base calls, 25 base calls, 35 base calls, or 40 base calls, or more, for example. The moving average base quality score threshold also can vary depending on many factors and can be a quality score of 5, 6, 7, 8, 10, 11, 12, 13, 14, or 15, or more, for example.

As with other filters, each read trimming filter can be applied independently and the resulting, trimmed read length used in further processing or written to an appropriate file can be the sequence with the shortest length, which should contain only high quality base calls based on the filtering criteria. If the resulting trimmed read length is shorter than the threshold read length, the read can be filtered out entirely.

In an exemplary embodiment, a read filter module may receive an SFF file. The read filter module can store, transmit and/or output trimmed reads and/or a filtered set of reads, and related data and information (for example, for each read, an adapter marker, a sequence key, and/or threshold and quality markers such as per base quality scores, indications of cuts to the reads, and/or the thresholds used in analysis of the data) in SFF or FASTQ file format as well as in a Sequence Alignment/Map ("SAM") file.

According to an exemplary embodiment, there is provided a method of nucleic acid sequencing, including: (1) generating a per base quality score for each base call of a read including consecutive base calls associated with a sample nucleic acid of a defined space, each base call being derived from a signal indicative of an hydrogen ion concentration in the defined space, and the read being among a plurality of reads from a plurality of defined spaces: (2) removing from the read at least one of: (a) a base call identified as having a per base quality score below a per base quality score threshold, and (b) an adapter sequence; and (3) removing, from the plurality of reads, a read identified as at least one of: (a) a mixed template read, and (b) a read wherein a median absolute residual value is greater than a residual threshold value. After the removing steps, the remaining and revised reads of the plurality of reads form a filtered set of reads. In such a method, generating a per base quality score may include: calculating at least a first quality predictor value and a second quality predictor value for a base call, the first and second quality predictor values including at least one parameter selected from the group consisting of base position, local noise, read noise, multiple incorporations, phase error, and environment noise: comparing the calculated first quality predictor value and the calculated second quality predictor value to a pre-defined quality metric; and assigning a per base quality score to the base call based on the comparison. The at least one parameter may include a phase error as well as at least one other parameter selected from the group consisting of base position, local noise, read noise, multiple incorporations, and environment noise. In this method, the pre-defined quality metric may include a phred-like table.

According to an exemplary embodiment, there is provided a non-transitory machine-readable storage medium comprising instructions which, when executed by a processor, cause the processor to perform such a method for nucleic acid sequencing or related methods and variants thereof. According to an exemplary embodiment, there is provided a system, including: a machine-readable memory; and a processor configured to execute machine-readable instructions, which, when executed by the processor, cause the system to perform such a method for nucleic acid sequencing or related methods and variants thereof.

FIG. 29 illustrates a correlation plot showing empirical vs. predicted quality scores according to an exemplary embodiment. The predicted quality scores are based on quality scores derived from probabilities of error using a phred-like quality score. The empirical scores are actual quality score based on reads compared against a known reference. The plot shows a high correlation between predicted and actual quality scores.

Alignment Module

In an exemplary embodiment, an alignment module or aligner may be configured to align reads of a plurality of sample nucleic acids to determine a longer portion of a sample nucleic acid sequence. The alignment module may be based on a TMAP aligner or a BFAST aligner, for example, and may accept as input(s) some or all of the reads, which may include a set of filtered reads received from the read filter module. The alignment module may receive data in SFF file format or FASTQ file format, for example, and it may store, transmit, and/or output one or more sample nucleic acid sequences and related data and information in SAM or BAM file format, for example. The alignment module may also advantageously search, query, and/or use various reference genome and index files to facilitate an alignment and/or as a quality control measure.

In an exemplary embodiment, the alignment module or aligner may further be configured to perform one or more alignment quality control processes, which may include determining whether an identified sample nucleic acid sequence was obtained within an acceptable tolerance limit. The tolerance limit may be defined by the number or percentage of reads that align, and the quality of the alignment may be tested using BFAST, for example.

According to an exemplary embodiment, there is provided a method of nucleic acid sequencing, including: (1) receiving a plurality of signals indicative of a parameter measured for a plurality of defined spaces, at least some of the defined spaces including one or more sample nucleic acids, the signals being responsive to a plurality of nucleotide flows introducing nucleotides to the defined spaces: (2) determining, for at least some of the defined spaces, whether the defined space includes a sample nucleic acid: (3) processing, for at least some of the defined spaces determined to include a sample nucleic acid, the received signals to improve a quality of the received signals; and (4) predicting a plurality of nucleotide sequences corresponding to respective sample nucleic acids for the defined spaces based on the processed signals and the nucleotide flows.

In such a method, in the receiving step, the parameter measured for the defined spaces may include a voltage measurement indicative of hydrogen ion concentration for respective defined spaces. At least some of the defined spaces may include a sample nucleic acid directly or indirectly coupled to a particle. At least some of the defined spaces may include a sample nucleic acid directly or indirectly coupled to a surface of the defined space. The defined spaces may include microwells associated with sensors formed from an integrated circuit chip. The determining step may include evaluating a difference between a first rate of change in an hydrogen ion concentration for the defined space measured for a first solution having a first pH and a second rate of change in the hydrogen ion concentration for the defined space measured for a second solution having a second pH different from the first pH. The determining step may include comparing a rate of change in an hydrogen ion concentration for the defined space measured for a solution having a given pH with a modeled rate of change for the defined space not containing a sample nucleic acid. The determining step may include evaluating, for at least some of the defined spaces determined to include a sample nucleic acid, whether the signals for the defined space are informative or non-informative. The determining step may further include evaluating, for at least some of the defined spaces determined to include a sample nucleic acid and to be informative, whether the defined space includes a library fragment, a test fragment, or an ambiguous fragment. The determining step may further include comparing a flow-space incorporation vector derived from a portion of the signals responsive to a set of initial nucleotide flows for the defined space with at least two pre-defined vectors. The at least two pre-defined vectors may include one or more library fragment flow-space vector. The at least two pre-defined vectors may include one or more test fragment flow-space vector. The at least two pre-defined vectors may include a library fragment flow-space vector that would be expected to result if a pre-defined library fragment key sequence were subjected to the initial nucleotide flows, and a test fragment flow-space vector that would be expected to result if a pre-defined test fragment key sequence were subjected to the initial nucleotide flows. The library fragment flow-space vector and the test fragment flow-space vector may be orthogonal under the set of initial nucleotide flows with respect to at least one, at least two, at least three, or all four of nucleotides A. C. G. and T (as further explained above). The processing step may include modifying the signals to remove noise, the noise being evaluated based at least partly on signals for defined spaces determined not to include a sample nucleic acid. The predicting step may include normalizing the processed signals: estimating, for at least some of the defined spaces determined to include a sample nucleic acid, a number of nucleotide incorporations that occurred in the defined space as a result of each of the nucleotide flows based on the normalized processed signals; and compiling the estimated numbers of nucleotide incorporations for the nucleotide flows into one or more sequences of consecutive base calls for the sample nucleic acid to form one or more reads. The number of nucleotide incorporations may be selected for each of the nucleotide flows from the group consisting of zero, one, two, three, and any other positive integer. The predicting step may further include aligning the one or more reads to predict a sample nucleic acid sequence assembled from the one or more reads for the sample nucleic acids. The predicting step may further include generating a quality metric for the base calls and for the reads; and filtering out from the one or more reads at least one of: any read that contains at least a threshold number of base calls failing to meet a minimal threshold of base call quality, and any read that fails to meet a minimal threshold of read quality. The predicting step may further include generating a quality score for at least some of the base calls forming at least a portion of the one or more reads. The generating step may include calculating at least a first quality predictor value and a second quality predictor value for each base call, the first and second quality predictor values including at least one parameter selected from the group consisting of base position, local noise, read noise, multiple incorporations, phase error, and environment noise; comparing the calculated first quality predictor value and the calculated second quality predictor value to a pre-defined quality metric; and assigning a quality score to the at least some of the base calls based upon the comparison. The at least one parameter may include a phase error as well as at least one other parameter selected from the group consisting of base position, local noise, read noise, multiple incorporations, and environment noise. The predicting step may include removing from the at least some of the base calls forming at least a portion of the one or more reads at least one of: any base call identified as having a quality score below a quality score threshold, and an adapter sequence; and filtering out from the at least a portion of the one or more reads at least one of: any read identified as a mixed template read, and any read identified as having a median absolute residual value greater than a residual threshold value, thereby generating a filtered set of reads. The predicting step may further include aligning the filtered set of reads to predict a sample nucleic acid sequence assembled from the filtered set of reads for the sample nucleic acids. The method may include transmitting, displaying, storing, printing or outputting to a user interface device, a computer readable storage medium, a local computer system or a remote computer system, information related to the predicted nucleotide sequences of the sample nucleic acids or other parameters, predictions, data or signals generated or used by the method.

According to an exemplary embodiment, there is provided a non-transitory machine-readable storage medium comprising instructions which, when executed by a processor, cause the processor to perform such a method for nucleic acid sequencing or related methods and variants thereof. According to an exemplary embodiment, there is provided a system, including: a machine-readable memory; and a processor configured to execute machine-readable instructions, which, when executed by the processor, cause the system to perform such a method for nucleic acid sequencing or related methods and variants thereof.

According to an exemplary embodiment, there is provided a method of nucleic acid sequencing, including: (1) receiving, for each of a plurality of defined spaces, a series of signals indicative of an hydrogen ion concentration in the defined space, at least some of the defined spaces including a sample nucleic acid: (2) identifying, from the received series of signals, one or more sequences of nucleotide type and corresponding number of nucleotide incorporations for each sample nucleic acid, thereby providing one or more reads including consecutive base calls associated with the sample nucleic acids; and (3) aligning the one or more reads to determine a sample nucleic acid sequence. In such a method, in the receiving step, the signals may include voltage measurements indicative of the hydrogen ion concentration in the defined space. At least some of the defined spaces may include a sample nucleic acid directly or indirectly coupled to a particle. At least some of the defined spaces may include a sample nucleic acid directly or indirectly coupled to a surface of the defined space. The defined spaces may include microwells associated with sensors formed from an integrated circuit chip. According to an exemplary embodiment, there is provided a non-transitory machine-readable storage medium comprising instructions which, when executed by a processor, cause the processor to perform such a method for nucleic acid sequencing or related methods and variants thereof.

According to an exemplary embodiment, there is provided a system, including: (1) a data processing module configured to receive a series of signals characteristic of an hydrogen ion concentration associated with reaction confinement regions or defined spaces associated with at least one sample nucleic acid; and (2) a classification module configured to determine a presence or absence of a sample-containing particle in the reaction confinement regions or defined spaces. The system may further include a signal processing module configured to analyze data and/or signals derived from the reaction confinement regions or defined spaces determined to contain a sample-containing particle, and to output signals indicative of nucleotide incorporation events or non-events. The system may further include a base caller module configured to transform the output signals into base calls and compile consecutive base calls for the at least one sample nucleic acid into at least one read including a plurality of sequential or consecutive base calls associated with the at least one sample nucleic acid. The system may further include a read filter module configured to generate a quality metric for each base call and for each read to facilitate filtering out of low quality reads. The system may further include an alignment module configured to align the reads of a plurality of sample nucleic acids to determine a sample nucleic acid sequence. The system may further include a data output module configured to transmit, display, store, print or output to a user interface device, a computer readable storage medium, a local computer system or a remote computer system, information related to the determined nucleotide sequence or other parameters, predictions, data or signals generated or used by the system.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem: for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

---

SEQUENCE LISTING

```
Sequence total quantity: 2
SEQ ID NO: 1          moltype = DNA  length = 16
FEATURE               Location/Qualifiers
source                1..16
                      mol_type = unassigned DNA
                      organism = Synthetic construct
                      note = Exemplary Strand
SEQUENCE: 1
agtcaagcgt cccatg                                          16

SEQ ID NO: 2          moltype = DNA  length = 10
FEATURE               Location/Qualifiers
source                1..10
                      mol_type = unassigned DNA
                      organism = Synthetic construct
                      note = Exemplary Strand
SEQUENCE: 2
tcagttgact                                                 10
```

--- oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional exemplary embodiments may be derived by repeating, adding, or substituting any generically or specifically described features and/or components and/or substances and/or steps and/or operating conditions set forth in one or more of the above-described exemplary embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed exemplary embodiments may be considered to be a potential optional feature, component, aspect, step, or other characteristic of any other of the above-discussed exemplary embodiments so long as the objective of such any other of the above-discussed exemplary embodiments remains achievable, unless specifically stated otherwise.

The invention claimed is:

1. A system, comprising:
a machine-readable memory; and
a processor configured to execute machine-readable instructions, which, when executed by the processor, cause the system to perform steps including:
for each of a plurality of defined spaces of a chip or substrate, wherein each defined space is in communication with a respective sensor and wherein at least some of the defined spaces comprise one or more sample nucleic acids, receiving, from the respective sensor for each defined space, an observed or measured signal indicative of a parameter observed or measured for the defined space in response to a nucleotide flow to the defined space, to provide a measured signal value representative of a non-incorporation or an incorporation of a base corresponding to the nucleotide flow by the sample nucleic acid in the defined space, wherein each defined space is a space in which at least some of a molecule, fluid, and/or a solid can be confined, retained and/or localized, wherein the plurality of defined spaces comprises at least 100,000 defined spaces;
generating, for the defined spaces comprising one or more sample nucleic acids, a set of candidate sequences of bases for the one or more sample nucleic acids of the defined space, including generating a data structure comprising a set of partial paths corresponding to candidate sequences undergoing an expansion in a stepwise manner one base at a time:
generating a set of predicted signal values for the set of candidate sequences based on a simulation framework for modeling responses by an active polymerase associated with the sample nucleic acid to a series of nucleotide flows, wherein the simulation framework includes possible states, state transitions and state transition parameters, wherein a first state of the possible states represents a non-incorporation of a particular base at a particular flow of the series of nucleotide flows and a second state of the possible states represents an incorporation of the particular base at the particular flow by the active polymerase associated with the sample nucleic acid;

applying one or more metrics adapted to associate a score or a penalty to each of the candidate sequences of bases, wherein at least one of the metrics depends on a residual between the measured signal value and the predicted signal value generated by the simulation framework, wherein the residual comprises a difference between the predicted signal value and the measured signal value; and selecting from the set of candidate sequences of bases the candidate sequence leading to a highest score or a lowest penalty as corresponding to a correct sequence for the one or more sample nucleic acids in the defined space.

2. The system of claim 1, wherein the step of generating the data structure comprises determining a distance between the predicted signal value for each partial path and the measured signal value.

3. The system of claim 2, wherein the one or more metrics comprise a metric that is a function of the distance between the predicted signal value for each partial path and the measured signal value.

4. The system of claim 2, wherein the one or more metrics comprise a metric comprising a sum of squared distances between corresponding values of the predicted signal value for each partial path and the measured signal value.

5. The system of claim 1, wherein the one or more metrics comprise a path metric comprising a sum of (i) a sum of squared residuals before an active window and (ii) a sum of squared residuals for negative residuals within the active window.

6. The system of claim 1, wherein the one or more metrics comprise a greedy decision metric comprising a sum of (i) a product of an empirical constant and a sum of squared residuals for negative residuals within an active window and (ii) a sum of squared residuals for positive residuals within the active window but only before an in-phase flow.

7. The system of claim 1, wherein the one or more metrics comprise a path metric, a greedy decision metric, and a per-flow metric, and wherein the per-flow metric comprises a weighted sum of (i) the path metric and (ii) the greedy decision metric.

8. The system of claim 1, wherein the one or more metrics comprise a scaled residual comprising a ratio between (i) a difference between a measured signal value for a current path at a current in-phase flow and a predicted signal value from a parent path at the current in-phase flow and (ii) a difference between a predicted signal value of the current path at the current in-phase flow and the predicted signal value from the parent path at the current in-phase flow.

9. The system of claim 1, wherein the one or more metrics comprise a total residual comprising a sum of squared residuals over all nucleotide flows.

10. The system of claim 1, wherein the step of generating the data structure comprises pruning the data structure using one or more absolute pruning rules selected from the group comprising: (i) discarding paths having a path metric larger than a best total residual metric, (ii) discarding paths having reached a last nucleotide flow, (iii) discarding paths for which a greedy decision metric exceeds a greedy penalty maximal threshold, (iv) discarding paths for which a polymerase activity is below a polymerase activity minimal threshold, (v) discarding paths including more than a threshold number of homopolymers having at least a threshold length in a row, (vi) discarding paths having a scaled residual metric below a first scaled residual minimal threshold, (vii) discarding paths having a scaled residual below a second scaled residual minimal threshold that is larger than the first scaled residual minimal threshold, and (viii) discarding paths having a greedy decision metric that exceeds the greedy decision metric for a best greedy expansion by more than a maximal threshold.

11. The system of claim 1, wherein the step of generating the data structure comprises pruning the data structure using one or more relative pruning rules selected from the group comprising: (i) discarding paths being more than a certain number of base pairs shorter than a longest path in the data structure, and (ii) discarding paths having a highest per-flow metric whenever the number of paths exceeds a certain threshold.

12. The system of claim 1, wherein the state transition parameters of the simulation framework comprise state transition parameters for the possible states of the active polymerase corresponding to a K-th base during an N-th nucleotide flow of the series of nucleotide flows, where K and N denote indices associated with the bases and the nucleotide flows.

13. The system of claim 12, wherein the simulation framework comprises first and second state transition parameters for the first and second states, respectively, for situations where the K-th base matches the N-th nucleotide flow, wherein (i) the first state transition parameter represents a proportion of the active polymerase that will remain active and not incorporate base K in flow N and (ii) the second state transition parameter represents a proportion of the active polymerase that will remain active and incorporate base K in flow N.

14. The system of claim 13, wherein the simulation framework further comprises:

determining the first state transition parameter by calculating a product of (i) a measure of a quantity of the active polymerase prior to a transition to the first state and (ii) a first transition factor $[IER \ x(1-DR)]$; and determining the second state transition parameter by calculating a product of (i) the measure of the quantity of the active polymerase prior to a transition to the second state and (ii) a second transition factor $[(1-IER) \times (1-DR)]$, where IER represents an incomplete extension rate and DR represents a droop rate.

15. The system of claim 12, wherein the simulation framework comprises first and second state transition parameters for the first and second states, respectively, for situations where the K-th base does not match the N-th flow, wherein (i) the first state transition parameter represents a proportion of the active polymerase that will remain active and not incorporate base K in flow N and (ii) the second state transition parameter represents a proportion of the active polymerase that will remain active and incorporate base K in flow N.

16. The system of claim 15, wherein the simulation framework further comprises:

determining the first state transition parameter by calculating a product of (i) a measure of a quantity of the active polymerase prior to a transition to the first state and (ii) a first transition factor $[(1-CFR1)+(CFR'' \times IER \times (1-DR))]$; and determining the second state transition parameter by calculating a product of (i) the measure of the quantity of the active polymerase prior to a transition to the second state and (ii) a second transition factor [$CFR^M \times (1-IER) \times (1-DR)$], where IER represents an incomplete extension rate, DR represents a droop rate, CFR represents a carry forward rate, and M is a smallest number such that an (N−M) flow matches the K-th base.

17. A method for nucleic acid sequence identification, comprising:

obtaining information corresponding to a plurality of observed or measured nucleotide incorporation events for one or more sample nucleic acid sequences, wherein the observed or measured nucleotide incorporation events are obtained from a plurality of defined spaces of a chip or substrate in response to a nucleotide flow to the defined spaces, wherein each defined space is in communication with a respective sensor and wherein at least some of the defined spaces comprise the one or more sample nucleic acids, wherein each defined space is a space in which at least some of a molecule, fluid, and/or a solid can be confined, retained and/or localized, wherein the plurality of defined spaces comprises at least 100,000 defined spaces;

developing a plurality of predicted modelings of the observed or measured nucleotide incorporation events;

comparing the plurality of predicted modelings to at least one of the observed or measured nucleotide incorporation events; and identifying at least a portion of the nucleic acid sequence on a basis of which predicted modeling is most similar to the observed or measured nucleotide incorporation events, the portion covering at least two consecutive bases called together as a whole.

18. The method of claim 17, wherein the comparing step applies a multi-element traversal to compare the predicted modelings to the observed or measured nucleotide incorporation events.

19. The method of claim 18, wherein the multi-element traversal comprises a tree-based search.

20. The method of claim 18, wherein the multi-element traversal includes one or more metrics to compare the predicted modelings to the observed or measured nucleotide incorporation events, the identifying step further comprising determining a path through the multi-element traversal having a best fit using the one or more metrics to determine which of the predicted modelings is most similar to the observed or measured nucleotide incorporation events.

* * * * *